US011312756B2

(12) United States Patent
Link et al.

(10) Patent No.: US 11,312,756 B2
(45) Date of Patent: *Apr. 26, 2022

(54) ENGINEERED POTENT CYTOTOXIC STAPLED BH3 PEPTIDES

(71) Applicant: The Trustees of Princeton University, Princeton, NJ (US)

(72) Inventors: A. James Link, Princeton, NJ (US); Siyan Zhang, Plainsboro, NJ (US)

(73) Assignee: The Trustees of Princeton University, Princeton, NJ (US)

(*) Notice: Subject to any disclaimer, the term of this patent is extended or adjusted under 35 U.S.C. 154(b) by 48 days.

This patent is subject to a terminal disclaimer.

(21) Appl. No.: 16/402,754

(22) Filed: May 3, 2019

(65) Prior Publication Data

US 2019/0309038 A1 Oct. 10, 2019

Related U.S. Application Data

(60) Division of application No. 15/265,321, filed on Sep. 14, 2016, now Pat. No. 10,344,064, which is a continuation of application No. 14/376,223, filed as application No. PCT/US2013/024617 on Feb. 4, 2013, now Pat. No. 9,464,125.

(60) Provisional application No. 61/594,810, filed on Feb. 3, 2012.

(51) Int. Cl.
| | |
|---|---|
| *A61K 38/10* | (2006.01) |
| *A61K 38/00* | (2006.01) |
| *A61P 35/00* | (2006.01) |
| *A61K 38/04* | (2006.01) |
| *C07K 5/00* | (2006.01) |
| *C07K 7/00* | (2006.01) |
| *C07K 17/00* | (2006.01) |
| *C07K 14/47* | (2006.01) |
| *C07K 7/08* | (2006.01) |
| *A61K 38/12* | (2006.01) |
| *A61K 38/17* | (2006.01) |
| *A61K 31/635* | (2006.01) |
| *G01N 33/50* | (2006.01) |
| *G01N 33/68* | (2006.01) |

(52) U.S. Cl.
CPC ........ *C07K 14/4747* (2013.01); *A61K 31/635* (2013.01); *A61K 38/00* (2013.01); *A61K 38/10* (2013.01); *A61K 38/12* (2013.01); *A61K 38/1761* (2013.01); *A61P 35/00* (2018.01); *C07K 7/08* (2013.01); *G01N 33/5014* (2013.01); *G01N 33/68* (2013.01)

(58) Field of Classification Search
None
See application file for complete search history.

(56) References Cited

U.S. PATENT DOCUMENTS

| | | | |
|---|---|---|---|
| 9,464,125 B2 * | 10/2016 | Link | ................ A61K 38/00 |
| 2005/0250680 A1 | 11/2005 | Walensky et al. | |
| 2008/0199890 A1 | 8/2008 | Letai | |
| 2009/0275519 A1 | 11/2009 | Nash et al. | |

FOREIGN PATENT DOCUMENTS

WO WO-2009099677 A2 * 8/2009 ............. A61K 45/06

OTHER PUBLICATIONS

Aquino, "Predicting response to therapy with BH3 profiling," Cap Today, available online at https://www.captodayonline.com/predicting-response-to-therapy-with-bh3-profiling/, 5 pages (2020) (Year: 2020).*
Boston University, "Administration of Drugs and Experimental Compounds in Mice and Rats," available online at https://www.bu.edu/researchsupport/compliance/animal-care/working-with-animals/procedures/administration-of-drugs-and-experimental-compounds-in-mice-and-rats/, 12 pages (first available 2009) (Year: 2009).*
Chipuk et al., "The BCL-2 Family Reunion," Molecular Cell 37, Feb. 12, 2010, pp. 299-310.
Walensky, L.D., "BCL-2 in the crosshairs; tipping the balance of life and death," Cell Death and Differentiation (2006) 13, 1339-1350.
Chipuk et al., "How do BCL-2 proteins induce mitochondrial outer membrane permeabilization?" Trends in Cell Biology, vol. 18, No. 4, pp. 157-164.
Sattler et al., "Structure of Bcl-xL-Bak Peptide Complex: Recognition Between Regulators of Apoptosis," Science, vol. 275, Feb. 14, 1997, pp. 983-986.
Tsujimoto et al., "Involvement of the bcl-2 Gene in Human Follicular Lymphoma," Science, vol. 228 (1985), pp. 1440-1443.
Placzek et al., "A survey of the anti-apoptotic Bcl-2 subfamily expression in cancer types provides a platform to predict the efficacy of Bcl-2 antagonists in cancer therapy," Cell Death and Disease (2010) 1, pp. 1-9.
Letai, Anthony G., "Diagnosing and exploiting cancer's addiction to blocks in apoptosis," Nature Reviews Cancer, vol. 8, Feb. 2008, pp. 121-132.
Petros et al., "Structural biology of the Bcl-2 family proteins," Biochimica et Biophysica Acta 1644 (2004), pp. 83-94.
Labi et al., "Targeting the Bcl-2-regulated apoptosis pathway by BH3 mimetics; a breakthrough in anticancer therapy?" Cell Death and Differentiation (2008) 15, pp. 977-987.

(Continued)

*Primary Examiner* — Thea D'Ambrosio
(74) *Attorney, Agent, or Firm* — Volpe Koenig

(57) ABSTRACT

Compositions comprising peptide sequences with high cytotoxicity to cancer cell lines are provided. Pharmaceutical compositions comprising peptide sequences with high cytotoxicity to cancer cell lines are provided. A method for treating cancer is provided.

30 Claims, 36 Drawing Sheets

Specification includes a Sequence Listing.

(56) References Cited

OTHER PUBLICATIONS

Lessene et al., "BCL-2 family antagonists for cancer therapy," Nature Reviews Drug Discovery, vol. 7, Dec. 2008, pp. 989-1000.
Oltersdorf et al., "An inhibitor of Bcl-2 family proteins induces regression of solid tumours," Nature, vol. 435, Jun. 2, 2005, pp. 677-681.
Walensky et al., "Activation of Apoptosis in Vivo by a Hydrocarbon-Stapled BH3 Helix," Science, vol. 305, Sep. 3, 2004, pp. 1466-1470.
Blackwell et al., "Highly Efficient Synthesis of Covalently Cross-Linked Peptide Helices by Ring-Closing Matathesis," Angew. Chem. Int. Ed. 1998, 37, No. 23, pp. 3281-3284.
Schafmeister et al., "An All-Hydrocarbon Cross-Linking System for Enhancing the Helicity and Metabolic Stability of Peptides," J Am. Chem. Soc. 2000, 122, pp. 5891-5892.
Chapman et al., "A Highly Stable Short α-Helix Constrained by a Main-Chain Hydrogen-Bond Surrogate," J. Am. Chem. Soc. 2004, 126, pp. 12252-12253.
Verdine et al., "The Challenge of Drugging Undruggable Targets in Cancer Lessons Learned from Targeting BCL-2 Family Members," Clin. Cancer Res. 2007; 13(24) Dec. 15, 2007, pp. 7264-7270.
Sun et al., "Reconstitution and Engineering of Apoptotic Protein Interactions on the Bacterial Cell Surface," J. Mol. Biol. (2009) 394, pp. 297-305.
Zhang et al., "A Comparison of Two Strategies for Affinity Maturation of a BH3 Peptide toward Pro-Survival Bcl-2 Proteins," ACS Synth. Biol. 2012, 1, pp. 89-98.
Zhang et al., "Bcl-2 family interactome analysis using bacterial surface display," Integr. Biol., 2011, 3, pp. 823-831.
Kim et al., "Synthesis of all-hydrocarbon stapled α-helical peptides by ring-closing olefin metathesis," Nature Protocols, vol. 6, No. 6, 2011, pp. 761-771.
Bernal et al., "Reactivation of the p53 Tumor Suppressor Pathway by a Stapled p53 Peptide," J. Am. Chem. Soc. 2007, 129, pp. 2456-2457.
Stewart et al., "The MCL-1 BH3 helix is an exclusive MCL-1 inhibitor and apoptosis sensitizer," Nature Chemical Biology, vol. 6, Aug. 2010, pp. 595-601.
Rice et al., "Directed evolution of a biterminal bacterial display scaffold enhances the display of diverse peptides," Protein Engineering, Design & Selection, vol. 21 No. 7, 2008, pp. 435-442.
Chen et al., "Differential Targeting of Prosurvival Bcl-2 Proteins by Their BH3-Only Ligands Allows Complementary Apoptotic Function," Molecular Cell, vol. 17, Feb. 4, 2005, pp. 393-403.
Dutta et al., "Determinants of BH3 Binding Specificity for Mcl-1 versus Bcl-xL," J. Mol. Biol. (2010) 398, pp. 747-762.
Quinn et al., "Targeting Mcl-1 for the therapy of cancer," Expert Opin. Investig. Drugs (2011) 20(10), pp. 1397-1411.
Chen et al., "Mcl-1 Down-regulation Potentiates ABT-737 Lethality by Cooperatively Inducing Bak Activation and Bax Translocation," Cancer Res 2007; 67:(2), Jan. 15, 2007, pp. 782-791.
Lee et al., "A novel BH3 ligand that selectively targets Mcl-1 reveals that apoptosis can proceed without Mcl-1 degradation," Journal of Cell Biology, vol. 180, No. 2, Jan. 28, 2008, pp. 341-355.
van Delft et al., "The BH3 mimetic ABT-737 targets selective Bcl-2 proteins and efficiently induces apoptosis vai Bak/Bax if Mcl-1 is neutralized," Cancer Cell 10, Nov. 2006, pp. 389-399.
Gavathiotis et al., "BAX activation is initiated at a novel interaction site," Nature, vol. 455, Oct. 23, 2008, pp. 1076-1082.
Li et al., "Amplification of LAPTM4B and YWHAZ continues to chemotherapy resistance and recurrence of breast cancer," Nature Medicine, vol. 16, No. 2, Feb. 2010, pp. 214-219.
Basma et al., "BCL-2 antisense and cisplatin combination treatment of MCF-7 breast cancer cells with or without functional p53," Journal of Biomedical Science (2005) 12, pp. 999-1011.
Takara et al., "Molecular changes to HeLa cells on continuous exposure to cisplatin or paclitaxel," Cancer Chemother Pharmacol (2006) 58, pp. 785-793.
Thallinger et al., "Mcl-1 Is a Novel Therapeutic Target for Human Sarcoma: Synergistic Inhibition of Human Sarcoma Xenotransplants by a Combination of Mcl-1 Antisense Oligonucleotides with Low-Dose Cyclophosphamide," Clinical Cancer Research, vol. 10, Jun. 15, 2004, pp. 4185-4191.
Thallinger et al., "Mcl-1 Antisense Therapy Chemosensitizes Human Melanoma in a SCID Mouse Xenotransplantation Model," Journal of Investigative Dermatology (2003), pp. 1081-1086.
Hussain et al., "Mcl-1 Is a Relevant Therapeutic Target in Acute and Chronic Lymphoid Malignancies: Down-Regulation Enhances Rituximab-Medicated Apoptosis and Complement-Dependent Cytotoxicity," Clin. Cancer Res 2007:13(7), Apr. 1, 2007, pp. 2144-2150.
Selzer et al., "Expression of bcl-2 family members in human melanocytes, in melanoma metastases and in melanoma cell lines," Melanoma Research, vol. 8, 1998, pp. 197-203.
Dowling et al., "Antitumor Activity of Titanocene Y in Xenografted PC3 Tumors in Mice," Letters in Drug Design & Discovery, 2008, 5, pp. 141-144.
Bruncko et al., "Studies Leading to Potent, Dual Inhibitors of Bcl-2 and Bcl-xL," J. Med. Chem. 2007, 50, 641-662.
Souers et al., Nat. Med. 19-202-210 (2013).

* cited by examiner

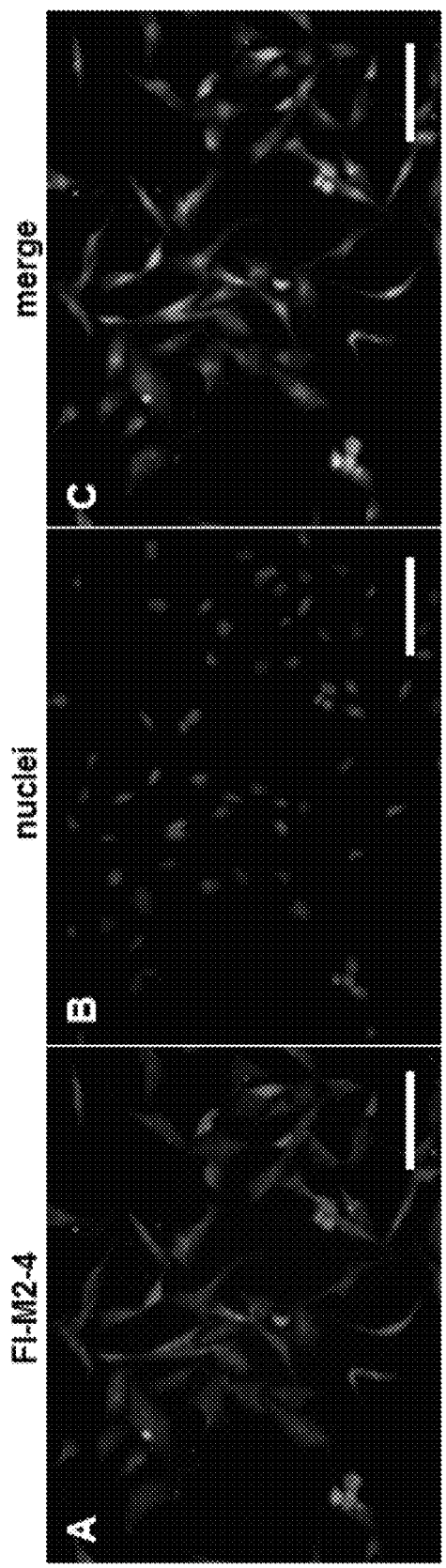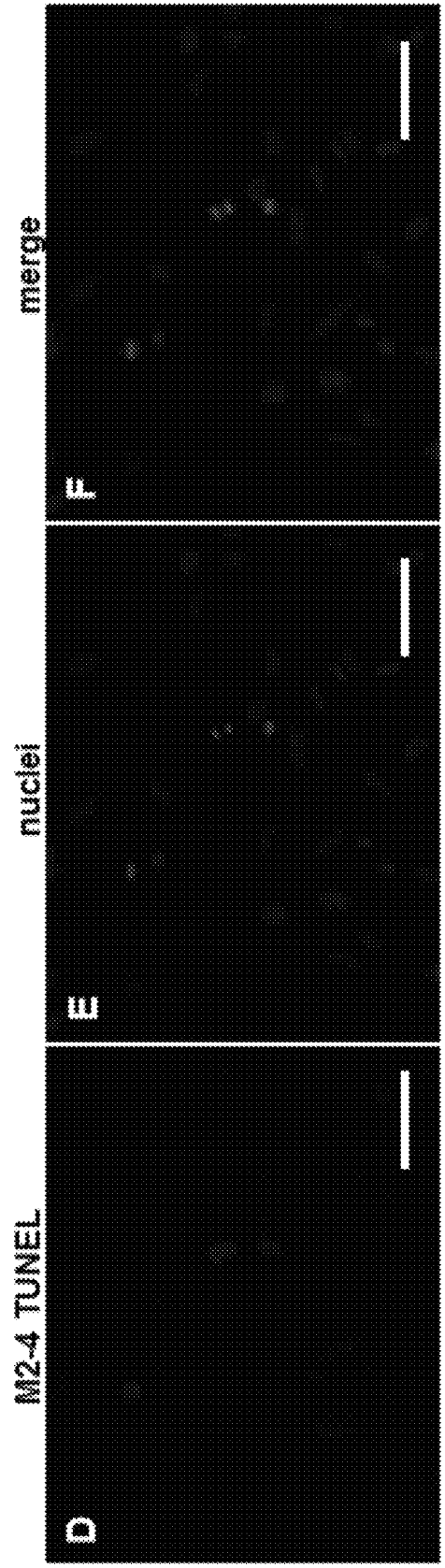
FIG. 4A  FIG. 4B  FIG. 4C
FIG. 4D  FIG. 4E  FIG. 4F

SEQUENCE LISTING

```
<160> NUMBER OF SEQ ID NOS: 42

<210> SEQ ID NO 1
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (5)..(5)
<223> OTHER INFORMATION: Xaa can be any amino acid
<220> FEATURE:
<221> NAME/KEY: misc_feature
<222> LOCATION: (9)..(9)
<223> OTHER INFORMATION: Xaa can be any amino acid
<220> FEATURE:
<221> NAME/KEY: misc_feature
<222> LOCATION: (13)..(13)
<223> OTHER INFORMATION: Xaa can be any amino acid

<400> SEQUENCE: 1

Trp Xaa Ala Gln Xaa Leu Arg Arg Xaa Gly Asp Glu Xaa Asn
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetic construct

<400> SEQUENCE: 2

Trp Val Ala Gln Trp Leu Arg Arg Trp Gly Asp Glu Phe Asn
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic construct

<400> SEQUENCE: 3

Trp Tyr Ala Gln Ile Leu Arg Arg Met Gly Asp Glu Phe Asn
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic construct
```

```
<400> SEQUENCE: 4

Trp Leu Ala Gln Leu Leu Arg Arg Tyr Gly Asp Glu Phe Asn
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic construct

<400> SEQUENCE: 5

Trp Ile Ala Gln Ile Leu Arg Arg Trp Gly Asp Glu Phe Asn
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic construct

<400> SEQUENCE: 6

Trp Val Ala Gln Thr Leu Arg Arg Trp Gly Asp Glu Phe Asn
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Synthetic construct

<400> SEQUENCE: 7

Trp Ile Ala Gln Leu Leu Arg Arg Ile Gly Asp Glu Val Asn
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Synthetic construct

<400> SEQUENCE: 8

Trp Val Ala Gln Leu Leu Arg Arg Ile Gly Asp Glu Val Asn
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Synthetic construct

<400> SEQUENCE: 9

Trp Met Ala Gln Ile Leu Arg Arg Ile Gly Asp Glu Val Asn
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic construct

<400> SEQUENCE: 10
```

Trp Leu Ala Gln Leu Leu Arg Arg Ile Gly Asp Glu Ile Asn
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Synthetic construct

<400> SEQUENCE: 11

Trp Leu Ala Gln Glu Leu Arg Arg Ile Gly Asp Glu Val Asn
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Synthetic construct

<400> SEQUENCE: 12

Trp Ile Ala Gln Glu Leu Arg Arg Ile Gly Asp Glu Phe Asn
1               5                   10

<210> SEQ ID NO 13
<211> LENGTH: 61
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t

<400> SEQUENCE: 13
gtctggccag tggnnkgccc aannkttgcg gcgtnnkgga gacgagnnka acggagggca      60
g                                                                    61

<210> SEQ ID NO 14
<211> LENGTH: 61
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t

```
<220> FEATURE:
<221> NAME/KEY: misc_feature
<222> LOCATION: (47)..(48)
<223> OTHER INFORMATION: n is a, c, g, or t

<400> SEQUENCE: 14
ctgccctccg ttmnnctcgt ctccmnnacg ccgcaamnnt tgggcmnncc actggccaga    60
c                                                                   61

<210> SEQ ID NO 15
<211> LENGTH: 26
<212> TYPE: DNA
<213> ORGANISM: Artificial Sequence
<220> FEATURE:
<223> OTHER INFORMATION: Synthetic construct

<400> SEQUENCE: 15
gcaactctct actgtttctc catacc                                        26

<210> SEQ ID NO 16
<211> LENGTH: 28
<212> TYPE: DNA
<213> ORGANISM: Artificial Sequence
<220> FEATURE:
<223> OTHER INFORMATION: Synthetic construct

<400> SEQUENCE: 16
ccaaaacagc caagcttggc caccttgg                                      28

<210> SEQ ID NO 17
<211> LENGTH: 52
<212> TYPE: DNA
<213> ORGANISM: Artificial Sequence
<220> FEATURE:
<223> OTHER INFORMATION: Synthetic construct

<400> SEQUENCE: 17
ccgtagctgg ccagtctggc cagtggatcg cccaacagtt gcggcgtatt gg            52

<210> SEQ ID NO 18
<211> LENGTH: 52
<212> TYPE: DNA
<213> ORGANISM: Artificial Sequence
<220> FEATURE:
<223> OTHER INFORMATION: Synthetic construct

<400> SEQUENCE: 18
ccgtagctgg ccagtctggc cagtggatcg cccaattgtt gcggcgtatt gg            52

<210> SEQ ID NO 19
<211> LENGTH: 52
<212> TYPE: DNA
<213> ORGANISM: Artificial Sequence
<220> FEATURE:
<223> OTHER INFORMATION: Synthetic construct

<400> SEQUENCE: 19
ccgtagctgg ccagtctggc cagtggatcg cccaaacttt gcggcgtatt gg            52

<210> SEQ ID NO 20
<211> LENGTH: 52
<212> TYPE: DNA
<213> ORGANISM: Artificial Sequence
<220> FEATURE:
<223> OTHER INFORMATION: Synthetic construct
```

<400> SEQUENCE: 20
ccgtagctgg ccagtctggc cagtggatcg cccaatggtt gcggcgtatt gg            52

<210> SEQ ID NO 21
<211> LENGTH: 52
<212> TYPE: DNA
<213> ORGANISM: Artificial Sequence
<220> FEATURE:
<223> OTHER INFORMATION: Synthetic construct

<400> SEQUENCE: 21
ccgtagctgg ccagtctggc cagtggatcg cccaaatttt gcggcgtatt gg            52

<210> SEQ ID NO 22
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (8)..(8)
<223> OTHER INFORMATION: Crosslinked derivative of alpha, alpha-
      disubstituted 5-carbon olefinic unnatural amino acid, crosslink to
      position 12
<220> FEATURE:
<221> NAME/KEY: MISC_FEATURE
<222> LOCATION: (12)..(12)
<223> OTHER INFORMATION: Crosslinked derivative of alpha, alpha-
      disubstituted 5-carbon olefinic unnatural amino acid, crosslink to
      position 8

<400> SEQUENCE: 22

Trp Val Ala Gln Trp Leu Arg Xaa Trp Gly Asp Xaa Phe Asn
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (8)..(8)
<223> OTHER INFORMATION: Crosslinked derivative of alpha, alpha-
      disubstituted 5-carbon olefinic unnatural amino acid, crosslink to
      position 12
<220> FEATURE:
<221> NAME/KEY: MISC_FEATURE
<222> LOCATION: (12)..(12)
<223> OTHER INFORMATION: Crosslinked derivative of alpha, alpha-
      disubstituted 5-carbon olefinic unnatural amino acid, crosslink to
      position 8

<400> SEQUENCE: 23

Trp Tyr Ala Gln Ile Leu Arg Xaa Met Gly Asp Xaa Phe Asn
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (8)..(8)
<223> OTHER INFORMATION: Crosslinked derivative of alpha, alpha-
      disubstituted 5-carbon olefinic unnatural amino acid, crosslink to
      position 12

```
<220> FEATURE:
<221> NAME/KEY: MISC_FEATURE
<222> LOCATION: (12)..(12)
<223> OTHER INFORMATION: Crosslinked derivative of alpha, alpha-
      disubstituted 5-carbon olefinic unnatural amino acid, crosslink to
      position 8

<400> SEQUENCE: 24

Trp Leu Ala Gln Leu Leu Arg Xaa Tyr Gly Asp Xaa Phe Asn
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (8)..(8)
<223> OTHER INFORMATION: Crosslinked derivative of alpha, alpha-
      disubstituted 5-carbon olefinic unnatural amino acid, crosslink to
      position 12
<220> FEATURE:
<221> NAME/KEY: MISC_FEATURE
<222> LOCATION: (12)..(12)
<223> OTHER INFORMATION: Crosslinked derivative of alpha, alpha-
      disubstituted 5-carbon olefinic unnatural amino acid, crosslink to
      position 8

<400> SEQUENCE: 25

Trp Ile Ala Gln Ile Leu Arg Xaa Trp Gly Asp Xaa Phe Asn
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (8)..(8)
<223> OTHER INFORMATION: Crosslinked derivative of alpha, alpha-
      disubstituted 5-carbon olefinic unnatural amino acid, crosslink to
      position 12
<220> FEATURE:
<221> NAME/KEY: MISC_FEATURE
<222> LOCATION: (12)..(12)
<223> OTHER INFORMATION: Crosslinked derivative of alpha, alpha-
      disubstituted 5-carbon olefinic unnatural amino acid, crosslink to
      position 8

<400> SEQUENCE: 26

Trp Val Ala Gln Thr Leu Arg Xaa Trp Gly Asp Xaa Phe Asn
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (8)..(8)
<223> OTHER INFORMATION: Crosslinked derivative of alpha, alpha-
      disubstituted 5-carbon olefinic unnatural amino acid, crosslink to
      position 12
<220> FEATURE:
<221> NAME/KEY: MISC_FEATURE
<222> LOCATION: (12)..(12)
<223> OTHER INFORMATION: Crosslinked derivative of alpha, alpha-
```

```
    disubstituted 5-carbon olefinic unnatural amino acid, crosslink to
    position 8

<400> SEQUENCE: 27

Trp Ile Ala Gln

```
Trp Leu Ala Gln Leu Leu Arg Xaa Ile Gly Asp Xaa Ile Asn
1               5                   10
```

<210> SEQ ID NO 31
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (8)..(8)
<223> OTHER INFORMATION: Crosslinked derivative of alpha, alpha-
      disubstituted 5-carbon olefinic unnatural amino acid, crosslink to
      position 12
<220> FEATURE:
<221> NAME/KEY: MISC_FEATURE
<222> LOCATION: (12)..(12)
<223> OTHER INFORMATION: Crosslinked derivative of alpha, alpha-
      disubstituted 5-carbon olefinic unnatural amino acid, crosslink to
      position 8

<400> SEQUENCE: 31

```
Trp Leu Ala Gln Glu Leu Arg Xaa Ile Gly Asp Xaa Val Asn
1               5                   10
```

<210> SEQ ID NO 32
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (5)..(5)
<223> OTHER INFORMATION: Xaa can be any amino acid
<220> FEATURE:
<221> NAME/KEY: misc_feature
<222> LOCATION: (8)..(8)
<223> OTHER INFORMATION: Xaa can be any amino acid
<220> FEATURE:
<221> NAME/KEY: misc_feature
<222> LOCATION: (9)..(9)
<223> OTHER INFORMATION: Xaa can be any amino acid
<220> FEATURE:
<221> NAME/KEY: misc_feature
<222> LOCATION: (12)..(12)
<223> OTHER INFORMATION: Xaa can be any amino acid
<220> FEATURE:
<221> NAME/KEY: misc_feature
<222> LOCATION: (13)..(13)
<223> OTHER INFORMATION: Xaa can be any amino acid

<400> SEQUENCE: 32

```
Trp Xaa Ala Gln Xaa Leu Arg Xaa Xaa Gly Asp Xaa Xaa Asn
1               5                   10
```

<210> SEQ ID NO 33
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa can be any amino acid
<220> FEATURE:
<221> NAME/KEY: misc_feature
<222> LOCATION: (12)..(12)
<223> OTHER INFORMATION: Xaa can be any amino acid

<400> SEQUENCE: 33

Trp Val Ala Gln Trp Leu Arg Xaa Trp Gly Asp Xaa Phe Asn
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa can be any amino acid
<220> FEATURE:
<221> NAME/KEY: misc_feature
<222> LOCATION: (12)..(12)
<223> OTHER INFORMATION: Xaa can be any amino acid

<400> SEQUENCE: 34

Trp Ile Ala Gln Ile Leu Arg Xaa Trp Gly Asp Xaa Phe Asn
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa can be any amino acid
<220> FEATURE:
<221> NAME/KEY: misc_feature
<222> LOCATION: (12)..(12)
<223> OTHER INFORMATION: Xaa can be any amino acid

<400> SEQUENCE: 35

Trp Val Ala Gln Thr Leu Arg Xaa Trp Gly Asp Xaa Phe Asn
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa can be any amino acid
<220> FEATURE:
<221> NAME/KEY: misc_feature
<222> LOCATION: (12)..(12)
<223> OTHER INFORMATION: Xaa can be any amino acid

<400> SEQUENCE: 36

Trp Ile Ala Gln Leu Leu Arg Xaa Ile Gly Asp Xaa Val Asn
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Synthetic construct
<220> FEATURE:

```
<221> NAME/KEY: misc_feature
<222> LOCATION: (8)..(8)
<223> OTHER INFORMATION: Xaa can be any amino acid
<220> FEATURE:
<221> NAME/KEY: misc_feature
<222> LOCATION: (12)..(12)
<223> OTHER INFORMATION: Xaa can be any amino acid

<400> SEQUENCE: 37

Trp Val Ala Gln Leu Leu Arg Xaa Ile Gly Asp Xaa Val Asn
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa can be any amino acid
<220> FEATURE:
<221> NAME/KEY: misc_feature
<222> LOCATION: (12)..(12)
<223> OTHER INFORMATION: Xaa can be any amino acid

<400> SEQUENCE: 38

Trp Met Ala Gln Ile Leu Arg Xaa Ile Gly Asp Xaa Val Asn
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa can be any amino acid
<220> FEATURE:
<221> NAME/KEY: misc_feature
<222> LOCATION: (12)..(12)
<223> OTHER INFORMATION: Xaa can be any amino acid

<400> SEQUENCE: 39

Trp Leu Ala Gln Leu Leu Arg Xaa Ile Gly Asp Xaa Ile Asn
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa can be any amino acid
<220> FEATURE:
<221> NAME/KEY: misc_feature
<222> LOCATION: (12)..(12)
<223> OTHER INFORMATION: Xaa can be any amino acid

<400> SEQUENCE: 40

Trp Leu Ala Gln Glu Leu Arg Xaa Ile Gly Asp Xaa Val Asn
1               5                   10

<210> SEQ ID NO 41
<211> LENGTH: 14
```

```
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa can be any amino acid
<220> FEATURE:
<221> NAME/KEY: misc_feature
<222> LOCATION: (12)..(12)
<223> OTHER INFORMATION: Xaa can be any amino acid

<400> SEQUENCE: 41

Trp Tyr Ala Gln Ile Leu Arg Xaa Met Gly Asp Xaa Phe Asn
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa can be any amino acid
<220> FEATURE:
<221> NAME/KEY: misc_feature
<222> LOCATION: (12)..(12)
<223> OTHER INFORMATION: Xaa can be any amino acid

<400> SEQUENCE: 42

Trp Leu Ala Gln Leu Leu Arg Xaa Tyr Gly Asp Xaa Phe Asn
1               5                   10
```

ENGINEERED POTENT CYTOTOXIC STAPLED BH3 PEPTIDES

CROSS REFERENCE TO RELATED APPLICATIONS

This application is a divisional of U.S. patent application Ser. No. 15/265,321, which was filed Sep. 14, 2016 and was a continuation of U.S. patent application Ser. No. 14/376,223, which was filed Aug. 1, 2014, issued as U.S. Pat. No. 9,464,125 on Oct. 11, 2016, and was a 35 USC § 371 national stage application of PCT/US2013/024617, which was filed Feb. 4, 2013 and claimed the benefit of U.S. Provisional Application No. 61/594,810, which was filed Feb. 3, 2012, all of which are incorporated herein by reference as if fully set forth.

This invention was made with government support under Grant No. CBET-0952875 awarded by the National Science Foundation. The government has certain rights in this invention.

The sequence listing electronically filed with this application, titled "Sequence Listing," created on Apr. 8, 2016, and having a file size of 16,750 bytes is incorporated herein by reference as if fully set forth.

FIELD OF INVENTION

The disclosure herein relates to cytotoxic stapled BH3 peptides.

BACKGROUND

The Bcl-2 family of proteins function at an important checkpoint in apoptosis, and can be considered as arbiters deciding whether a cell lives or dies. The pro-death Bcl-2 family members includes Bak and Bax, which induce permeabilization of the mitochondrial membrane, and a collection of "BH3-only" proteins, such as Bim, Bid, and Noxa, that play different roles in inducing apoptosis. The canonical function of pro-survival members of the Bcl-2 family, including Bcl-$x_L$, Bcl-2, Bcl-w, Mcl-1, and A1, is to antagonize apoptosis via heterodimeric interactions with the pro-death family members. Pro-survival Bcl-2 family members were identified as oncogenes, and these proteins are commonly overexpressed in human cancers as revealed by immunohistochemical and biochemical studies. Heterodimeric interactions between Bcl-2 family members are mediated by the helical amphipathic BH3 domain of the pro-death protein which binds to a surface cleft on the pro-survival protein.

One proposed therapeutic intervention in cancers focuses on inhibition of the heterodimeric interactions between family members via the binding of a BH3 peptide or a small molecule BH3 peptide mimic. Such inhibitors result in a decrease of sequestration of pro-death proteins by pro-survival proteins and restoration of apoptotic function to the cells. This strategy has been demonstrated successfully with several molecules including the small molecule ABT-737 and a conformationally constrained "stapled" BH3 peptide from the pro-death protein Bid, both of which exhibit cytotoxicity toward cancer cell lines and are able to reduce malignancies in xenograft models. Stapled peptides are helical peptides containing a sidechain-sidechain or backbone-sidechain crosslink that strongly biases the peptide toward a helical structure. Some classes of stapled peptides are able to cross cell membranes making them attractive as therapeutic lead molecules.

SUMMARY

In an aspect, the invention relates to a composition comprising an engineered cytotoxic stapled BH3 peptide including at least a fourteen amino acid sequence with at least 85% identity to the sequence Trp-Xaa-Ala-Gln-Xaa-Leu-Arg-Arg-Xaa-Gly-Asp-Glu-Xaa-Asn (SEQ ID NO: 1). Xaa is any amino acid. A crosslink from amino acid side chain to amino acid side chain or from amino acid side chain to peptide backbone is present within the fourteen amino acid sequence.

In an aspect, the invention relates to a method of treating a patient. The method comprises administering to a patient in need thereof a composition comprising an engineered cytotoxic stapled BH3 peptide including at least a fourteen amino acid sequence with at least 85% identity to the sequence Trp-Xaa-Ala-Gln-Xaa-Leu-Arg-Arg-Xaa-Gly-Asp-Glu-Xaa-Asn (SEQ ID NO: 1). Xaa is any amino acid. A crosslink from amino acid side chain to amino acid side chain or from amino acid side chain to peptide backbone is present within the fourteen amino acid.

In an aspect, the invention relates to a method of making an engineered cytotoxic stapled BH3 peptide. The method comprises constructing a library including at least one modified BH3 peptide comprising at least a fourteen amino acid sequence with at least 85% identity to the sequence Trp-Xaa-Ala-Gln-Xaa-Leu-Arg-Arg-Xaa-Gly-Asp-Glu-Xaa-Asn (SEQ ID NO: 1), wherein Xaa is any amino acid. The method also comprises screening the library for affinity of the at least one modified BH3 peptide toward a pro-survival Bcl-2 family protein, and selecting a modified BH3 peptide with affinity toward pro-survival Bcl-2 family proteins to obtain a selected modified BH3 peptide. The method further comprises synthesizing a stapled BH3 peptide having the sequence of the selected modified BH3 peptide and including a crosslink from amino acid side chain to amino acid side chain or from amino acid side chain to peptide backbone within the fourteen amino acid sequence. An amino acid in the crosslink may be the same as in the selected modified BH3 peptide or altered to include a cross-link moiety.

BRIEF DESCRIPTION OF THE DRAWINGS

The following detailed description of the preferred embodiment of the present invention will be better understood when read in conjunction with the appended drawings. For the purpose of illustrating the invention, there are shown in the drawings embodiments which are presently preferred. It is understood, however, that the invention is not limited to the precise arrangements and instrumentalities shown. In the drawings:

FIGS. 4A-4C illustrate that the M2-4 stapled peptide is taken up into and causes apoptosis in HeLa cells. In FIG. 4A, uptake of fluorescein-labeled M2-4 stapled peptide (Fl-M2-4) is illustrated. In FIG. 4B, the same field of view as FIG. 4A is illustrated, but stained for nuclei. In FIG. 4C a merged view of stapled peptide uptake and nuclei is illustrated.

FIGS. 4D-4F illustrate a TUNEL assay on cells treated with M2-4 stapled peptide. Red fluorescence indicates DNA fragmentation. In FIG. 4D, a TUNEL assay on cells treated with M2-4 stapled peptide is illustrated. In FIG. 4E, the same field of view as 4D is illustrated, but stained for nuclei. In FIG. 4F, a Merged view of DNA fragmentation staining and nuclear staining is illustrated. Scale bar is 20 µM.

FIG. 7AA illustrates apparent $K_d$ measurements of E151Q binding Mcl-1.

FIG. 7AB illustrates apparent $K_d$ measurements of X2-3 binding Mcl-1.

FIG. 7AC illustrates apparent $K_d$ measurements of X2-8 binding Mcl-1.

FIG. 7AD illustrates apparent $K_d$ measurements of M2-2 binding Mcl-1.

FIG. 7AE illustrates apparent $K_d$ measurements of M2-4 binding Mcl-1.

FIG. 7AF illustrates apparent $K_d$ measurements of E151Q binding A1.

FIG. 7AG illustrates apparent $K_d$ measurements of X2-3 binding A1.

FIG. 7AH illustrates apparent $K_d$ measurements of X2-8 binding A1.

FIG. 7AI illustrates apparent $K_d$ measurements of M2-2 binding A1.

FIG. 7AJ illustrates apparent $K_d$ measurements of M2-4 binding A1.

DETAILED DESCRIPTION OF THE PREFERRED EMBODIMENTS

Figure 1A:
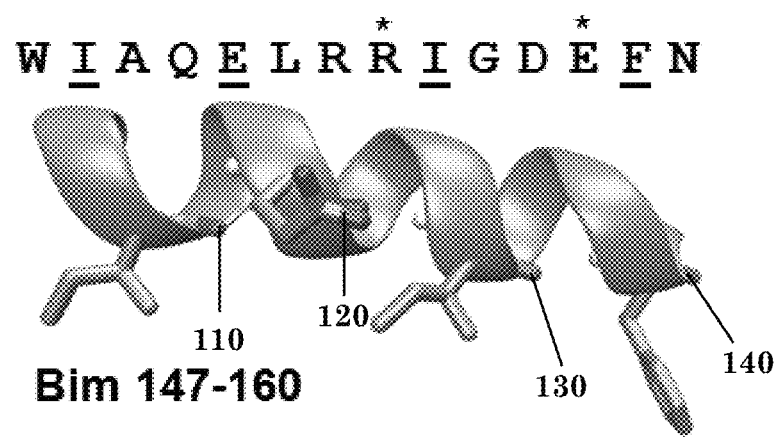
FIG. 1A illustrates the sequence (SEQ ID NO: 12) and structure of a 14 amino acid Bim BH3 peptide. The amino acids mutagenized in the library are underlined in the sequence. The amino acids labeled with an asterisk were replaced by olefinic amino acids in stapled peptide constructs. Coordinates to draw the peptide structure are from PDB file 2K7W.

Certain terminology is used in the following description for convenience only and is not limiting. The words "right," "left," "top," and "bottom" designate directions in the drawings to which reference is made. The words "a" and "one," as used in the claims and in the corresponding portions of the specification, are defined as including one or more of the referenced item unless specifically stated otherwise. The phrase "at least one" followed by a list of two or more items, such as A, B, or C, means any individual one of A, B, or C as well as any combination thereof.

Referring to FIG. 1A, the wild type Bim BH3 peptide is illustrated. The Bim BH3 peptide includes residues 147-160 of the Bim peptide. The fourteen amino acid sequence of the Bim BH3 peptide is WIAQELRRIGDEFN (SEQ ID NO. 12). Amino acids 110 (I148), 120 (E151), 130 (I155), and 140 (F159) were mutagenized to create a library of BH3 peptides. Amino acid positions for peptides in the library are referred to herein either by the original numbering from the Bim BH3 peptide (147-160), or by positions 1-14, where positions 1, 2, 3, 4, 5, 6, 7, 8, 9, 10, 11, 12, 13, and 14 correspond to positions 147, 148, 149, 150, 151, 152, 153, 154, 155, 156, 157, 158, 159, and 160, respectively, in the Bim BH3 peptide. Embodiments of engineered cytotoxic stapled BH3 peptides described herein and having at least a fourteen amino acid sequence are numbered with the same numbering scheme where positions 1, 2, 3, 4, 5, 6, 7, 8, 9, 10, 11, 12, 13, and 14 correspond to positions 147, 148, 149, 150, 151, 152, 153, 154, 155, 156, 157, 158, 159, and 160, respectively, in the Bim BH3 peptide.

Figure 1B:
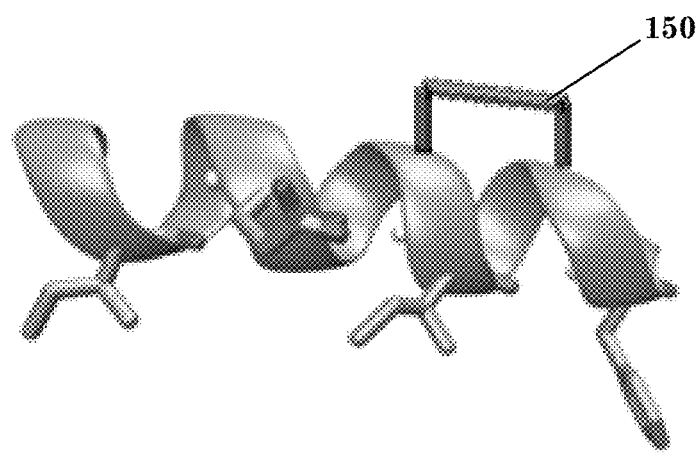
FIG. 1B illustrates the structure of a stapled 14 amino acid Bim BH3 peptide.

Referring to FIG. 1B, an engineered cytotoxic stapled BH3 peptide is illustrated having the sequence of the Bim BH3 peptide but for positions 8 and 12, which were replaced with an α, α-disubstituted 5-carbon olefinic unnatural amino acid and subjected to olefin ring closure. Bracket 150 represents the crosslink between positions 8 and 12 and formed by the olefin ring closure reaction. Further formulas herein utilize a bracket in a similar fashion to indicate a crosslink.

Embodiments include a composition comprising an engineered cytotoxic stapled BH3 peptide. The engineered cytotoxic stapled BH3 peptide may include at least a fourteen amino acid sequence with at least 42%, 50%, 57%, 64%, 71%, 78%, 85%, 92% or 100% identity to the sequence Trp-Xaa-Ala-Gln-Xaa-Leu-Arg-Arg-Xaa-Gly-Asp-Glu-Xaa-Asn (SEQ ID NO:1) along the length of the fourteen amino acid sequence. Xaa may be any amino acid. Determining percent identity of two amino acid sequences may include aligning and comparing the amino acid residues at corresponding positions in the two sequences. If all positions in two sequences are occupied by identical amino acid residues then the sequences are said to be 100% identical. Percent identity may be measured by the Smith Waterman algorithm (Smith T F, Waterman M S 1981 "Identification of Common Molecular Subsequences," J Mol Biol 147: 195-197, which is incorporated herein by reference as if fully set forth). Since Xaa can be any amino acid, a test sequence would match at that position regardless of the amino acid in the test sequence. The engineered cytotoxic stapled BH3 peptide may have fewer than fourteen residues of SEQ ID NO: 1. A shorter engineered cytotoxic stapled BH3 peptide may have 12 or 13 amino acids selected from any of the 12 or 13 contiguous amino acids of SEQ ID NO: 1. An engineered cytotoxic stapled BH3 peptide may include more than fourteen amino acids. The engineered cytotoxic stapled BH3 peptide may have 8 or less, 7 or less, 6 or less, 5 or less, 4 or less, 3 or less, 2 or less, 1 or less, or zero amino acid replacement in comparison to the sequence of SEQ ID NO. 1.

The replacement may be with any amino acid whether naturally occurring or synthetic. The replacement may be with an amino acid analog or amino acid mimetic that functions similarly to the naturally occurring amino acids. Naturally occurring amino acids are those encoded by the genetic code, as well as those amino acids that are later modified. The later modification may be but is not limited to hydroxyproline, γ-carboxyglutamate, and O-phosphoserine modifications. Naturally occurring amino acids include the standard 20, and unusual amino acids. Unusual amino acids include selenocysteine. The replacement may be with an amino acid analog, which refers to compounds that have the same basic chemical structure as a naturally occurring amino acid; e.g., an α carbon that is bound to a hydrogen, a carboxyl group, an amino group, and an R group. Examples of amino acid analogs include but are not limited to homoserine, norleucine, methionine sulfoxide, methionine methyl sulfonium. Such analogs may have modified R groups or modified peptide backbones. The amino acid analogs may retain the same basic chemical structure as a naturally occurring amino acid. The replacement may be with an amino acid mimetics, which refers to chemical compounds that have a structure that is different from the general chemical structure of an amino acid, but that functions similarly to a naturally occurring amino acid. The replacement may be with an α, α-disubstituted 5-carbon olefinic unnatural amino acid.

A replacement may be a conservative replacement, or a non-conservative replacement. A conservative replacement refers to a substitution of an amino acid with a chemically similar amino acid. Conservative substitution tables providing functionally similar amino acids are well known in the art. Such conservatively replacements include but are not limited to substitutions for one another: (1) Alanine (A), Glycine (G); (2) Aspartic acid (D), Glutamic acid (E); (3)

Asparagine (N), Glutamine (Q); (4) Arginine (R), Lysine (K); (5) Isoleucine (1), Leucine (L), Methionine (M), Valine (V); (6) Phenylalanine (F), Tyrosine (Y), Tryptophan (W); (7) Serine (S), Threonine (T); and (8) Cysteine (C), Methionine (M) (see, e.g., Creighton, Proteins (1984)). A replacement may be from one amino acid to another with a similar hydrophobicity, hydrophilicity, solubility, polarity, or acidity.

A sequence having less than 100% identity to the reference sequence Trp-Xaa-Ala-Gln-Xaa-Leu-Arg-Arg-Xaa-Gly-Asp-Glu-Xaa-Asn (SEQ ID NO:1) may be referred to as a variant. An embodiment includes a composition including an engineered cytotoxic stapled BH3 peptide having a sequence that is a variant of SEQ ID NO: 1. An embodiment includes a composition including an engineered cytotoxic stapled BH3 peptide having a sequence that is a variant of SEQ ID NO: 10 (Trp-Leu-Ala-Gln-Leu-Leu-Arg-Arg-Ile-Gly-Asp-Glu-Ile-Asn) and having at least 10% activity of a stapled BH3 peptide having the sequence of SEQ ID NO: 10. The activity may be determined by the MTT assay in Example 6.5.

In an embodiment, one or more amino acids residues are replaced with a residue having a crosslinking moiety. The engineered cytotoxic stapled BH3 peptide may include at least a fourteen amino acid sequence with the sequence Trp-Xaa-Ala-Gln-Xaa-Leu-Arg-Arg-Xaa-Gly-Asp-Glu-Xaa-Asn (SEQ ID NO:1), where two, one, or zero amino acid residues are replaced by a residue(s) having a cross linking moiety or are modified to include a cross-linking moiety. The engineered cytotoxic stapled BH3 peptide may include a crosslink from an amino acid side chain to another amino acid side chain within the fourteen amino acid sequence. The engineered cytotoxic stapled BH3 peptide may include a crosslink from an amino acid side chain to the peptide backbone within the fourteen amino acid sequence. The crosslink may be formed between an α, α-disubstituted olefinic unnatural amino acid replacing the residue at any position of the fourteen amino acid sequence and an α, α-disubstituted olefinic unnatural amino acid replacing the residue at any other position of the fourteen amino acid sequence. The crosslink may be formed between an α, α-disubstituted olefinic unnatural amino acid replacing the residue at any position of the fourteen amino acid sequence and an α, α-disubstituted olefinic unnatural amino acid replacing the residue at any other position of the fourteen amino acid sequence. Each α, α-disubstituted olefinic unnatural amino acid may have a number of carbons suitable to result in a crosslink that stabilizes a desired structure. The number may be 5 in each. The crosslink may be formed between an α, α-disubstituted 5-carbon olefinic unnatural amino acid replacing the Arg residue at position 8 of the fourteen amino acid sequence and an α, α-disubstituted 5-carbon olefinic unnatural amino acid replacing the Glu residue at position 12 of the fourteen amino acid sequence.

Xaa may be any amino acid. Xaa may be Val, Tyr, Leu, Thr, Trp, Phe, Ile, or Met.

The engineered cytotoxic stapled BH3 peptide may be but is not limited to being 14, 15, or 16 amino acids in length.

The engineered cytotoxic stapled BH3 peptide may have the sequence Trp-Val-Ala-Gln-Trp-Leu-Arg-Arg-Trp-Gly-Asp-Glu-Phe-Asn (SEQ ID NO: 2); Trp-Tyr-Ala-Gln-Ile-Leu-Arg-Arg-Met-Gly-Asp-Glu-Phe-Asn (SEQ ID NO:3); Trp-Leu-Ala-Gln-Leu-Leu-Arg-Arg-Tyr-Gly-Asp-Glu-Phe-Asn (SEQ ID NO: 4); Trp-Ile-Ala-Gln-Ile-Leu-Arg-Arg-Trp-Gly-Asp-Glu-Phe-Asn (SEQ ID NO: 5); Trp-Val-Ala-Gln-Thr-Leu-Arg-Arg-Trp-Gly-Asp-Glu-Phe-Asn (SEQ ID NO: 6); Trp-Ile-Ala-Gln-Leu-Leu-Arg-Arg-Ile-Gly-Asp-Glu-Val-Asn (SEQ ID NO: 7); Trp-Val-Ala-Gln-Leu-Leu-Arg-Arg-Ile-Gly-Asp-Glu-Val-Asn (SEQ ID NO: 8); Trp-Met-Ala-Gln-Ile-Leu-Arg-Arg-Ile-Gly-Asp-Glu-Val-Asn (SEQ ID NO: 9); Trp-Leu-Ala-Gln-Leu-Leu-Arg-Arg-Ile-Gly-Asp-Glu-Ile-Asn (SEQ ID NO: 10); or Trp-Leu-Ala-Gln-Glu-Leu-Arg-Arg-Ile-Gly-Asp-Glu-Val-Asn (SEQ ID NO: 11), where two, one or zero amino acid residues are replaced by residue(s) having a cross linking moiety or are modified to include a crosslinking moiety. Peptides having the sequence of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or SEQ ID NO: 11 are also referred to herein as X2-3, X2-5, X2-8, X2-9, X2-10, M2-1, M2-2, M2-3, M2-4 or M2-8, respectively.

The engineered cytotoxic stapled BH3 peptide may have the structure of

Formula I

Trp-Val-Ala-Gln-Trp-Leu-Arg-Arg-Trp-Gly-Asp-Glu-Phe-Asn
(SEQ ID NO: 2);

Formula II

Trp-Tyr-Ala-Gln-Ile-Leu-Arg-Arg-Met-Gly-Asp-Glu-Phe-Asn
(SEQ ID NO: 3);

Formula III

Trp-Leu-Ala-Gln-Leu-Leu-Arg-Arg-Tyr-Gly-Asp-Glu-Phe-Asn
(SEQ ID NO: 4);

Formula IV

Trp-Ile-Ala-Gln-Ile-Leu-Arg-Arg-Trp-Gly-Asp-Glu-Phe-Asn
(SEQ ID NO: 5);

Formula V

Trp-Val-Ala-Gln-Thr-Leu-Arg-Arg-Trp-Gly-Asp-Glu-Phe-Asn
(SEQ ID NO: 6);

Formula VI

Trp-Ile-Ala-Gln-Leu-Leu-Arg-Arg-Ile-Gly-Asp-Glu-Val-Asn
(SEQ ID NO: 7);

Formula VII

Trp-Val-Ala-Gln-Leu-Leu-Arg-Arg-Ile-Gly-Asp-Glu-Val-Asn
(SEQ ID NO: 8);

Formula VIII

Trp-Met-Ala-Gln-Ile-Leu-Arg-Arg-Ile-Gly-Asp-Glu-Val-Asn
(SEQ ID NO: 9);

Formula IX

Trp-Leu-Ala-Gln-Leu-Leu-Arg-Arg-Ile-Gly-Asp-Glu-Ile-Asn
(SEQ ID NO: 10); or

Formula X

Trp-Leu-Ala-Gln-Glu-Leu-Arg-Arg-Ile-Gly-Asp-Glu-Val-Asn
(SEQ ID NO: 11), wherein at least two, one, or zero amino acid residues are replaced with residue(s) having a crosslinking moiety or are modified to have a crosslinking moiety. The crosslink in any one of Formulas I-X may be formed between an α, α-disubstituted 5-carbon olefinic unnatural amino acid replacing the Arg residue at position 8 of the fourteen amino acid sequence and an α, α-disubstituted 5-carbon olefinic unnatural amino acid replacing the Glu residue at position 12 of the fourteen amino acid sequence.

The composition may also include one or more complementing therapeutic. Non-limiting examples of a complementing therapeutic are ABT-737 and ABT-199.

The composition may include a pharmaceutically acceptable carrier. The pharmaceutically acceptable carrier may include but is not limited to at least one of ion exchangers, alumina, aluminum stearate, lecithin, serum proteins, human serum albumin, buffer substances, phosphates, glycine, sorbic acid, potassium sorbate, partial glyceride mixtures of saturated vegetable fatty acids, water, salts, electrolytes, protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, waxes, polyethylene glycol, starch, lactose, dicalcium phosphate, microcrystalline cellulose, sucrose, dextrose, talc, magnesium carbonate, kaolin; non-ionic surfactants, edible oils, physiological saline, bacteriostatic water, Cremophor EL™ (BASF, Parsippany, N.J.), and phosphate buffered saline (PBS).

The composition may include at least two different engineered cytotoxic stapled BH3 peptides in combination. For example, the composition may include the cytotoxic stapled peptide of Formula I and the cytotoxic stapled peptide of Formula II.

Embodiments include a method of treating a patient. The method may include administering to a patient in need thereof a composition comprising an engineered cytotoxic stapled BH3 peptide. The engineered cytotoxic stapled BH3 peptide may be any engineered cytotoxic stapled BH3 peptide described herein. The engineered cytotoxic stapled BH3 peptide may be M2-2 having the structure of Formula VII or M2-4 having the structure of Formula IX. The composition may be any composition described herein.

Administering may include delivering a dose of 10 to 100 mg/kg/day of the engineered cytotoxic stapled BH3 peptide. The dose may be any value between 10 and 100 mg/kg/day. The dose may be any dose between and including any two integer values between 10 to 100 mg/kg/day. The dose may be 10, 15, 20, 25, 30, 35, 40, 45, 50, 55, 60, 65, 70, 75, 80, 85, 90, 95, or 100 mg/kg/day or any dose in a range between any two of the foregoing. Administering may include delivering any dose of a complementing therapeutic. The complementing therapeutic dose may be any 25 to 100 mg/kg/day. The complementing therapeutic dose may be any value between 25 and 100 mg/kg/day. The complementing therapeutic dose may be any dose between and including any two integer values between 25 and 100 mg/kg/day. The complementing therapeutic dose may be 10, 15, 20, 25, 30, 35, 40, 45, 50, 55, 60, 65, 70, 75, 80, 85, 90, 95, or 100 mg/kg/day or any dose in a range between any two of the foregoing. The complementing therapeutic may be any one or more of ABT-737 or ABT-199. The concentration of the engineered cytotoxic stapled BH3 peptide(s) and at least one complementing therapeutic in the composition may be set to deliver the daily dosage in a single administration, two point administrations, multiple point administrations, or continuous administration (e.g., introvenously or transdermally) over a period of time. The period may be one day. The period may be 1, 2, 4, 8, 12, or 24 hours or a time within a range between any two of these values.

A composition including an engineered cytotoxic stapled BH3 peptide may include any amount of the engineered cytotoxic stapled BH3 peptide. The amount may be that sufficient to deliver the dosage as set forth above in a suitable volume or sized delivery mode. When the dosage is split into multiple administrations throughout a time period, the amount in one volume or delivery mode may be the total dosage divided by the number of administrations throughout the time period. When present in a composition, the complementing therapeutic may be at any complementing therapeutic amount. Like the engineered cytotoxic stapled BH3 peptide, the complementing therapeutic amount may be tailored to deliver the right complementing therapeutic amount in the volume or delivery mode used for administration.

The patient may be an animal. The patient may be a mammal. The patient may be a human. The patient may be a cancer patient. The cancer patient may be a breast cancer patient, a cervix cancer patient or a prostate cancer patient.

The route for administering a composition or pharmaceutical composition may be by any route. The route of administration may be any one or more route including but not limited to oral, injection, topical, enteral, rectal, gastrointestinal, sublingual, sublabial, buccal, epidural, intracerebral, intracerebroventricular, intracisternal, epicutaneous, intradermal, subcutaneous, nasal, intravenous, intraarterial, intramuscular, intracardiac, intraosseous, intrathecal, intraperitoneal, intravesical, intravitreal, intracavernous, intravaginal, intrauterine, extra-amniotic, transderm al, intratumoral, and transmucosal.

Embodiments include a method of making an engineered cytotoxic stapled BH3 peptide. The method may include constructing a library including at least one modified BH3 peptide. The modified BH3 peptide may include at least a fourteen amino acid sequence with at least 42%, 50%, 57%, 64%, 71%, 78%, 85%, 92%, or 100% identity to the sequence Trp-Xaa-Ala-Gln-Xaa-Leu-Arg-Arg-Xaa-Gly-Asp-Glu-Xaa-Asn (SEQ ID NO: 1). Xaa may be any amino acid. Xaa may be Val, Tyr, Thr, Leu, Trp, Phe, Ile, or Met. The modified BH3 peptide may have an amino acid replacement at 8 or less, 7 or less, 6 or less, 5 or less, 4 or less, 3 or less, 2 or less, 1 or less, or zero positions in comparison to the sequence of SEQ ID NO: 1. The replacement(s) may be as described above.

The method may include screening the library for affinity of the at least one modified BH3 peptide toward a pro-survival Bcl-2 family protein. Screening the library for affinity may include exposing the library to the pro-survival Bcl-2 family protein under conditions effective for binding between a BH3 peptide and the Bcl-2 protein. A non-limiting example of conditions may be found in Example 6.3. The pro-survival Bcl-2 family protein may have a concentration lower than the $K_d$ of wild-type Bim peptide against the pro-survival Bcl-2 family protein. Affinity toward pro-survival Bcl-2 family proteins may include binding of the at least one modified BH3 peptide to the pro-survival Bcl-2 family protein at the concentration lower than the $K_d$ of wild-type Bim peptide against the pro-survival Bcl-2 family protein. The pro-survival Bcl-2 family protein may be Mcl-1. The concentration of the mcl-1 may be less than 37.7 nM. The concentration of the Mcl-1 may be between 1 nM and 15 nM. The pro-survival Bcl-2 family protein may be Bcl-$_{XL}$. The concentration of the Bcl-$_{XL}$ may be less than 251 nM. The concentration of the Bcl-$_{XL}$ may be between 1 nM and 20 nM. Screening may include subjecting the mixture of the library and the pro-survival Bcl-2 family to flow cytometry.

The method may include selecting a modified BH3 peptide with affinity toward pro-survival Bcl-2 family proteins to obtain a selected modified BH3 peptide. Selecting may include isolating the highest affinity members from the library based on the flow cytometry. Highest affinity members may be cells exhibiting the top percentile (the top 1% or less) in fluorescence.

The method may include synthesizing a stapled BH3 peptide having the sequence of the selected modified BH3 peptide. The stapled BH3 peptide may include a crosslink from an amino acid side chain to another amino acid side chain within the fourteen amino acid sequence. The stapled BH3 peptide may include a crosslink from an amino acid side chain to the peptide backbone within the fourteen amino acid sequence. The amino acid in the crosslink may be the same as in the selected modified BH3 peptide or altered to include a cross-link moiety. The crosslink may be formed between an α, α-disubstituted olefinic unnatural amino acid replacing the residue at any position of the fourteen amino acid sequence and an α, α-disubstituted olefinic unnatural amino acid replacing the residue at any other position of the fourteen amino acid sequence. The crosslink may be formed between an α, α-disubstituted 5-carbon olefinic unnatural amino acid replacing the residue at any position of the fourteen amino acid sequence and an α, α-disubstituted 5-carbon olefinic unnatural amino acid replacing the residue at any other position of the fourteen amino acid sequence. The crosslink may be formed between an α, α-disubstituted 5-carbon olefinic unnatural amino acid replacing the Arg residue at position 8 of the fourteen amino acid sequence and an α, α-disubstituted 5-carbon olefinic unnatural amino acid replacing the Glu residue at position 12 of the fourteen amino acid sequence. The crosslink between the α, α-disubstituted 5-carbon olefinic unnatural amino acids may be formed by olefin metathesis. Conditions for olefin metathesis may be as set forth in Example 6.4.

The method may include evaluating the cytotoxicity of the stapled BH3 peptide. Methods and conditions for evaluating the cytotoxicity of the stapled BH3 peptide may be set forth in Example 6.5.

An embodiment includes a peptide composition comprising a peptide consisting of, consisting essentially of, or comprising the sequence of any amino acid sequence herein. The peptide composition may include any complementing therapeutic herein. The peptide composition may include a pharmaceutically acceptable carrier. The peptide composition may be used in a method of treating cancer by administering the peptide composition to patient in need thereof. The dosage of peptide in the peptide composition for the method may be like that of the engineered cytotoxic stapled BH3 peptide in the method described above. The dosage of complementing therapeutic in the method may be like that of the complementing therapeutic in the method described above.

EMBODIMENTS

The following list includes particular embodiments of the present invention. The list, however, is not limiting and does not exclude alternate embodiments, as would be appreciated by one of ordinary skill in the art.

1. A composition comprising an engineered cytotoxic stapled BH3 peptide including at least a fourteen amino acid sequence with at least 85% identity to the sequence Trp-Xaa-Ala-Gln-Xaa-Leu-Arg-Arg-Xaa-Gly-Asp-Glu-Xaa-Asn (SEQ ID NO: 1), wherein Xaa is any amino acid and a crosslink from amino acid side chain to amino acid side chain or from amino acid side chain to peptide backbone is present within the fourteen amino acid sequence.

2. The composition of embodiment 1, wherein the crosslink is formed between an α, α-disubstituted 5-carbon olefinic unnatural amino acid replacing the Arg residue at position 8 of the fourteen amino acid sequence and an α, α-disubstituted 5-carbon olefinic unnatural amino acid replacing the Glu residue at position 12 of the fourteen amino acid sequence.

3. The composition of any one or more of embodiments 1-2, wherein the engineered cytotoxic stapled BH3 peptide is 14, 15, or 16 amino acids in length.

4. The composition of any one or more of embodiments 1-3, wherein the engineered cytotoxic stapled BH3 peptide has the sequence Trp-Val-Ala-Gln-Trp-Leu-Arg-Arg-Trp-Gly-Asp-Glu-Phe-Asn (SEQ ID NO: 2); Trp-Tyr-Ala-Gln-Ile-Leu-Arg-Arg-Met-Gly-Asp-Glu-Phe-Asn (SEQ ID NO: 3); Trp-Leu-Ala-Gln-Leu-Leu-Arg-Arg-Tyr-Gly-Asp-Glu-Phe-Asn (SEQ ID NO: 4); Trp-Ile-Ala-Gln-Ile-Leu-Arg-Arg-Trp-Gly-Asp-Glu-Phe-Asn (SEQ ID NO: 5); Trp-Val-Ala-Gln-Thr-Leu-Arg-Arg-Trp-Gly-Asp-Glu-Phe-Asn (SEQ ID NO: 6); Trp-Ile-Ala-Gln-Leu-Leu-Arg-Arg-Ile-Gly-Asp-Glu-Val-Asn (SEQ ID NO: 7); Trp-Val-Ala-Gln-Leu-Leu-Arg-Arg-Ile-Gly-Asp-Glu-Val-Asn (SEQ ID NO: 8); Trp-Met-Ala-Gln-Ile-Leu-Arg-Arg-Ile-Gly-Asp-Glu-Val-Asn (SEQ ID NO: 9); Trp-Leu-Ala-Gln-Leu-Leu-Arg-Arg-Ile-Gly-Asp-Glu-Ile-Asn (SEQ ID NO: 10); or Trp-Leu-Ala-Gln-Glu-Leu-Arg-Arg-Ile-Gly-Asp-Glu-Val-Asn (SEQ ID NO: 11).

5. The composition of any one or more of embodiments 1-3, wherein the engineered cytotoxic stapled BH3 peptide has the structure of Formula I Trp-Val-Ala-Gln-Trp-Leu-Arg- Arg-Trp-Gly-Asp-Glu-Phe-Asn (SEQ ID NO: 2);

Formula II

Trp-Tyr-Ala-Gln-Ile-Leu-Arg-

Arg-Met-Gly-Asp-Glu-Phe-Asn (SEQ ID NO: 3);

Formula III

Trp-Leu-Ala-Gln-Leu-Leu-Arg-

Arg-Tyr-Gly-Asp-Glu-Phe-Asn (SEQ ID NO: 4);

Formula IV

Trp-Ile-Ala-Gln-Ile-Leu-Arg-

Arg-Trp-Gly-Asp-Glu-Phe-Asn (SEQ ID NO: 5);

Formula V

Trp-Val-Ala-Gln-Thr-Leu-Arg-

Arg-Trp-Gly-Asp-Glu-Phe-Asn (SEQ ID NO: 6);

Formula VI

Trp-Ile-Ala-Gln-Leu-Leu-Arg-

Arg-Ile-Gly-Asp-Glu-Val-Asn (SEQ ID NO: 7);

Formula VII

Trp-Met-Ala-Gln-Leu-Leu-Arg-

Arg-Ile-Gly-Asp-Glu-Val-Asn (SEQ ID NO: 8);

-continued

Formula VIII

Trp-Met-Ala-Gln-Ile-Leu-Arg-⌐ ¬
Arg-Ile-Gly-Asp-Glu-Val-Asn (SEQ ID NO: 9);

Formula IX

Trp-Leu-Ala-Gln-Leu-Leu-Arg-⌐ ¬
Arg-Ile-Gly-Asp-Glu-Ile-Asn (SEQ ID NO: 10); or

Formula X

Trp-Leu-Ala-Gln-Glu-Leu-Arg-⌐ ¬
Arg-Ile-Gly-Asp-Glu-Val-Asn (SEQ ID NO: 11), wherein the crosslink is formed between the Arg residue at position 8 of the fourteen amino acid sequence or a replacement thereof and the Glu residue at position 12 of the fourteen amino acid sequence or a replacement thereof.

6. The composition of any one or more of embodiments 1-3, wherein the engineered cytotoxic stapled BH3 peptide has the structure of Formula I Trp-Val-Ala-Gln-Trp-Leu-Arg-Arg-Trp-Gly-Asp-Glu-Phe-Asn (SEQ ID NO: 2);

Formula II

Trp-Tyr-Ala-Gln-Ile-Leu-Arg-Arg-Met-Gly-Asp-Glu-Phe-Asn (SEQ ID NO: 3);

Formula III

Trp-Leu-Ala-Gln-Leu-Leu-Arg-Arg-Tyr-Gly-Asp-Glu-Phe-Asn (SEQ ID NO: 4);

Formula IV

Trp-Ile-Ala-Gln-Ile-Leu-Arg-Arg-Trp-Gly-Asp-Glu-Phe-Asn (SEQ ID NO: 5);

Formula V

Trp-Val-Ala-Gln-Thr-Leu-Arg-Arg-Trp-Gly-Asp-Glu-Phe-Asn (SEQ ID NO: 6);

Formula VI

Trp-Ile-Ala-Gln-Leu-Leu-Arg-Arg-Ile-Gly-Asp-Glu-Val-Asn (SEQ ID NO: 7);

Formula VII

Trp-Val-Ala-Gln-Leu-Leu-Arg-Arg-Ile-Gly-Asp-Glu-Val-Asn (SEQ ID NO: 8);

Formula VIII

Trp-Met-Ala-Gln-Ile-Leu-Arg-Arg-Ile-Gly-Asp-Glu-Val-Asn (SEQ ID NO: 9);

Formula IX

Trp-Leu-Ala-Gln-Leu-Leu-Arg-Arg-Ile-Gly-Asp-Glu-Ile-Asn   or
(SEQ ID NO: 10);

Formula X

Trp-Leu-Ala-Gln-Glu-Leu-Arg-Arg-Ile-Gly-Asp-Glu-Val-Asn (SEQ ID NO: 11), wherein the crosslink is formed between an α, α-disubstituted 5-carbon olefinic unnatural amino acid replacing the Arg residue at position 8 of the fourteen amino acid sequence and an α, α-disubstituted 5-carbon olefinic unnatural amino acid replacing the Glu residue at position 12 of the fourteen amino acid sequence.

7. The composition of any one or more of embodiments 1-6 further comprising at least one of ABT-737 or ABT-199.

8. The composition of any one or more of embodiments 1-7 further comprising at least two different engineered cytotoxic stapled BH3 peptides in combination.

9. The composition of any one or more of embodiments 1-8 further comprising a pharmaceutically acceptable carrier.

10. The composition of embodiment 9, wherein the pharmaceutically acceptable carrier includes at least one substance selected from the group consisting of ion exchangers; alumina; aluminum stearate; lecithin; serum proteins; human serum albumin; buffer substances; phosphates; glycine; sorbic acid; potassium sorbate; partial glyceride mixtures of saturated vegetable fatty acids; water; salts; electrolytes; protamine sulfate; disodium hydrogen phosphate; potassium hydrogen phosphate; sodium chloride; zinc salts; colloidal silica; magnesium trisilicate; polyvinyl pyrrolidone; cellulose-based substances; polyethylene glycol; sodium carboxymethylcellulose; waxes; polyethylene glycol; starch; lactose; dicalcium phosphate; microcrystalline cellulose; sucrose; dextrose; talc; magnesium carbonate; kaolin; non-ionic surfactants; edible oils; physiological saline; bacteriostatic water; Cremophor EL™ (BASF, Parsippany, N.J.); and phosphate buffered saline (PBS).

11. A method of treating a patient comprising administering to a patient in need thereof the composition of any one or more of embodiments 1-10.

12. The method of embodiment 11, wherein the patient is an animal.

13. The method of embodiment 11, wherein the patient is a mammal.

14. The method of embodiment 11, wherein the patient is a human.

15. The method of any one or more of embodiments 11-14, wherein the patient is a cancer patient.

16. The method of any one or more of embodiments 11-15, wherein the cancer patient is a breast cancer patient, a cervix cancer patient or a prostate cancer patient.

17. The method of any one or more of embodiments 11-16, wherein the route of administration is selected from one or more of oral, injection, topical, enteral, rectal, gastrointestinal, sublingual, sublabial, buccal, epidural, intracerebral, intracerebroventricular, intracisternal, epicutaneous, intradermal, subcutaneous, nasal, intravenous, intraarterial, intramuscular, intracardiac, intraosseous, intrathecal, intraperitoneal, intravesical, intravitreal, intracavernous, intravaginal, intrauterine, extra-amniotic, transdermal, transdermal patch, intratumoral, oral, oral tablet, controlled release pellet, and transmucosal.

18. The method of any one or more of embodiments 15-31, wherein the composition is administered to deliver a dose of 10 to 100 mg/kg/day of the engineered cytotoxic stapled BH3 peptide.

19. The method of any one or more of embodiments 11-18, wherein the composition is administered to deliver a dose of 25 to 100 mg/kg/day of ABT-737 or a dose of 25 to 100 mg/kg/day of ABT-199.

20. A method of making an engineered cytotoxic stapled BH3 peptide comprising:

constructing a library including at least one modified BH3 peptide including at least a fourteen amino acid sequence with at least 85% identity to the sequence Trp-Xaa-Ala-Gln-Xaa-Leu-Arg-Arg-Xaa-Gly-Asp-Glu-Xaa-Asn (SEQ ID NO: 1), wherein Xaa is any amino acid;

screening the library for affinity of the at least one modified BH3 peptide toward a pro-survival Bcl-2 family protein;

selecting a modified BH3 peptide with affinity toward pro-survival Bcl-2 family proteins to obtain a selected modified BH3 peptide; and synthesizing a stapled BH3 peptide having the sequence of the selected modified BH3 peptide and including a crosslink from amino acid side chain to amino acid side chain or from amino acid side chain to peptide backbone within the fourteen amino acid sequence, wherein the amino acid in the crosslink may be the same as in the selected modified BH3 peptide or altered to include a cross-link moiety.

21. The method of embodiment 20 further comprising evaluating the cytotoxicity of the stapled BH3 peptide.

22. The method of any one or more of embodiments 20-21, wherein the crosslink is formed between an α, α-disubstituted 5-carbon olefinic unnatural amino acid replacing the Arg residue at position 8 of the fourteen amino acid sequence and an α, α-disubstituted 5-carbon olefinic unnatural amino acid replacing the Glu residue at position 12 of the fourteen amino acid sequence.

23. The method of any one or more of embodiments 20-22, wherein the crosslink is formed by olefin metathesis.

24. The method of any one or more of embodiments 20-23 wherein screening the library for affinity includes exposing the library to a pro-survival Bcl-2 family protein under conditions effective for binding of a wild type Bim BH3 peptide to the pro-survival Bcl-2 family protein.

25. The method of embodiment 24, wherein the pro-survival Bcl-2 family protein has a concentration lower than the $K_d$ of wild-type Bim peptide against the pro-survival Bcl-2 family protein.

26. The method of any one or more of embodiments 24-25, wherein affinity toward pro-survival Bcl-2 family proteins includes binding of the at least one modified BH3 peptide to the pro-survival Bcl-2 family protein at the concentration lower than the $K_d$ of wild-type Bim peptide against the pro-survival Bcl-2 family protein.

27. The method of any one or more of embodiments 24-26 wherein the pro-survival Bcl-2 family protein is Mcl-1.

28. The method of embodiment 27, wherein the concentration of the Mcl-1 is less than 37.7 nM.

29. The method of embodiment 27, wherein the concentration of the Mcl-1 is between 1 nM and 15 nM.

30. The method of any one or more of embodiments 24-26, wherein the pro-survival Bcl-2 family protein is Bcl-$x_L$.

31. The method of embodiment 30, wherein the concentration of the Bcl-$x_L$ is less than 251 nM.

32. The method of embodiment 30, wherein the concentration of the Bcl-$x_L$ is between 1 nM and 20 nM.

33. The method of any one or more of embodiments 20-32, wherein screening includes subjecting the mixture of the library and the pro-survival Bcl-2 family protein to flow cytometry and isolating the highest affinity members from the library.

34. The method of embodiment 33, wherein the highest affinity is the top 1% of cells exhibiting fluorescence.

35. A composition comprising the product of any one or more of embodiments 20-34.

Further embodiments herein may be formed by supplementing an embodiment with one or more element from any one or more other embodiment herein, and/or substituting one or more element from one embodiment with one or more element from one or more other embodiment herein.

EXAMPLES

The following non-limiting examples are provided to illustrate particular embodiments. The embodiments throughout may be supplemented with one or more detail from one or more example below, and/or one or more element from an embodiment may be substituted with one or more detail from one or more example below.

Example 1—Affinity Maturation of Bim BH3 Peptides

Binding between the rival pro-death and pro-survival factions of the Bcl-2 family of proteins is mediated by the helical, ampiphilic BH3 domain of the pro-death protein. A promising therapeutic intervention in many cancers involves the inhibition of these protein-protein interactions using small molecule BH3 mimetics or conformationally constrained ("stapled") peptides corresponding to the BH3 domain. As disclosed herein, the affinity of a BH3 peptide for its pro-survival protein targets correlates with its cytotoxicity against cancer cells. Using saturation mutagenesis, a 14 amino acid BH3 peptide from the pro-death protein Bim was affinity matured toward the pro-survival proteins Bcl-$x_L$ and Mcl-1 using bacterial cell surface display. The best variants from these screens bound their pro-survival targets with apparent $K_d$ values below 10 nM. Several affinity matured Bim BH3 variants were synthesized as stapled peptides and evaluated for cytotoxicity against human cancer cell lines derived from breast, cervix and prostate. A charge-neutral pseudo-wild-type peptide exhibits only modest cytotoxicity against these cell lines. In contrast, Bim variants that were affinity matured toward Mcl-1 exhibit potent cytotoxicity with single micromolar values of $IC_{50}$ against all four cell lines, with some $IC_{50}$ values as low as 1 μM. The most potent peptide isolated from the screen retains the promiscuous binding profile of the wild-type Bim peptide in addition to improved binding toward Mcl-1. Whereas studies on stapled BH3 peptides to date have focused on the cytotoxicity of these peptides toward hematopoietic neoplasms (leukemia, myeloma), the engineered stapled BH3 peptides herein have potent activity against other cancer types in culture. The engineering of a Bim BH3 peptide for increased affinity to Mcl-1 is a straightforward, rapid method for increasing its cytotoxicity toward multiple cancer cell lines.

The hypothesis that an increase in affinity of a BH3 peptide for its pro-survival target(s) correlates with an increase in the cytotoxicity of the peptide was tested. In this way, combinatorial protein engineering can be applied in a straightforward manner to the design of new cancer therapeutics. E. coli surface display technology and flow cytometric screening was used to affinity mature a 16 a BH3 peptide from the pro-death protein Bak toward multiple pro-survival targets (Sun et al., J. Mol. Biol, 2009 [18]; Zhang et al., ACS Synth. Biol, 2012 [19], which are incorporated herein by reference as if fully set forth. However, in a survey of all 16-mer BH3 peptides in the human genome, it was found that the BH3 peptide from the protein Bim exhibits promiscuous, avid (sub-micromolar apparent $K_d$) binding to all five pro-survival proteins (Zhang et al., Integr. Biol., 2011 [20], which is incorporated herein by reference as if fully set forth). A truncation study further illustrated that strong binding to all five proteins was maintained even with a minimal 14-mer Bim peptide (Zhang et al., Integr. Biol., 2011 [20], which is incorporated herein by reference as if fully set forth). Thus, the 14-mer Bim BH3 peptide (FIG. 1A) was chosen as the starting point for affinity maturation in this study. A panel of affinity matured Bim BH3 variants were synthesized as stapled peptides and evaluated for cytotoxicity against four cancer cell lines. It was found that while the wild-type Bim 14-mer stapled peptide exhibits no cytotoxicity, stapled Bim peptides that are affinity matured toward the pro-survival protein Mcl-1 exhibit potent cytotoxicity to multiple cancer cell lines with $IC_{50}$ values as low as 1 µM.

Figure 12:
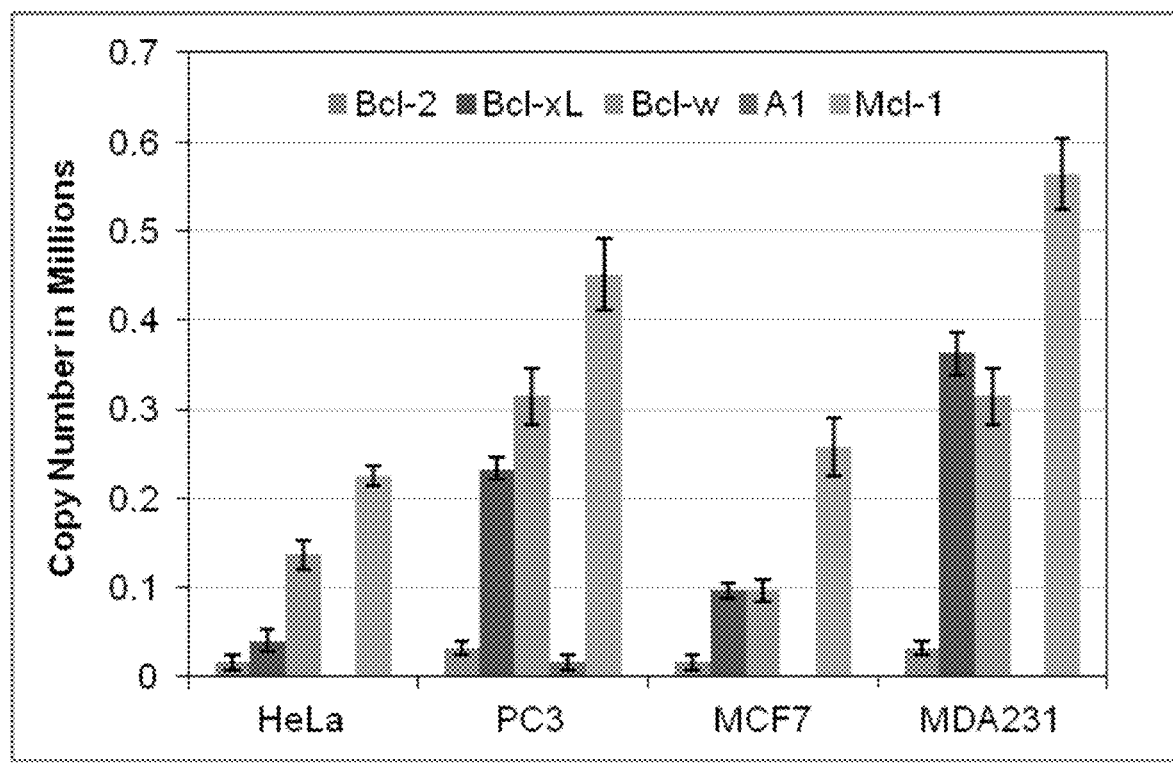
FIG. 12 illustrates gene expression data of five pro-survival Bcl-2 family proteins in HeLa, PC3, MCF7 and MDA231 cells, data reproduced from Placzek et al., 2010 [7]. In each panel, the five pro-survival Bcl-2 family proteins are Bcl-2, Bcl-$_{XL}$, Bcl-w, A1, and Mcl-1, from left to right.

It was found that affinity maturation of a minimal Bim BH3 peptide toward the pro-survival protein Mcl-1 is a simple and effective strategy for increasing the cytotoxicity of the peptide toward multiple cancer cell lines. Whereas a charge-neutral pseudo-wild-type Bim peptide has only modest cytotoxicity against the four cancer cell lines tested here, simply "tuning up" this peptide to improve its binding results in a dramatic increase in cytotoxicity. In a comprehensive qPCR study of a large panel of cancer cell lines, Placzek et al. found that Mcl-1 is frequently the most highly expressed of the pro-survival Bcl-2 family genes, including in all four of the cell lines studied here (FIG. 12) (Placzek et al., Cell Death Dis, 2010 [7], which is incorporated herein by reference as if fully set forth). Along the same lines, several studies have demonstrated that degradation or inhibition of Mcl-1 is a critical aspect of apoptosis (Chen et al., Mol. Cell., 2005 [25]; Quinn et al., Expert Opin. Inv. Drug., 2011 [27]; Chen et al., Cancer Res, 2007 [28]; Lee et al., J. Cell Biol., 2008 [29]; and van Delft et al., Cancer Cell, 2006 [30], which are incorporated herein by reference as if fully set forth). The increased cytotoxicity observed in the Mcl-1 matured peptides here is likely due to the fact that these peptides are more effective inhibitors of Mcl-1 than the pseudo-wild-type peptide. A longer stapled Bim peptide has been shown to serve as a direct activator of Bax (Gavathiotis et al., Nature, 2008 [31], which is incorporated herein by reference as if fully set forth), and the same hydrophobic residues in the Bim peptide that dictate binding to pro-survival proteins are also important for binding to Bax. The possibility that affinity matured Bim peptides are directly engaging Bax more effectively than the pseudo-wild-type peptide cannot be excluded.

Figure 3A:
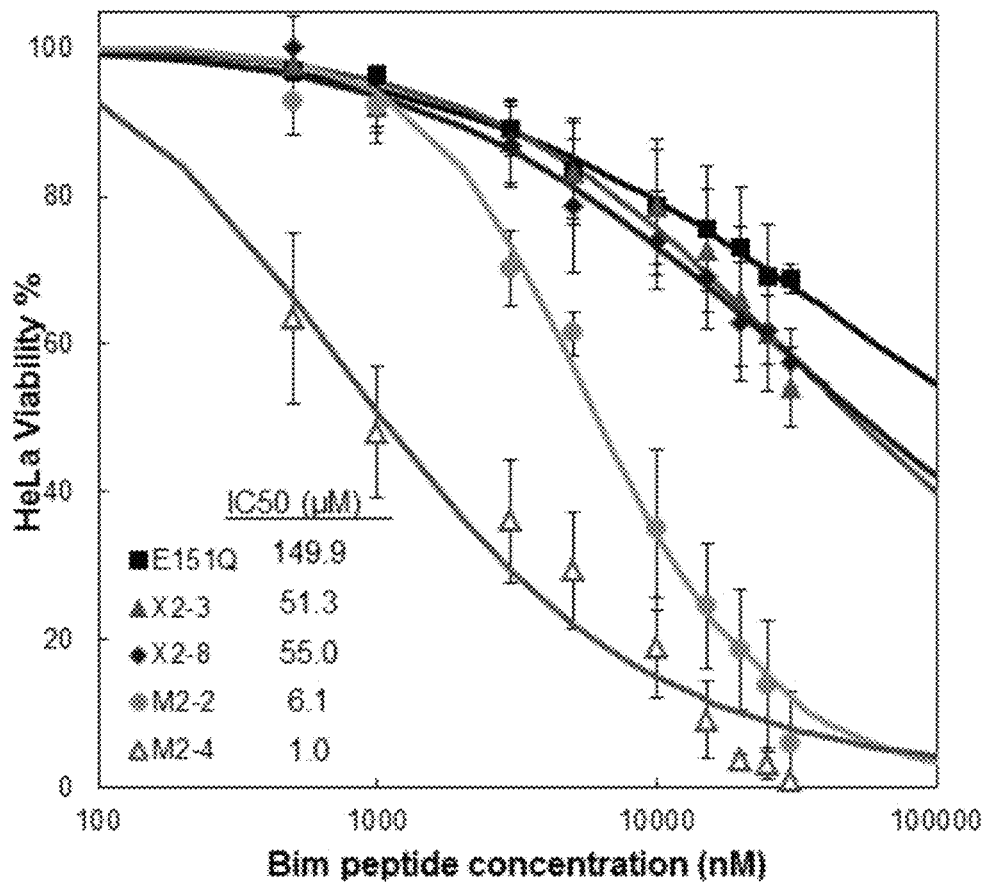
FIG. 3A illustrates cytotoxicity of pseudo-wild-type and affinity matured Bim BH3 peptides toward HeLa cells. Error bars represent the standard deviation from three biological replicates.
Figure 3B:
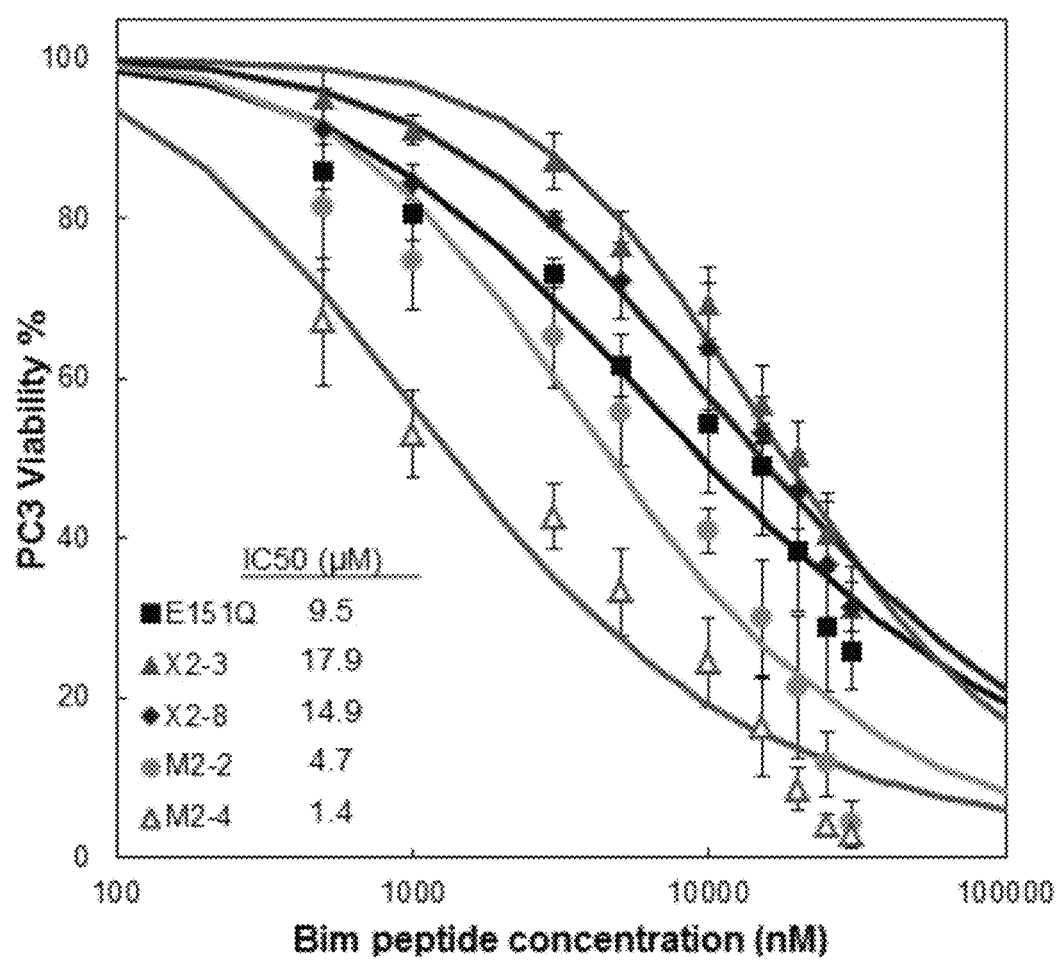
FIG. 3B illustrates cytotoxicity of pseudo-wild-type and affinity matured Bim BH3 peptides toward PC3 cells. Error bars represent the standard deviation from three biological replicates.

The two Bim peptides that were matured toward Mcl-1, M2-2 and M2-4, show impressive cytotoxicity as single agents, even comparing favorably to currently used chemotherapeutic agents such as cisplatin (see Table 1 below) (Li et al., Nat. Med., 2010 [32]; Basma et al., J. Biomed. Sci., 2005 [33]; Takara et al., Cancer Chemother. Pharmacol., 2006 [34]; and Dowling et al., Lett. Drug Des. Discov., 2008 [35], which are incorporated herein by reference as if fully set forth). The M2-2 and M2-4 peptides differ with regards to their spectrum of binding to pro-survival proteins; M2-2 has specificity toward only Mcl-1 and A1 whereas M2-4 retains the promiscuous binding profile of the parent wild-type Bim peptide. Of particular note is that the M2-2 and M2-4 peptides exhibit similar values of $IC_{50}$ toward the breast cancer lines MCF7 and MDA-MB-231 (FIGS. 3C-3D) suggesting that only tight binding toward Mcl-1 and A1 is required for cytotoxicity against these cell lines. In the case of the HeLa and PC3 cell lines, the pan-Bcl-2 inhibitor peptide M2-4 is more cytotoxic than the specific peptide M2-2 (FIGS. 3A-3B). This differential behavior between cell lines underscores the importance of developing therapeutics that complements each other. For example, a therapy that combined ABT-737 and the M2-2 peptide engineered here should be able to effectively neutralize all of the pro-survival Bcl-2 members. Since Mcl-1 knockdown (using antisense oligonucleotides) has been shown to sensitize cell lines and xenograft models to currently employed chemotherapeutic agents (Thallinger et al., Clin. Cancer Res., 2004 [36]; Thallinger et al., J. Invest. Dermatol., 2003 [37]; and Hussain et al., Clin. Cancer Res., 2007 [38], which are incorporated herein by reference as if fully set forth), the M2-2 and M2-4 peptides may be particularly useful as a component in combination therapies. Also of note is that the 14-mer stapled peptides employed here are significantly shorter than previously described stapled peptides developed for therapeutic uses (Walensky et al., Science, 2004 [13]; and Stewart et al., Nat. Chem. Biol., 2010 [23], which are incorporated herein by reference as if fully set forth). The smaller size of these peptides has several practical advantages including lower costs of production, lower dosing requirements, and potentially improved pharmacological properties. In summary, the results here demonstrate that affinity maturation of a minimal Bim BH3 peptide toward Mcl-1 is a simple, rapid strategy for improving the cytotoxicity of the stapled version of this peptide toward diverse cancer cell lines.

$IC_{50}$ values of cisplatin in different cancer cell lines, values for cisplatin from reference 33-36, and values for peptide M2-4 from this study are listed in Table 1, below.

TABLE 1

| $IC_{50}$ (µM) | HeLa | PC3 | MCF7 | MDA231 |
| --- | --- | --- | --- | --- |
| Cisplatin | 1.34 | 5.6 | 5 | ~10 |
| M2-4 | 1.04 | 1.36 | 5.72 | 4.39 |

Example 2—Library Construction from a Minimal Bim BH3 Peptide

The hydrophobic face of the Bim BH3 helix includes four residues, I148, L152, I155, and F159 (FIG. 1A). Leucine residues are strongly conserved in the $2^{nd}$ hydrophobic position of BH3 peptides (Zhang et al., Integr. Biol., 2011 [20], which is incorporated herein by reference as if fully set forth), and substitution of this leucine often dramatically decreases the binding affinity of the BH3 peptide for its target (Sattler et al., Science, 1997 [4], which is incorporated herein by reference as if fully set forth). Thus, 3 of the 4 hydrophobic face residues (I148, I155, and F159) were selected for randomization. A fourth residue, E151, was selected for randomization as well. This position was selected in view of the eventual goal of generating stapled peptides from the affinity matured sequences. The net charge of the wild-type Bim 14-mer is −1, and negative charge on a stapled peptide is expected to retard its cell uptake (Kim et al., Nat. Protoc., 2011 [21]; Bernal et al., J. Am. Chem. Soc., 2007 [22], which are incorporated herein by reference as if fully set forth). In a previous study, the two olefinic amino acids that generate the staple were placed at the R154 and E158 positions on the polar face of the Bim helix (Stewart et al., Nat. Chem. Biol., 2010 [23], which is incorporated herein by reference as if fully set forth). Adding this modification to the Bim 14-mer would leave three charged residues (E151, R153, and D157) in the peptide with an overall charge of −1. Indeed, tests with several different cancer cell lines showed that a wild-type Bim 14-mer stapled between R154 and E158 had no cytotoxicity (FIGS. 5A-5D), which may be attributable to an inability to be taken up by cells (Bernal et al., J. Am. Chem. Soc., 2007 [22], which is incorporated herein by reference as if fully set forth). E151 was chosen for randomization with the hope that it would be replaced by an uncharged residue during affinity maturation and bring the overall charge of the peptide to neutral. The 14-mer Bim library was created by fusing genes for Bim variants carrying NNK degenerate codons at the positions to be randomized to the 5' end of the gene for enhanced circularly permuted OmpX (eCPX) (Rice and Daugherty, Protein Eng. Des. Sel., 2008 [24], which is incorporated herein by reference as if fully set forth). After transforming the library into MC1061 *E. coli* cells, the library size was 4.5 million, covering 99% of the theoretical diversity of the library ($32^4$).

Example 3—Library Screening and Affinity Maturation

Bcl-$x_L$ and Mcl-1 were chosen as targets for the affinity maturation of the Bim 14-mer. Both Bcl-$x_L$ and Mcl-1 are present in high levels among a wide range of cancer cells (Placzek et al., Cell Death Dis., 2010 [7], which is incorporated herein by reference as if fully set forth). These two proteins also represent the two "subclasses" of the pro-survival Bcl-2 family proteins. Bcl-$x_L$ is representative of the Bcl-$x_L$, Bcl-2 and Bcl-w subclass, and Mcl-1 is representative of the Mcl-1 and A1 subclass. Some pro-death BH3-only proteins such as Bad only bind well to Bcl-$x_L$, Bcl-2 and Bcl-w, while others such as Noxa prefer binding to Mcl-1 and A1 (Chen et al., Mol. Cell, 2005 [25], which is incorporated herein by reference as if fully set forth). The small molecule BH3 mimetic ABT-737 also preferentially binds to the Bcl-$x_L$ subclass with only weak binding to Mcl-1 and A1 (Oltersdorf et al., Nature, 2005 [12], which is incorporated herein by reference as if fully set forth). By targeting the two subclasses of pro-survival proteins, the inventors set out to find a peptide therapeutic with cytotoxicity toward a wide spectrum of cancer cell lines.

Figure 6A:
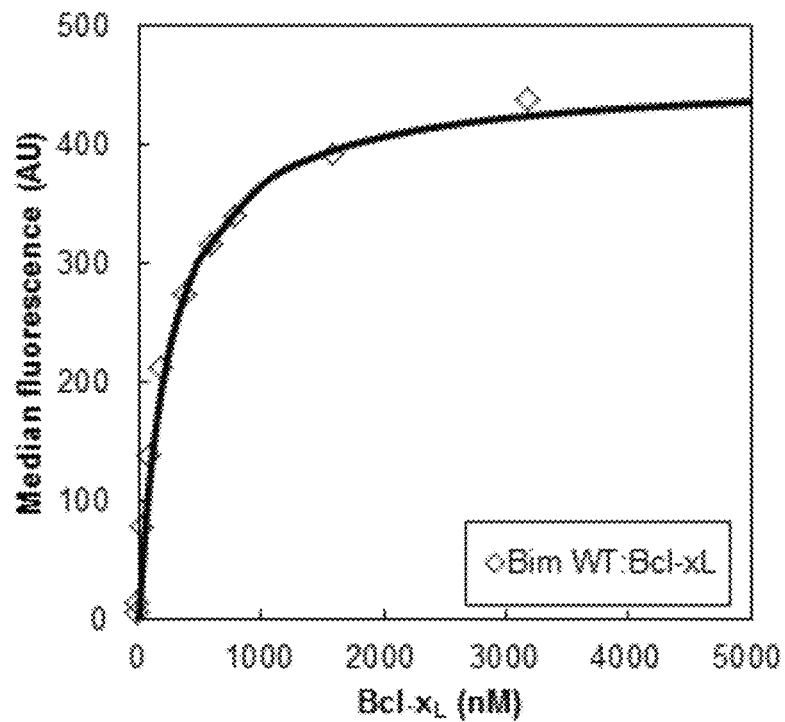
FIG. 6A illustrates apparent $K_d$ measurements of wild-type Bim peptide against Bcl-$_{XL}$.
Figure 6B:
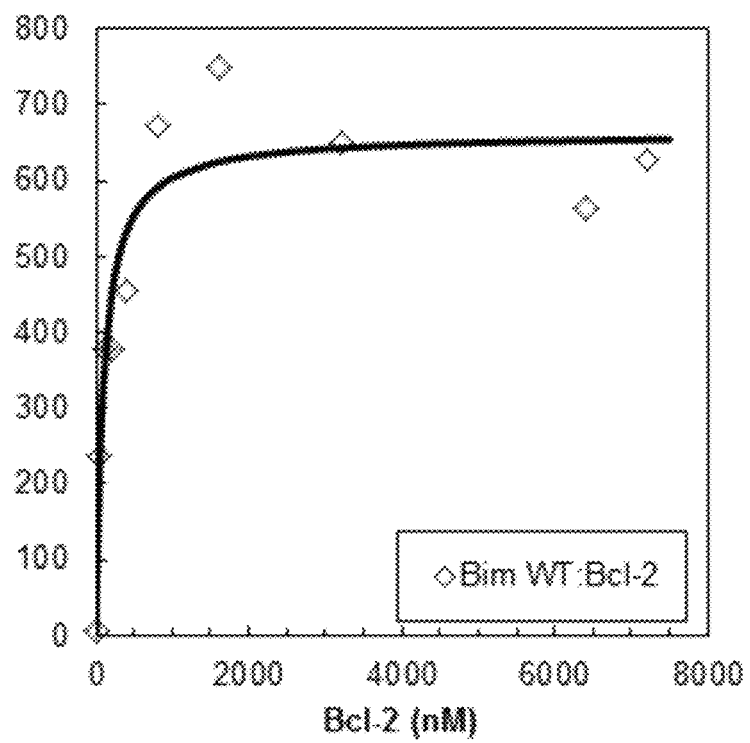
FIG. 6B illustrates apparent $K_d$ measurements of wild-type Bim peptide against Bcl-2.
Figure 6C:
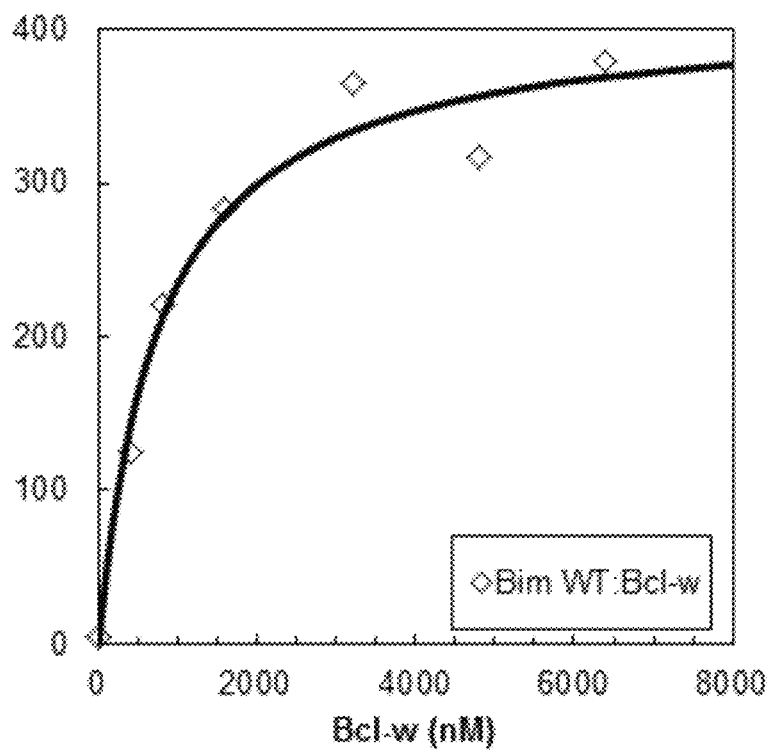
FIG. 6C illustrates apparent $K_d$ measurements of wild-type Bim peptide against Bcl-w.

To find peptides with increased affinity to Bcl-$x_L$, *E. coli* displaying the naïve Bim library was allowed to bind with 12.5 nM Bcl-$x_L$, a concentration 20-fold lower than the $K_d$ of the wild-type Bim peptide with Bcl-$x_L$ (FIG. 6A). The top 0.5% of the population was collected by cell sorting, yielding the X1 library, where X represents that this library was sorted against Bcl-$x_L$ and 1 means that it has been sorted once. Cells harboring the X1 library were regrown, checked for binding to Bcl-$x_L$, and sorted again at higher stringency by incubating with 6.25 nM Bcl-$x_L$. A single population was observed after the $2^{nd}$ round of sorting (the X2 library), with roughly 5-fold higher median fluorescence than wild-type Bim. Individual clones from the X2 library were tested for their binding toward Bcl-$x_L$. Out of 10 clones, 5 showed an increase in fluorescence compared to the wild-type Bim in experiments with 6.25 nM Bcl-$x_L$. These 5 colonies contained 5 distinct sequences (see Table 2 below) and several trends were observed in these sequences. First, F159 was always unchanged in these variants. This finding is reminiscent of the inventor's previous study of Bak BH3 peptide affinity maturation, where the equivalent I85 position on Bak was substituted frequently with Phe in variants with high affinity to Bcl-$x_L$ (Zhang et al., ACS Synth. Biol., 2012 [19], which is incorporated herein by reference as if fully set forth). The I148 position was either unchanged or replaced with a similar aliphatic amino acid. On the other hand, the I155 position included substitutions to bulkier aromatic residues such as Trp and Tyr. One variant, X2-5, disobeyed both of these trends and had I148Y and I155M substitutions. Diversity was observed at position 151, with Thr, Ile, Leu, and Trp being accepted at this position in the affinity matured variants. This result indicates that the negative charge of E151 is likely dispensable with regards to Bcl-$x_L$ binding. Dutta et al. also observed tolerance of diversity at this position (Dutta et al., J. Mol. Biol., 2010 [26], which is incorporated herein by reference as if fully set forth). The substitutions at E151 all removed the negative charge making the resulting peptides good candidates for stapled peptides.

Figure 6D:
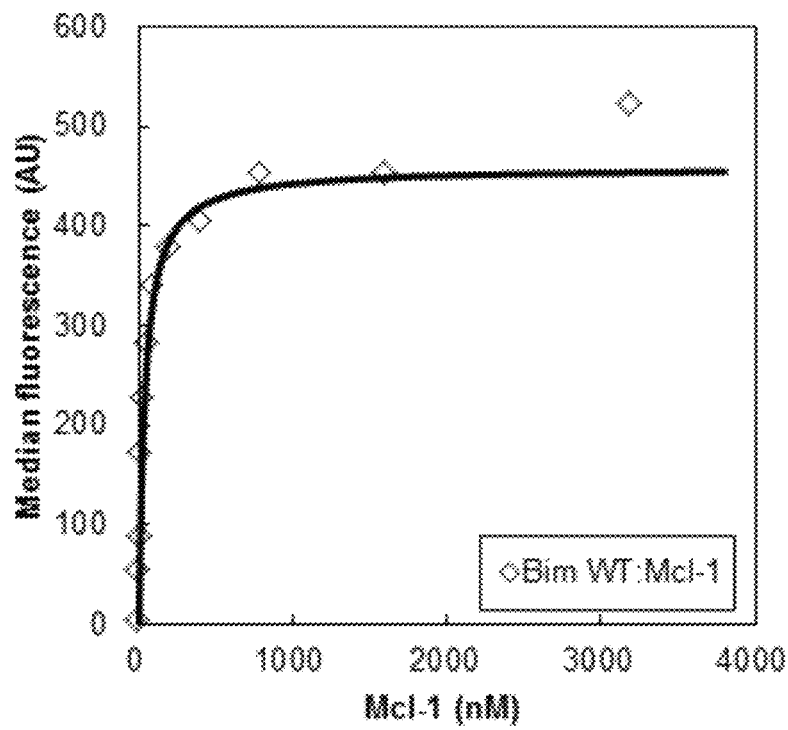
FIG. 6D illustrates apparent $K_d$ measurements of wild-type Bim peptide against Mcl-1.
Figure 6E:
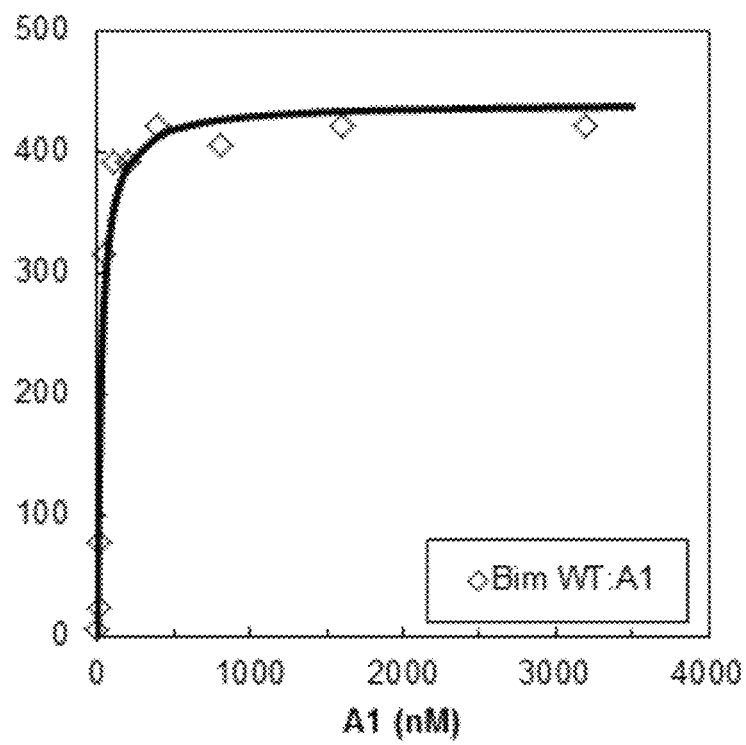
FIG. 6E illustrates apparent $K_d$ measurements of wild-type Bim peptide against A1.

A similar procedure was followed to find Bim BH3 peptides with improved affinity to Mcl-1. The wild-type Bim 14-mer has an apparent $K_d$ of 37.7 nM against Mcl-1 (FIG. 6D), so the naïve library was first sorted against 5 nM Mcl-1. The top 0.4% of the population was sorted, generating the M1 library. The library was further enriched by sorting against 2.5 nM Mcl-1 with collection of the top 0.4% of the population, yielding the M2 library. Ten individual clones were tested from the M2 library at 1.25 nM Mcl-1, 7 of them showed a fluorescence increase over the wild-type peptide, and 5 distinct sequences were observed among these 7 clones (see Table 2 below). Strikingly, in all of the sequences observed, the I155 position was unchanged and the F159 position was substituted with Val or Ile. The I148 position was more tolerant of substitutions, but all observed substitutions were conservative in nature. The E151 position was generally substituted with the hydrophobic amino acids Leu or Ile, though the M2-8 variant retained Glu at this position.

In summary, the highest affinity binders to Bcl-$x_L$ contain bulky aromatic residues in both the I155 and F159 positions while high affinity binders to Mcl-1 have aliphatic amino acids in these positions. The apparent affinity ($K_d$) was determined for many of these variants. Affinity maturation led to as much as a 25-fold increase in apparent affinity toward Bcl-$x_L$ (clone X2-3, see Table 2 below) and as much as a 6-fold apparent affinity increase toward Mcl-1 (clone M2-2, see Table 2 below). The power of this affinity maturation protocol is evident here; with only two rounds of cell sorting, small 14-mer peptides with apparent $K_d$ values below 10 nM to both pro-survival proteins were isolated.

Sequence and apparent $K_d$ values of Bim BH3 variants affinity matured toward Bcl-$x_L$ or Mcl-1 are shown in Table 2 below. Frequency: number of times each clone was observed in screen, ND: not determined. Equilibrium binding curves for this data can be found in FIGS. 6A, 6D and 7A-7AJ.

TABLE 2

| Bim BH3 14-mer | 148 | 151 | 155 | 159 | Frequency | $K_d$ vs. Bcl-$x_L$ (nM) | $K_d$ vs. Mcl-1 (nM) |
|---|---|---|---|---|---|---|---|
| WT | I | E | I | F | 0 | 251 | 37.7 |
| Clones selected against Bcl-$x_L$ | | | | | | | |
| X2-3 | V | W | W | — | 1 | 9.28 | |
| X2-5 | Y | I | M | — | 1 | ND | |

TABLE 2-continued

| Bim BH3 14-mer | 148 | 151 | 155 | 159 | Frequency | $K_d$ vs. Bcl-$x_L$ (nM) | $K_d$ vs. Mcl-1 (nM) |
|---|---|---|---|---|---|---|---|
| X2-8 | L | L | Y | — | 1 | 17.8 | |
| X2-9 | — | I | W | — | 1 | ND | |
| X2-10 | V | T | W | — | 1 | 17.0 | |
| Clones selected against Mcl-1 | | | | | | | |
| M2-1 | — | L | — | V | 1 | | 10.3 |
| M2-2 | V | L | — | V | 2 | | 5.80 |
| M2-3 | M | I | — | V | 2 | | 11.5 |
| M2-4 | L | L | — | I | 1 | | 9.85 |
| M2-8 | L | — | — | V | 1 | | ND |

Example 4—Investigating the Role of Residue E151

Figure 2:
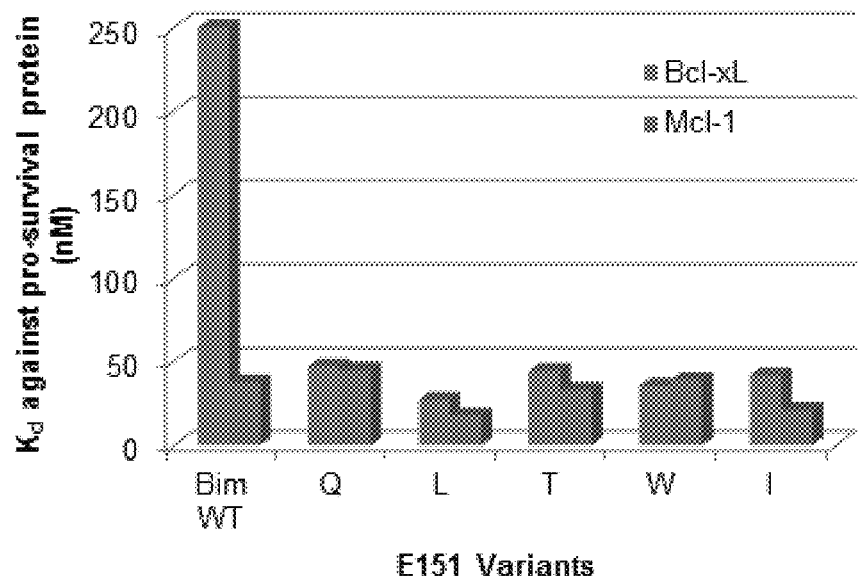
FIG. 2 illustrates apparent $K_d$ values for Bim variants with amino acid substitution at the E151 position toward the pro-survival proteins Bcl-$x_L$ (left bar for each of Bim WT, Q, L, T, W and I) and Mcl-1 (right bar for each of Bim WT, Q, L, T, W, and I).

The affinity matured Bim variants isolated from the screen include several different substitutions at the E151 position. Determination was sought as to whether these substitutions were neutral or active participants in the affinity improvement observed. Bim 14-mer variants with a single substitution at the E151 position to T, I, L, or W were generated. In addition, a charge-neutral "pseudo-wild-type" peptide containing a E151Q substitution was constructed. The apparent $K_d$ for each of these E151 variants was determined, and it was found that all of them had 5- to 8-fold increases in apparent affinity toward Bcl-$x_L$ (FIG. 2). The E151L and E151I variants also showed a 2-fold increase in apparent affinity toward Mcl-1, consistent with their appearance in the screens against Mcl-1. The apparent affinities of the E151T, E151W, and the pseudo-wild-type E151Q variants to Mcl-1 were similar to the wild-type peptide. This finding goes beyond the previous finding that many amino acids can be tolerated at the E151 position (Dutta et al., J. Mol. Biol., 2010 [26], which is incorporated herein by reference as if fully set forth) and indicates that substitutions at this position can lead to affinity improvements.

Binding of Bim Variants to Other Pro-Survival Proteins

A subset of the affinity matured Bim variants was chosen for further characterization and eventual synthesis as stapled peptides. Two Bim variants were selected from each screen. Any variants containing methionine were not considered because of potential complications due to methionine oxidation. The variant X2-3 was chosen because it was the only variant with a bulky Trp at position 151 and was the variant with the lowest apparent $K_d$ toward Bcl-$x_L$ (9.3 nM). The X2-8 variant was chosen because it was the only variant with Tyr rather than Trp at position 155. Variants M2-2 and M2-4 were chosen from the Mcl-1 enriched pool because M2-2 has the strongest affinity to Mcl-1 (5.8 nM) and M2-4 is the only variant with Ile replacing Phe at position 159. This selection of peptides covers the wide range of diversity observed in the library screen. The E151Q variant was also chosen for characterization and synthesis to serve as a charge-neutral pseudo-wild-type peptide.

Figure 7A:
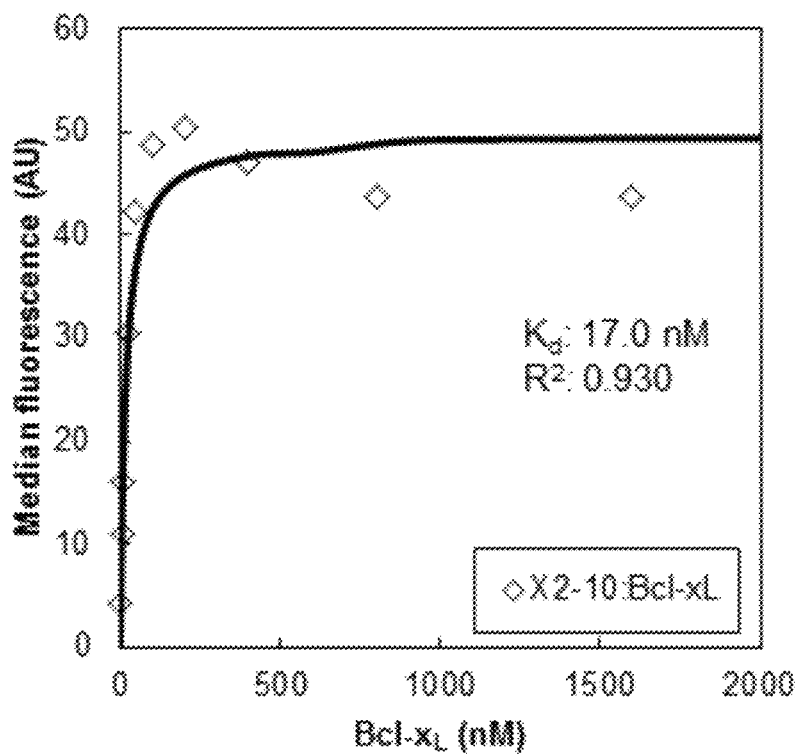
FIG. 7A illustrates apparent $K_d$ measurements of X2-10 binding Bcl-$_{XL}$.
Figure 7B:
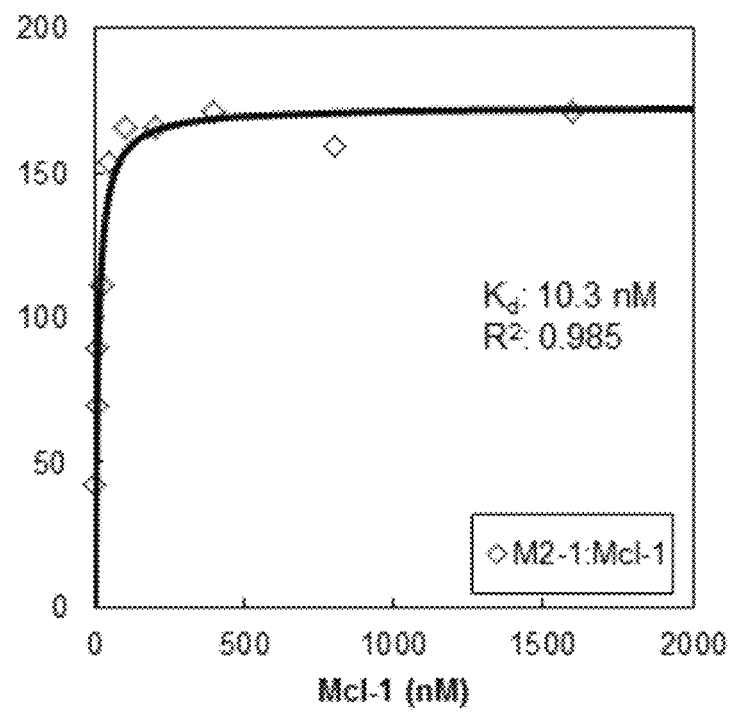
FIG. 7B illustrates apparent $K_d$ measurements of M2-1 binding Mcl-1.
Figure 7C:
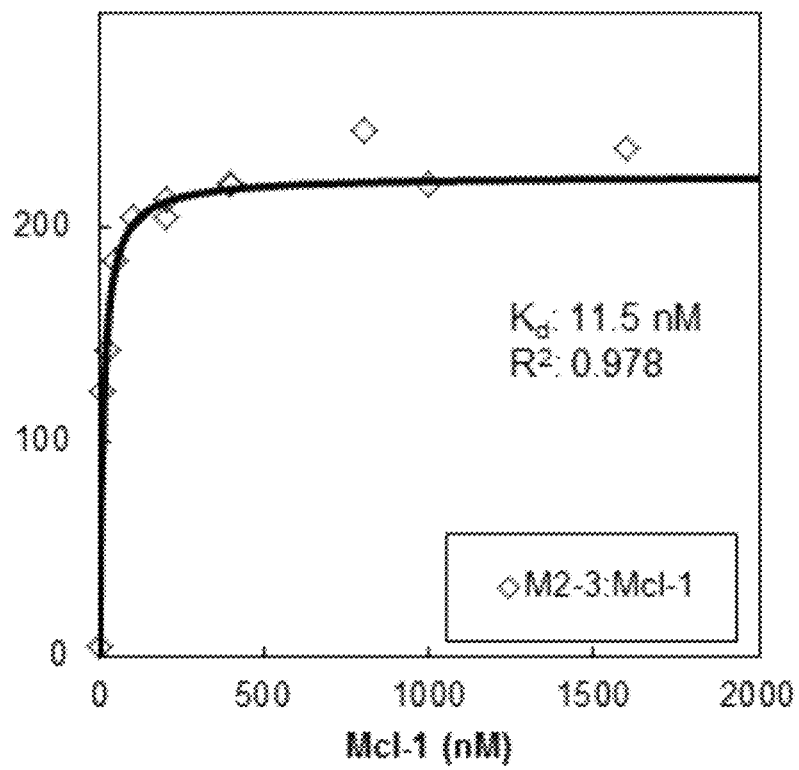
FIG. 7C illustrates apparent $K_d$ measurements of M2-3 binding Mcl-1.
Figure 7D:
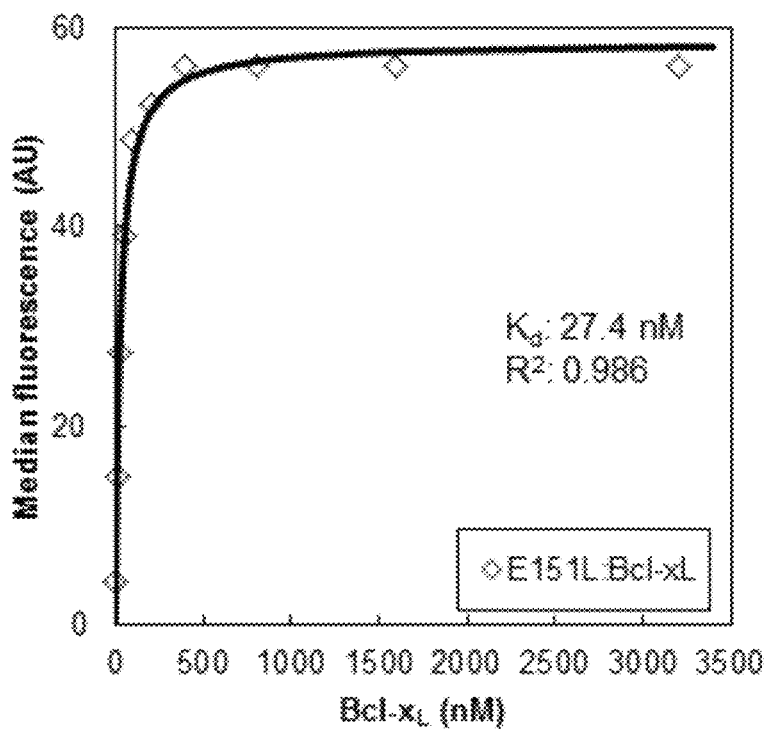
FIG. 7D illustrates apparent $K_d$ measurements of E151L binding Bcl-$_{XL}$.
Figure 7E:
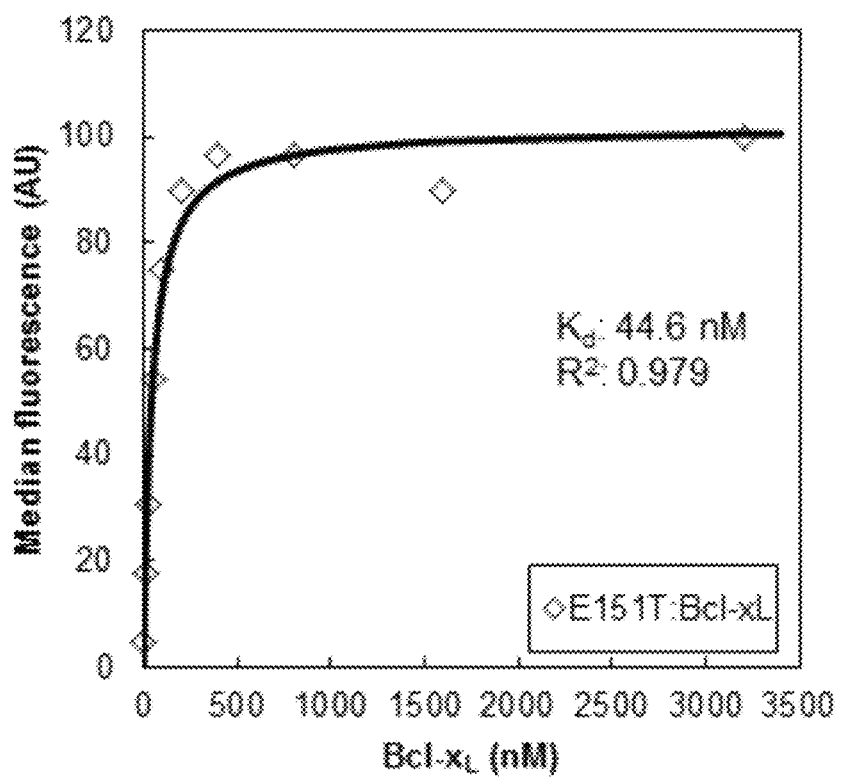
FIG. 7E illustrates apparent $K_d$ measurements of E151T binding Bcl-$_{XL}$.
Figure 7F:
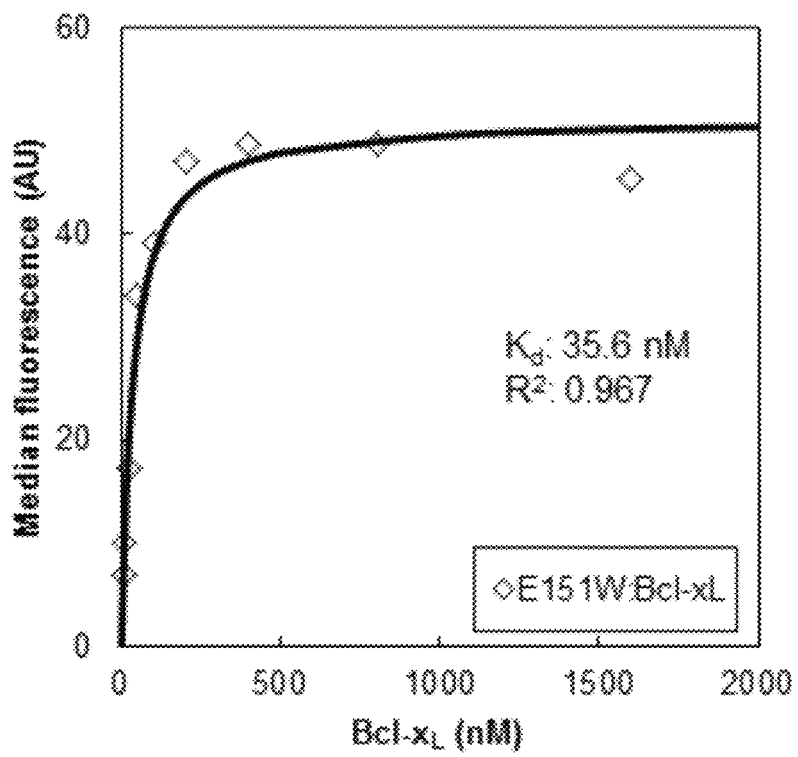
FIG. 7F illustrates apparent $K_d$ measurements of E151W binding Bcl-$_{XL}$.
Figure 7G:
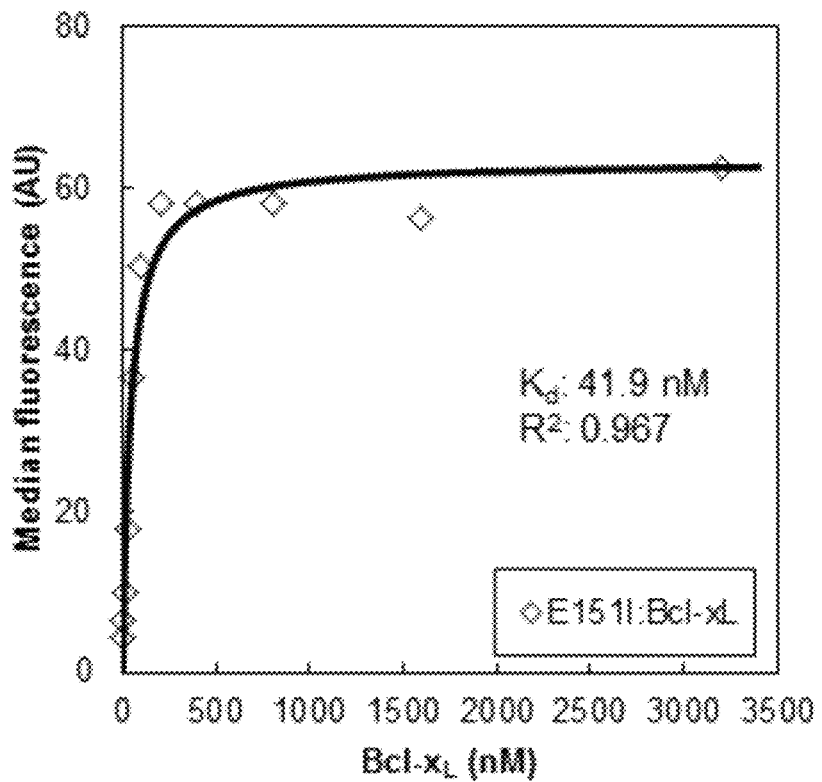
FIG. 7G illustrates apparent $K_d$ measurements of E151I binding Bcl-$_{XL}$.
Figure 7H:
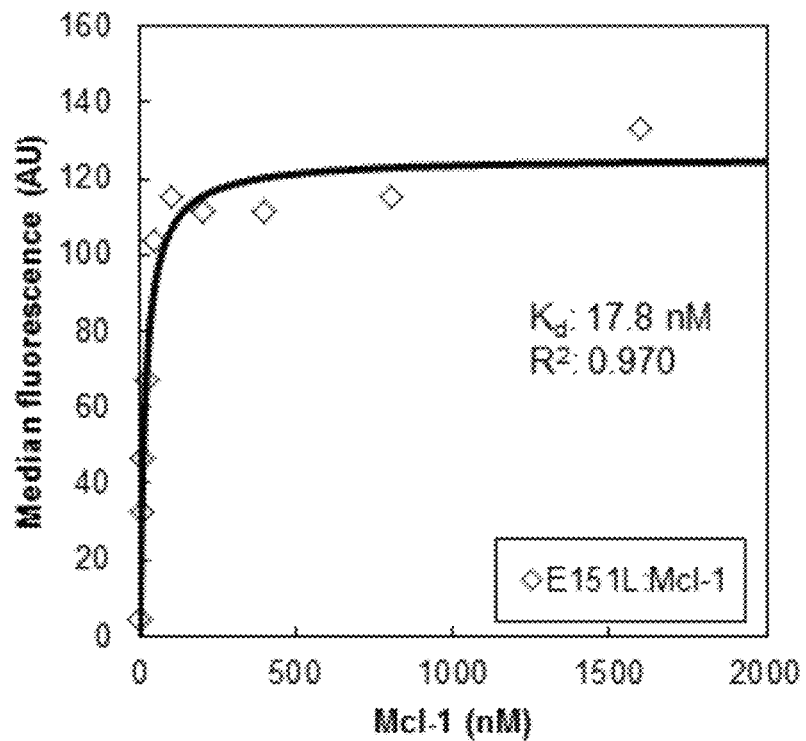
FIG. 7H illustrates apparent $K_d$ measurements of E151L binding Mcl-1.
Figure 7I:
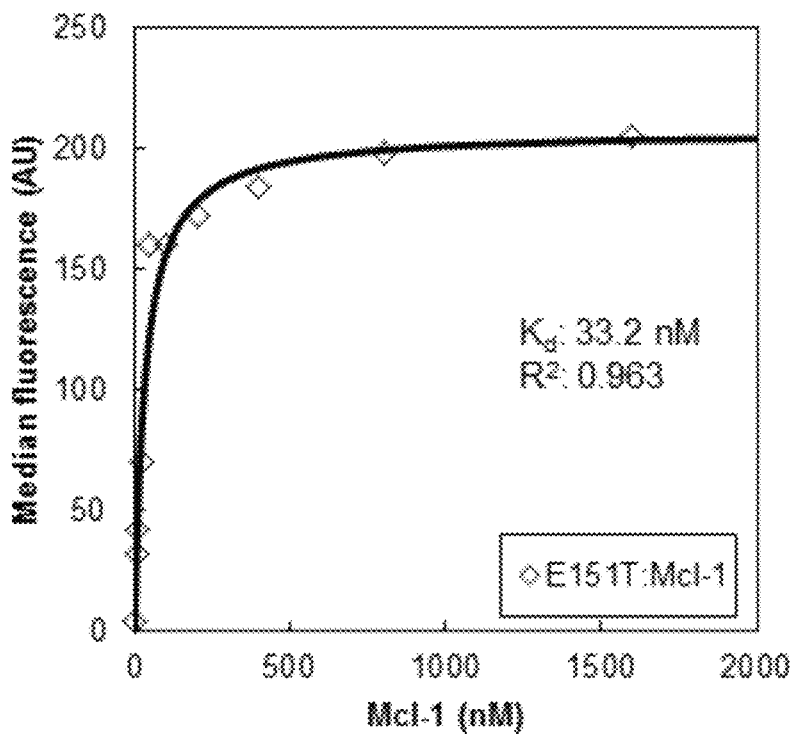
FIG. 7I illustrates apparent $K_d$ measurements of E151T binding Mcl-1.
Figure 7J:
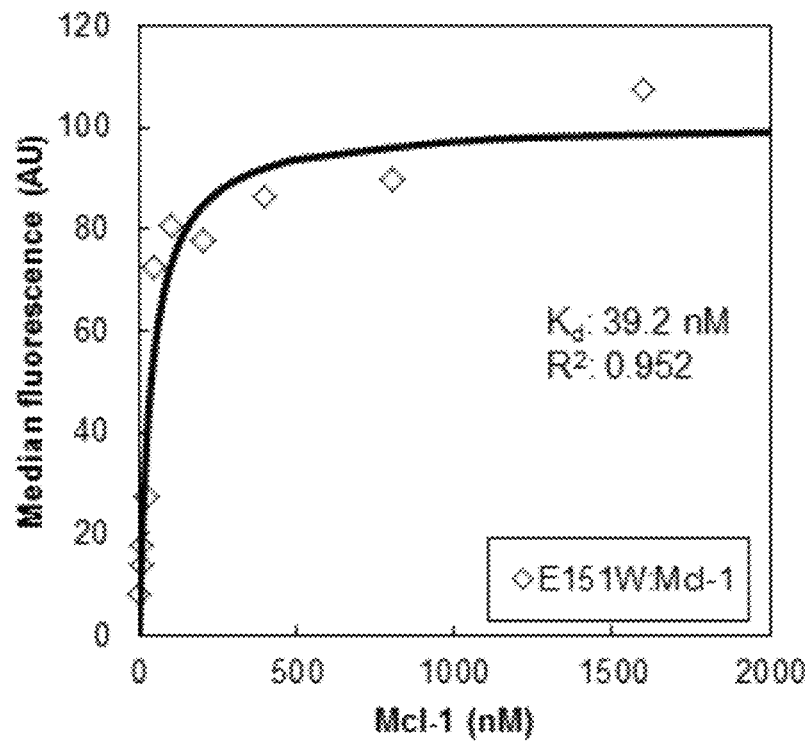
FIG. 7J illustrates apparent $K_d$ measurements of E151W binding Mcl-1.
Figure 7K:
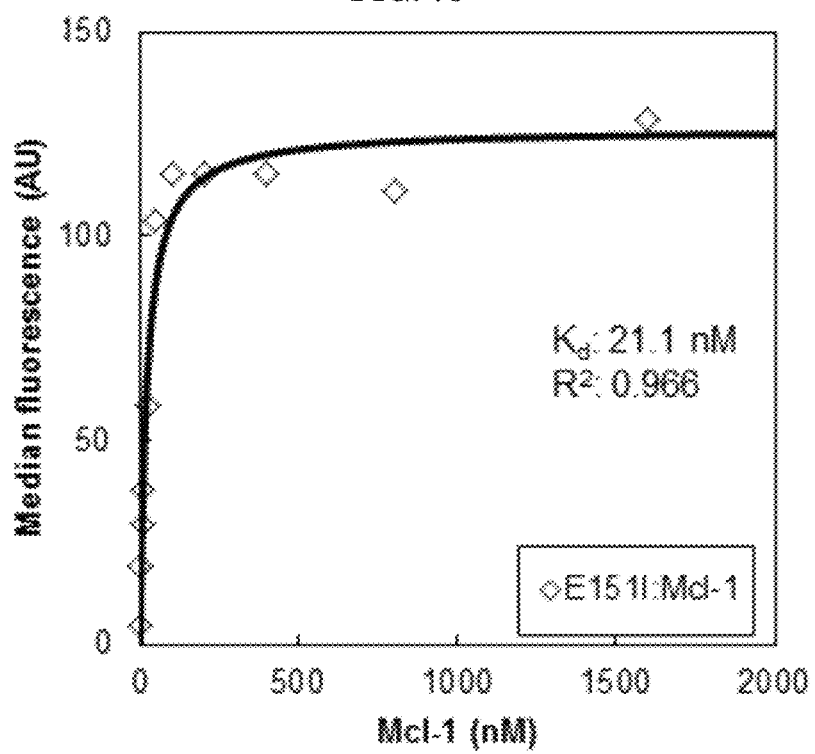
FIG. 7K illustrates apparent $K_d$ measurements of E151I binding Mcl-1.
Figure 7L:
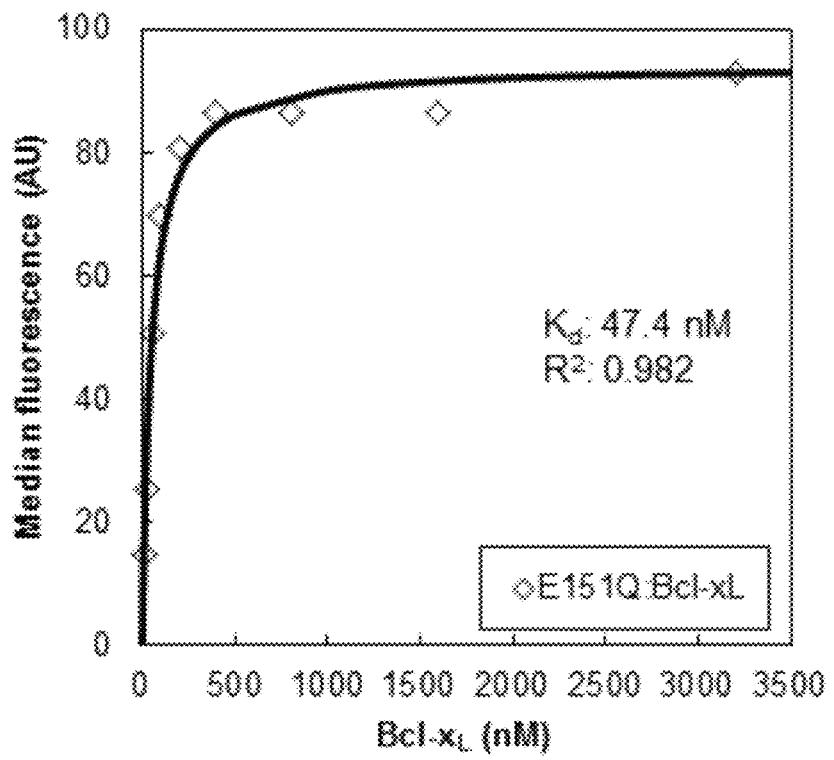
FIG. 7L illustrates apparent $K_d$ measurements of E151Q binding Bcl-$_{XL}$.
Figure 7M:
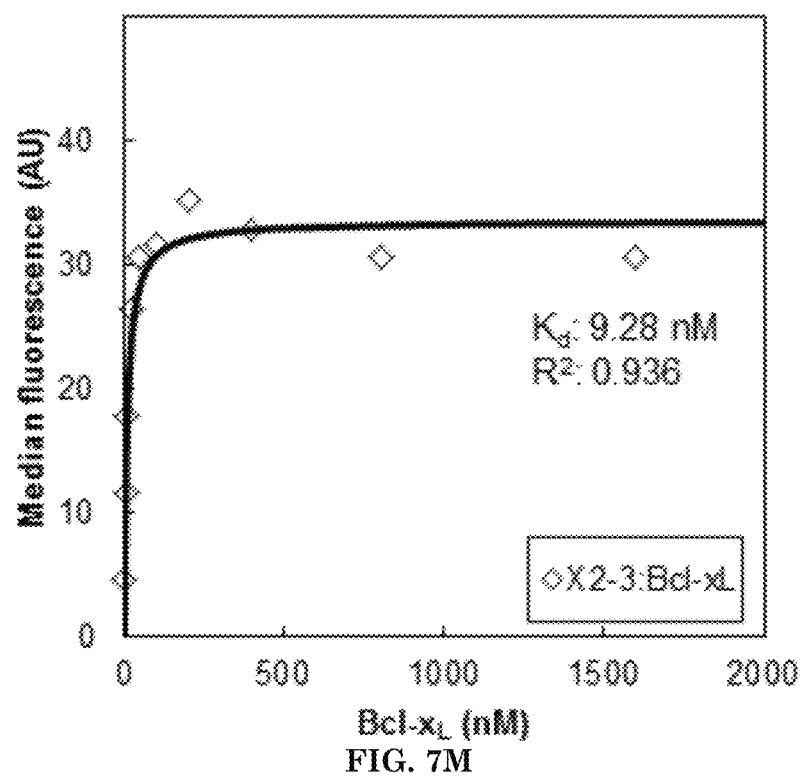
FIG. 7M illustrates apparent $K_d$ measurements of X2-3 binding Bcl-$_{XL}$.
Figure 7N:
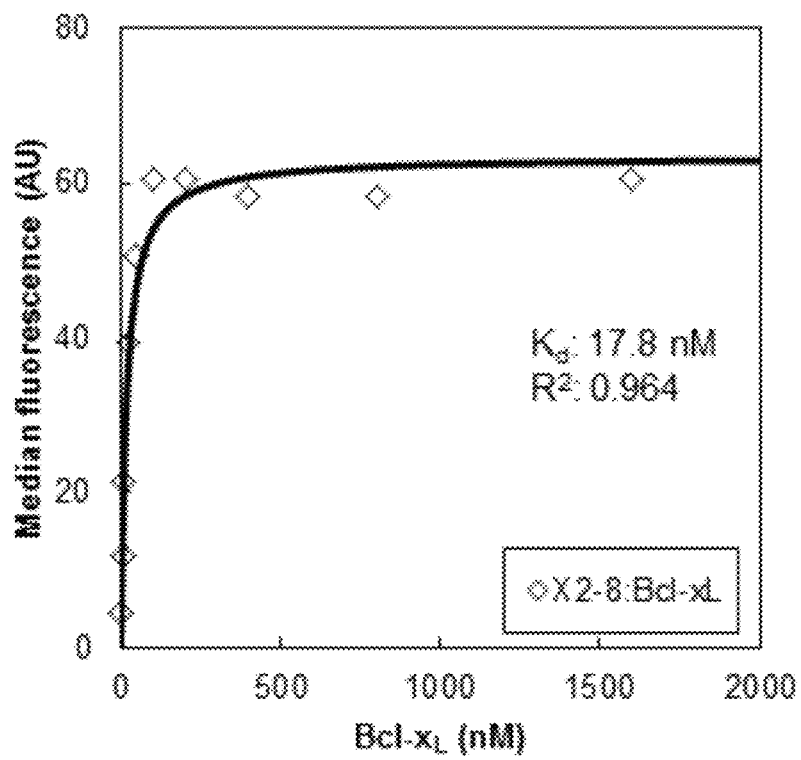
FIG. 7N illustrates apparent $K_d$ measurements of X2-8 binding Bcl-$_{XL}$.
Figure 7O:
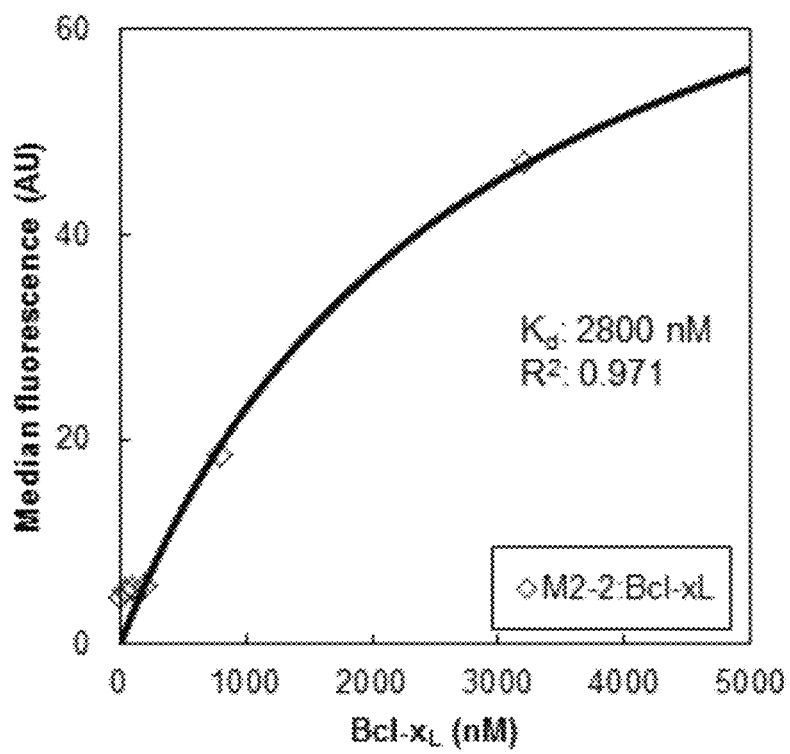
FIG. 7O illustrates apparent $K_d$ measurements of M2-2 binding Bcl-$_{XL}$.
Figure 7P:
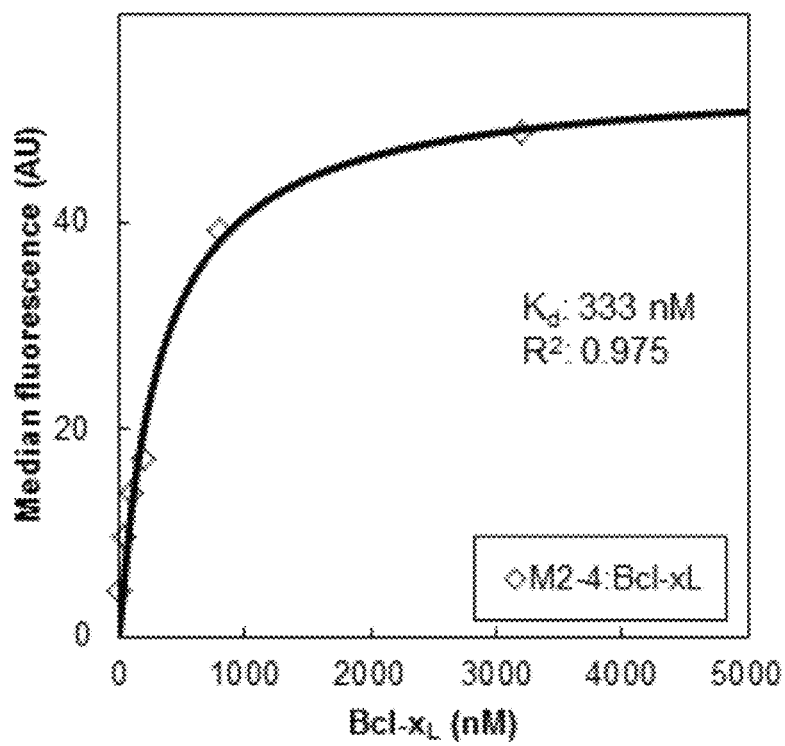
FIG. 7P illustrates apparent $K_d$ measurements of M2-4 binding Bcl-$_{XL}$.
Figure 7Q:
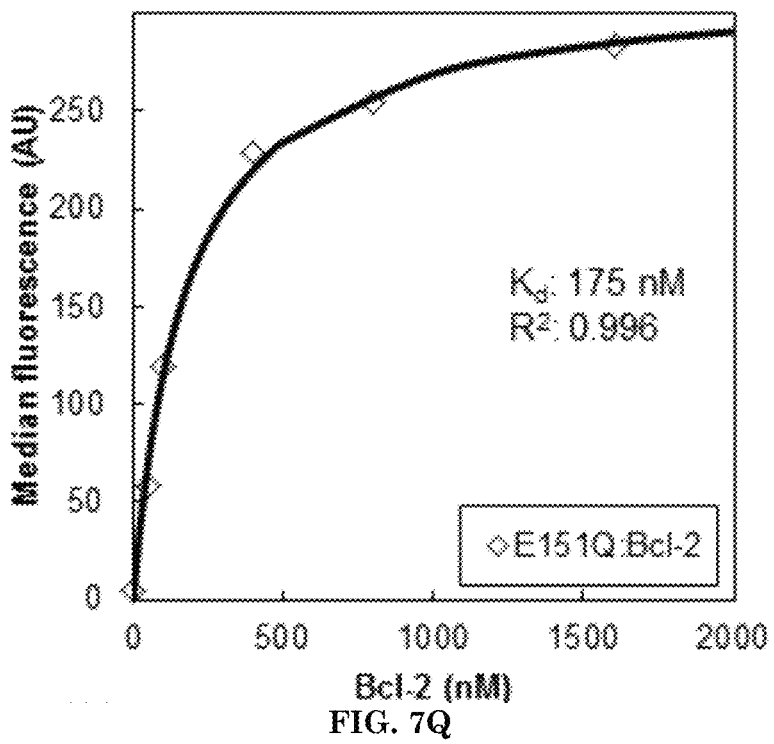
FIG. 7Q illustrates apparent $K_d$ measurements of E151Q binding Bcl-2
Figure 7R:
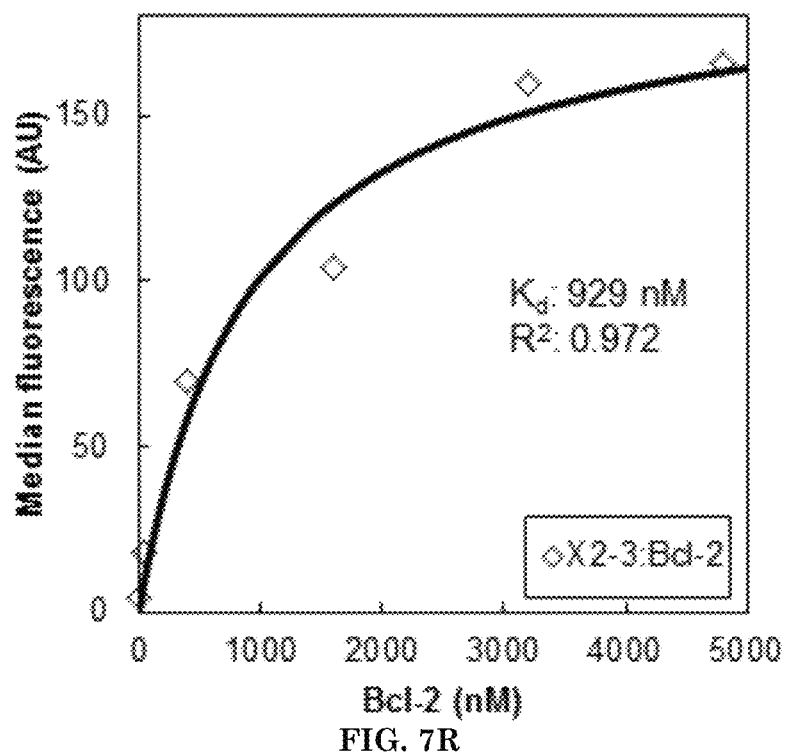
FIG. 7R illustrates apparent $K_d$ measurements of X2-3 binding Bcl-2.
Figure 7S:
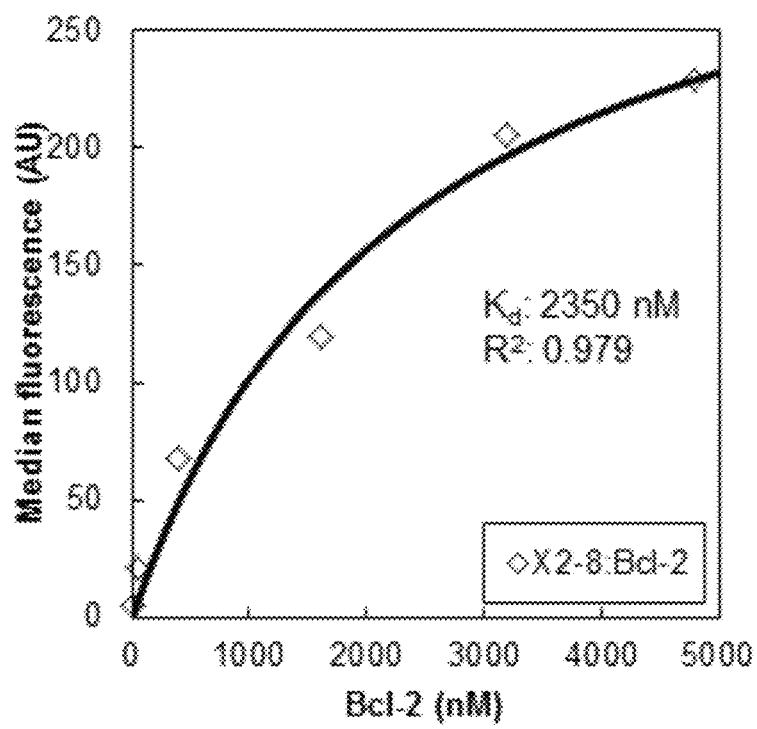
FIG. 7S illustrates apparent $K_d$ measurements of X2-8 binding Bcl-2.
Figure 7T:
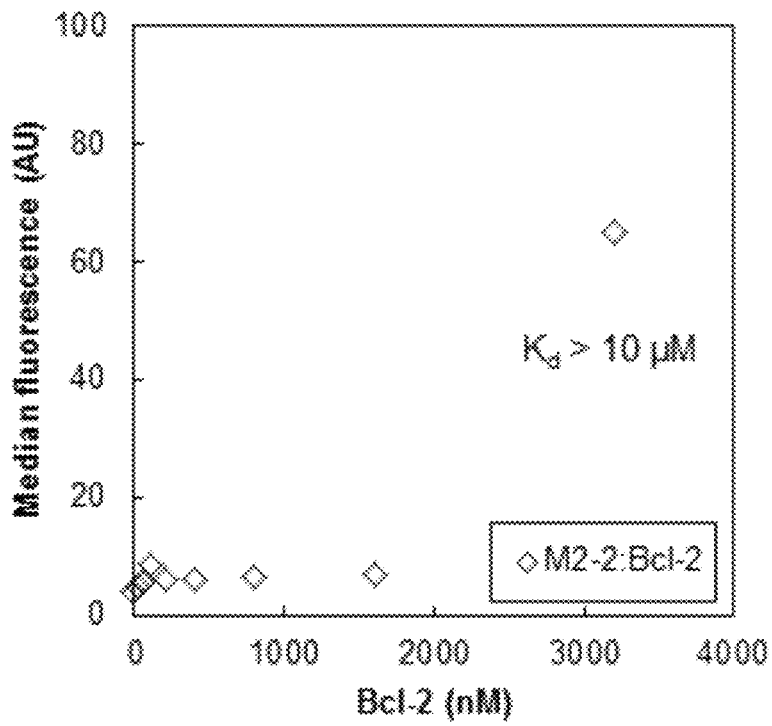
FIG. 7T illustrates apparent $K_d$ measurements of M2-2 binding Bcl-2.
Figure 7U:
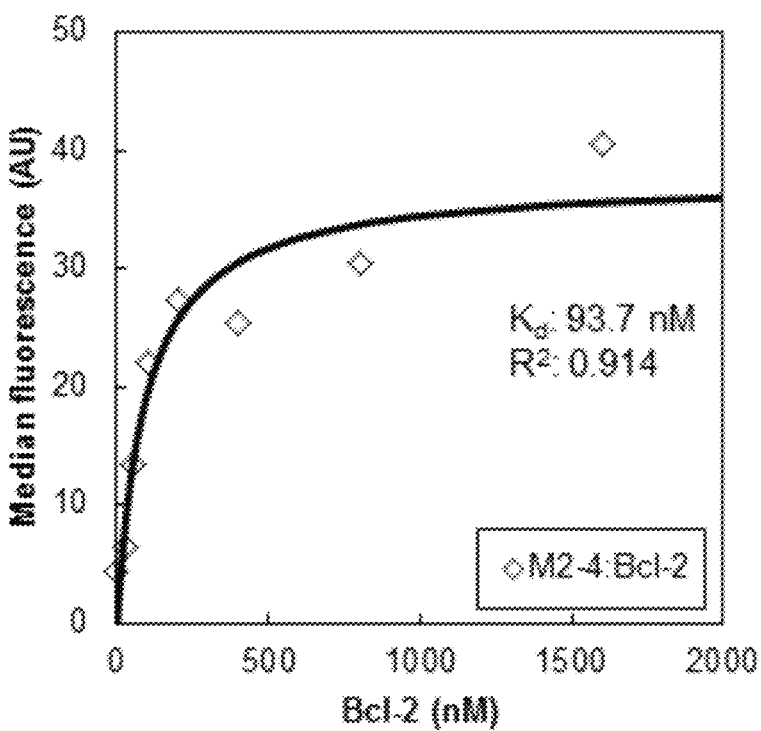
FIG. 7U illustrates apparent $K_d$ measurements of M2-4 binding Bcl-2.
Figure 7V:
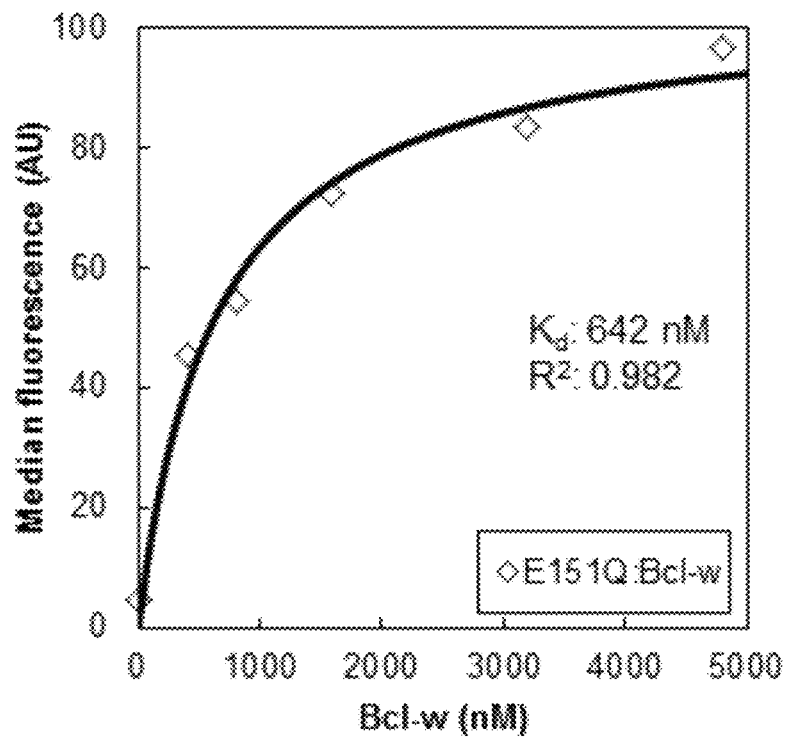
FIG. 7V illustrates apparent $K_d$ measurements of E151Q binding Bcl-w.
Figure 7W:
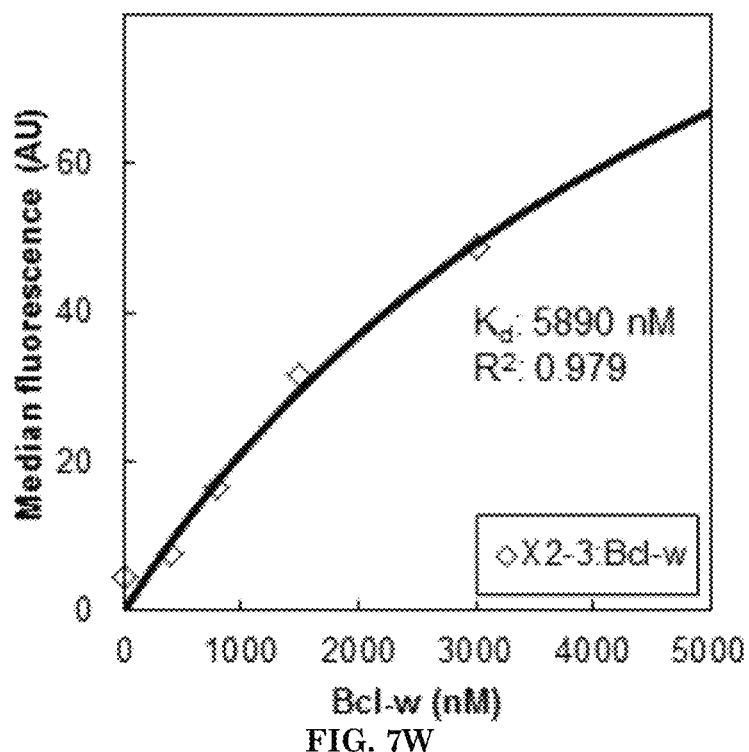
FIG. 7W illustrates apparent $K_d$ measurements of X2-3 binding Bcl-w.
Figure 7X:
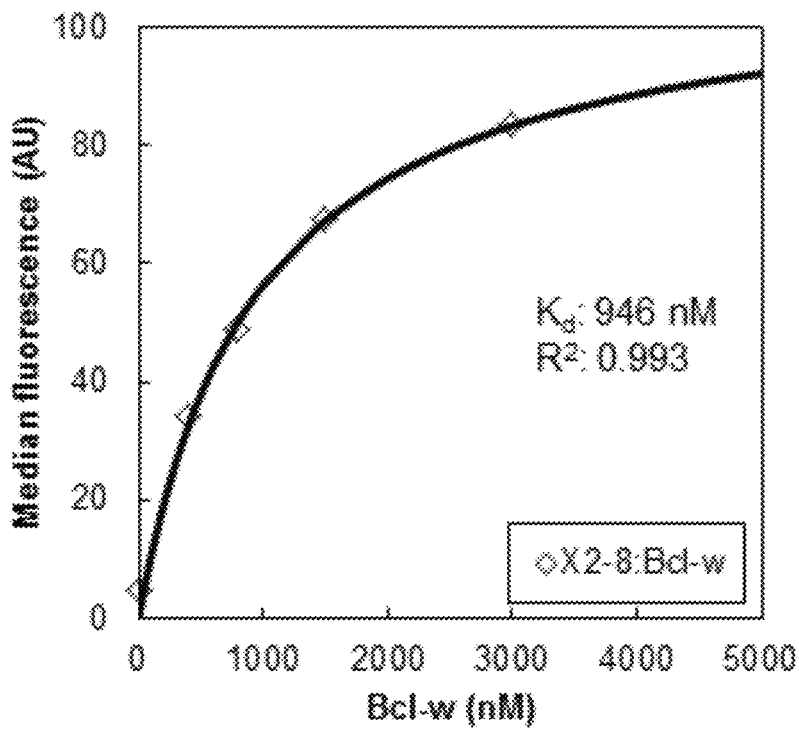
FIG. 7X illustrates apparent $K_d$ measurements of X2-8 binding Bcl-w.
Figure 7Y:
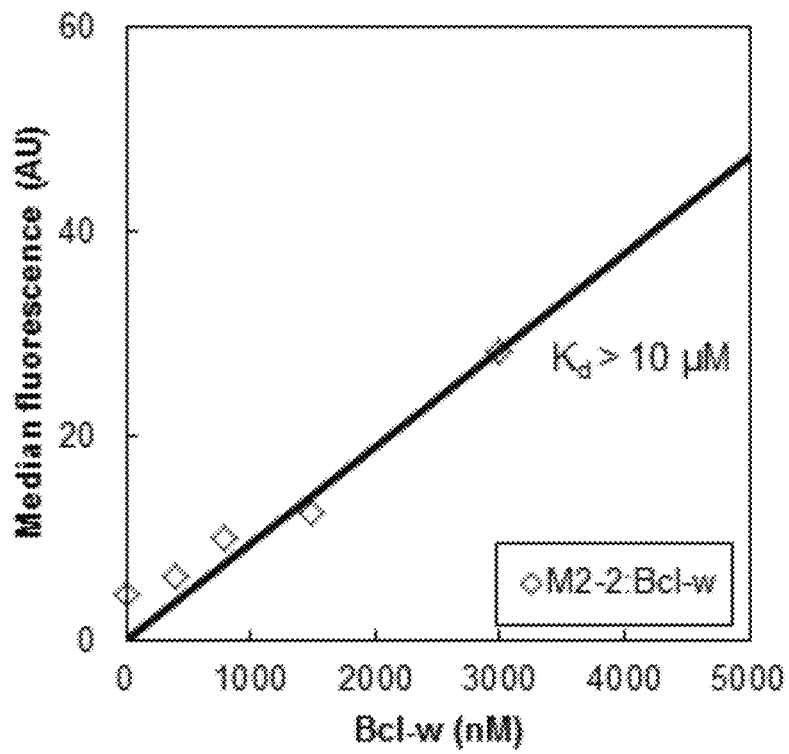
FIG. 7Y illustrates apparent $K_d$ measurements of M2-2 binding Bcl-w.
Figure 7Z:
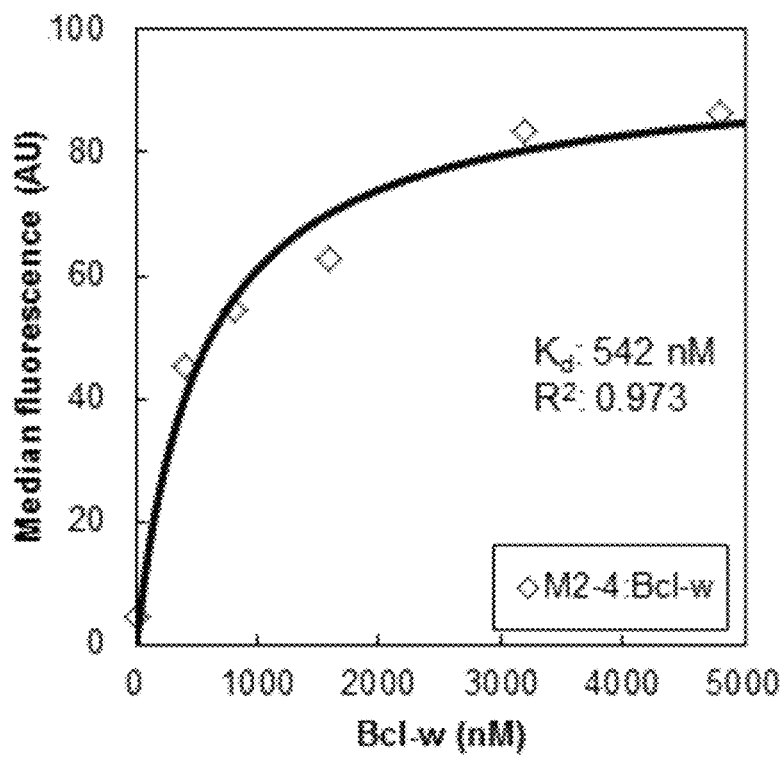
FIG. 7Z illustrates apparent $K_d$ measurements of M2-4 binding Bcl-w.
Figure 7A:
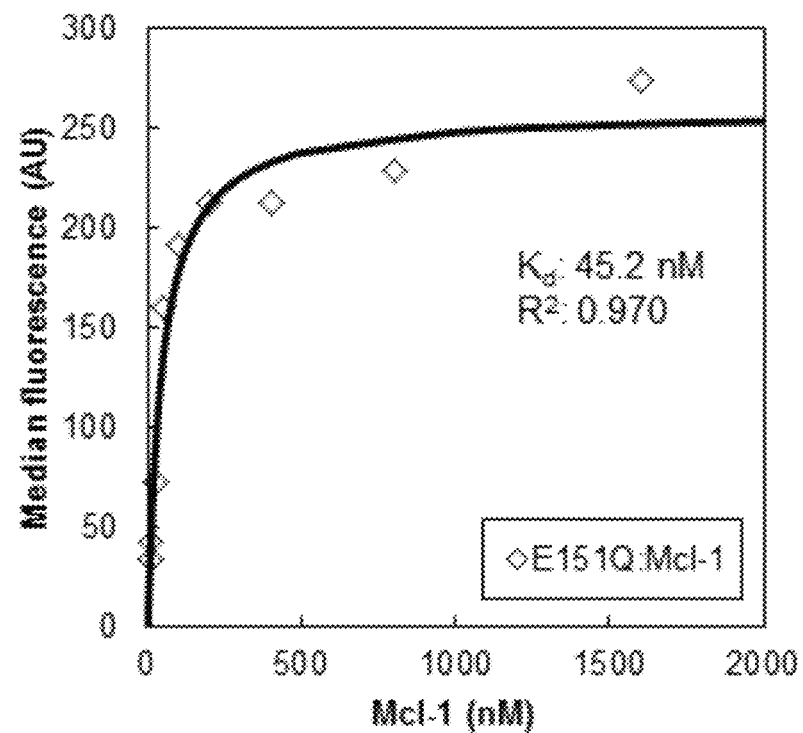
Figure 7A:
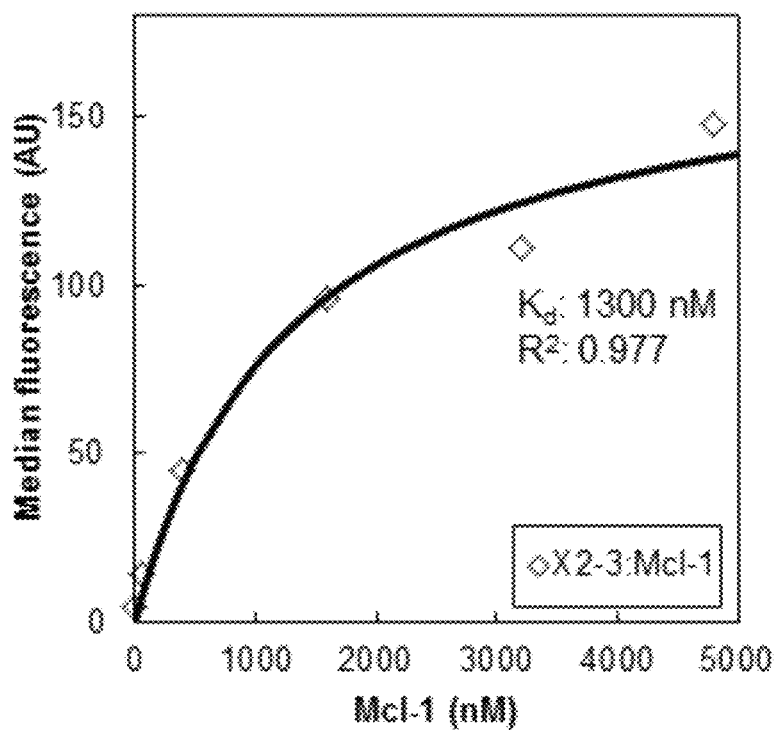
Figure 7A:
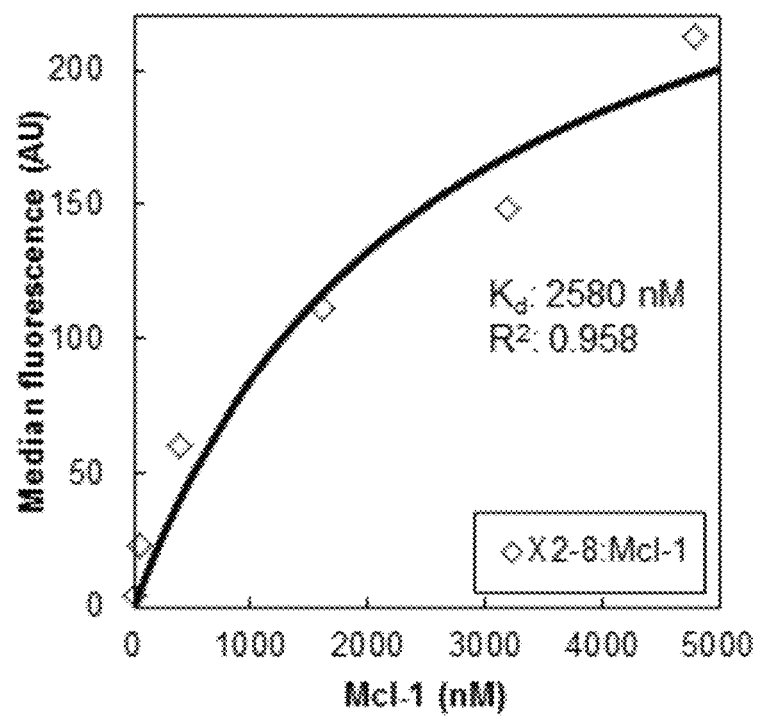
Figure 7A:
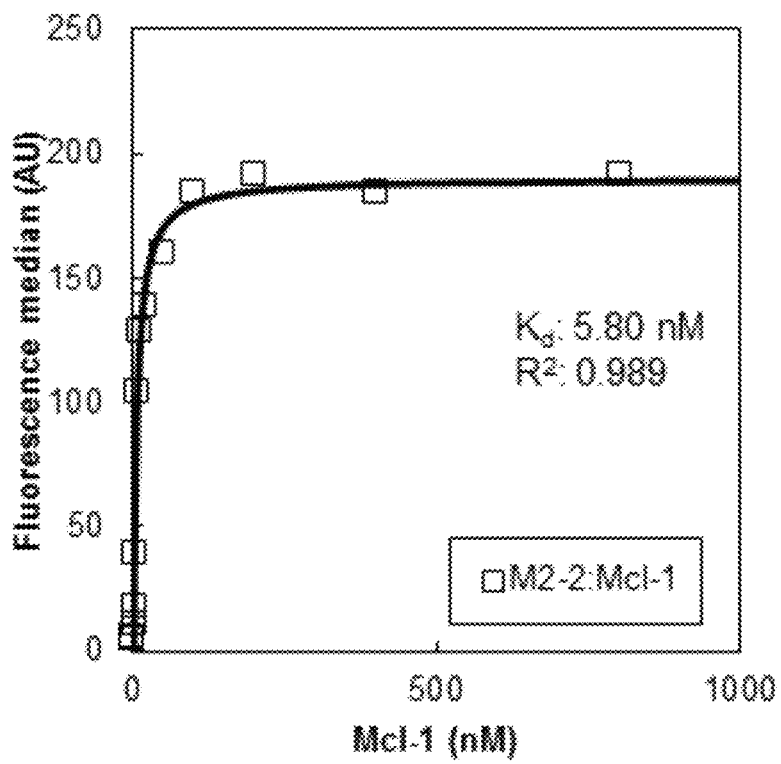
Figure 7A:
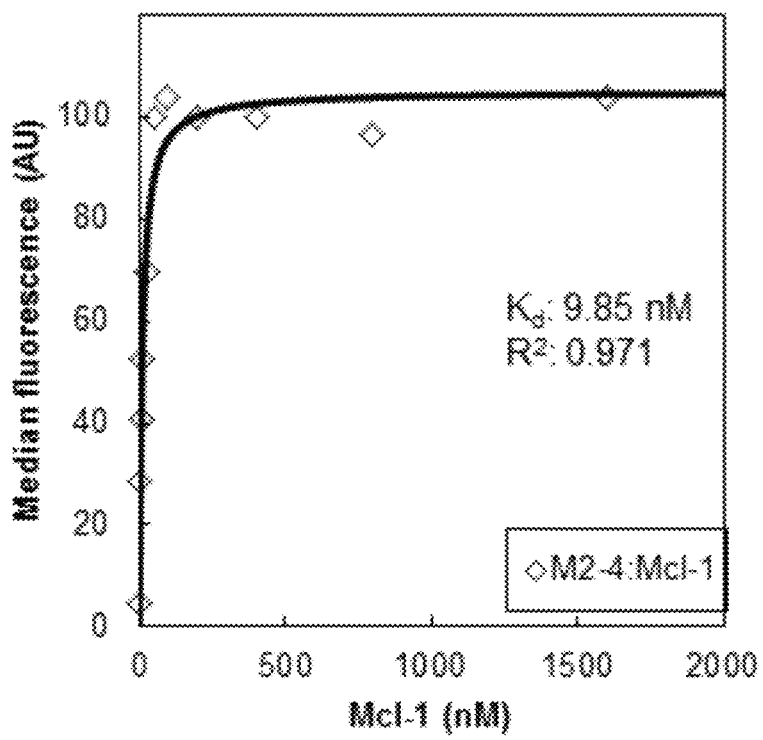
Figure 7A:
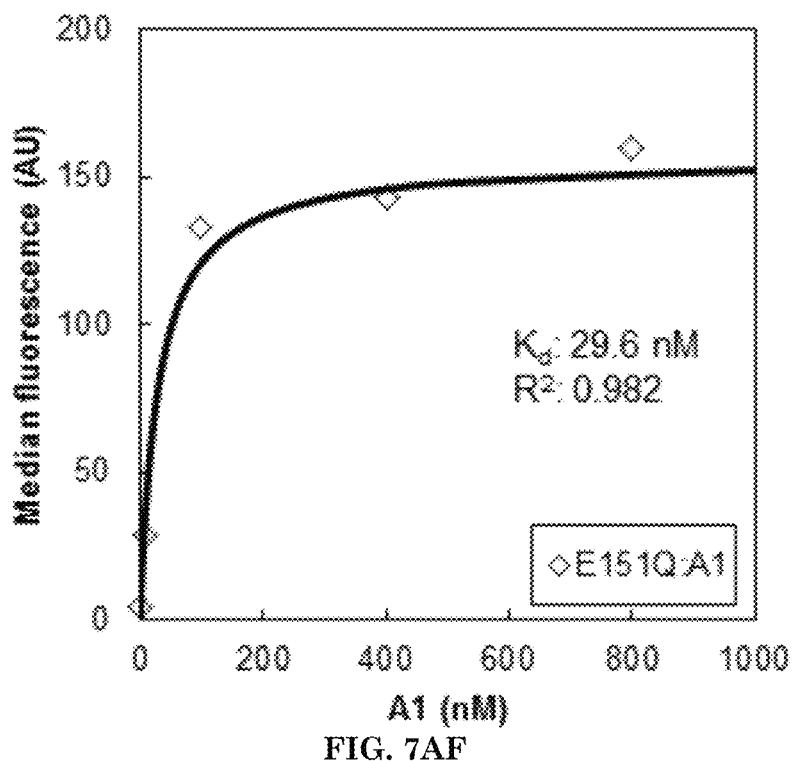
Figure 7A:
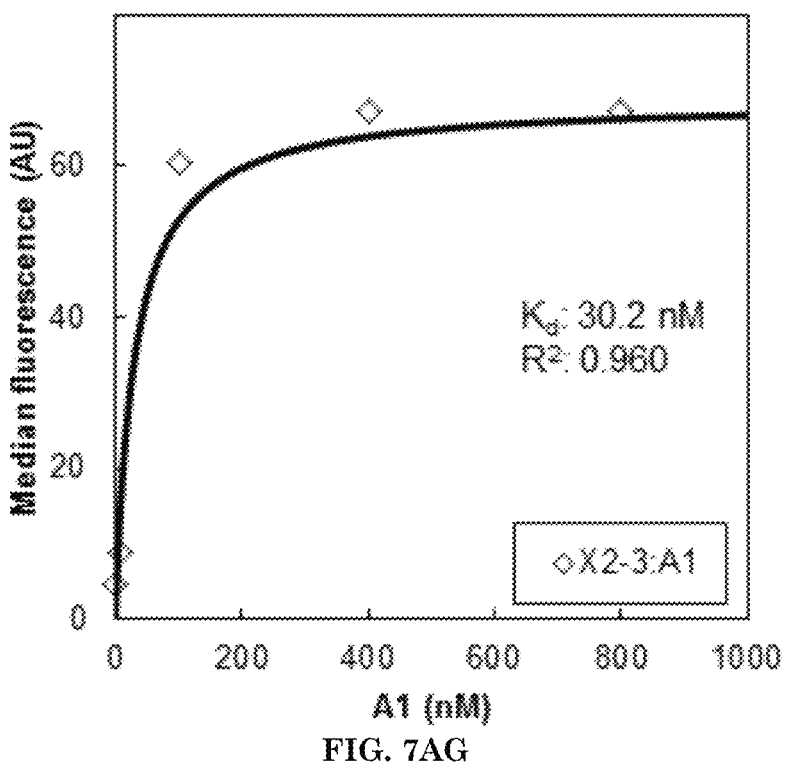
Figure 7A:
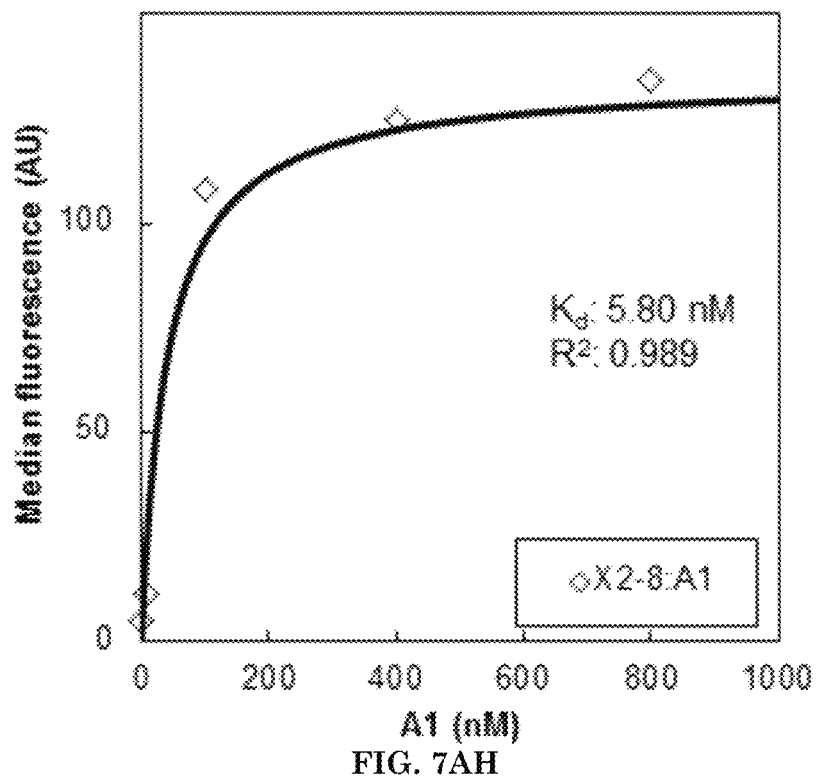
Figure 7A:
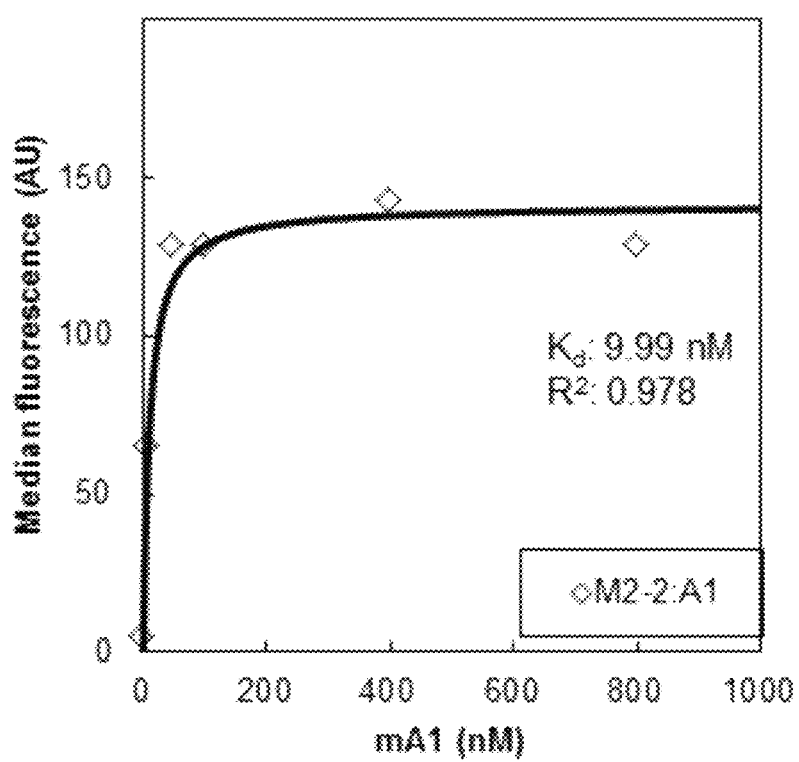
Figure 7A:
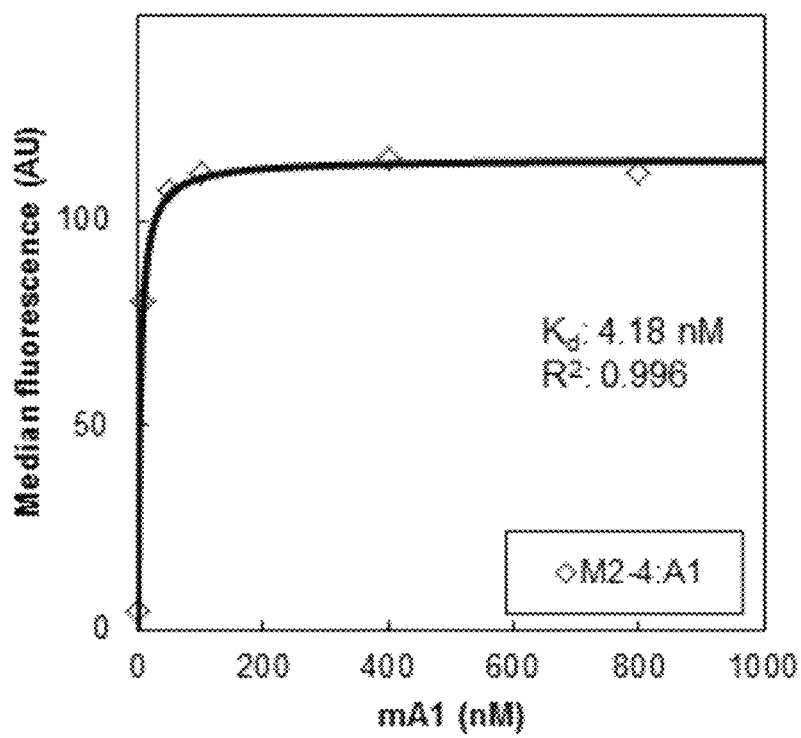
Figure 8A:
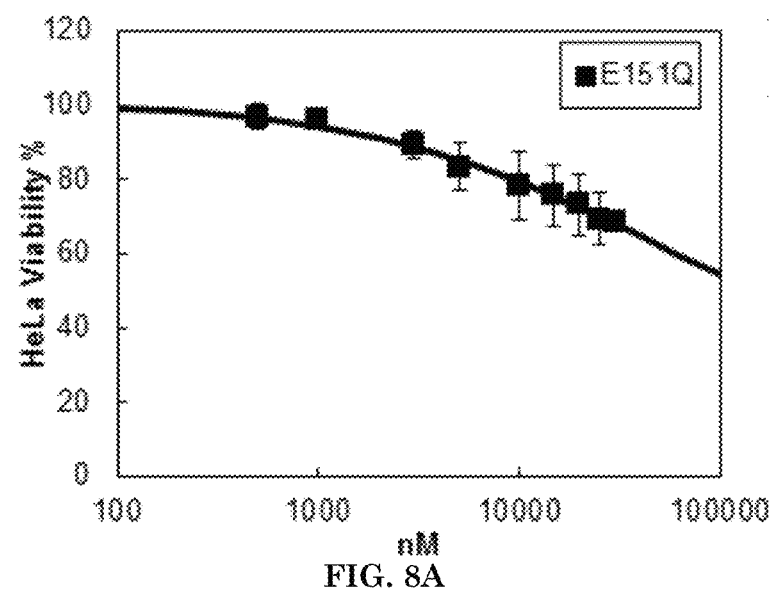
FIG. 8A illustrates MTT assays of stapled E151Q against HeLa cells.
Figure 8B:
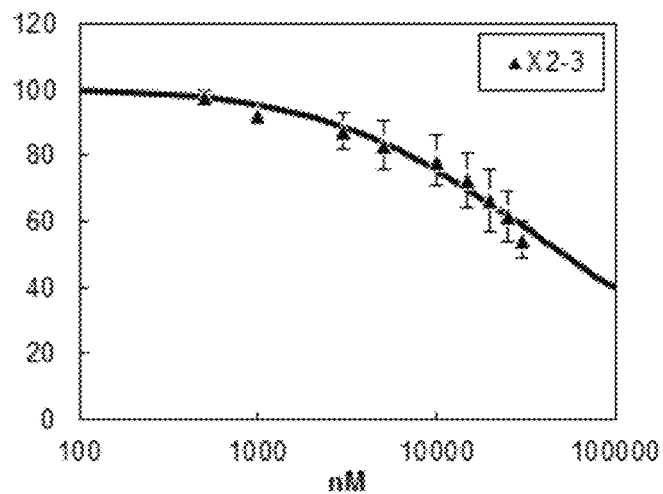
FIG. 8B illustrates MTT assays of stapled X2-3 against HeLa cells.
Figure 8C:
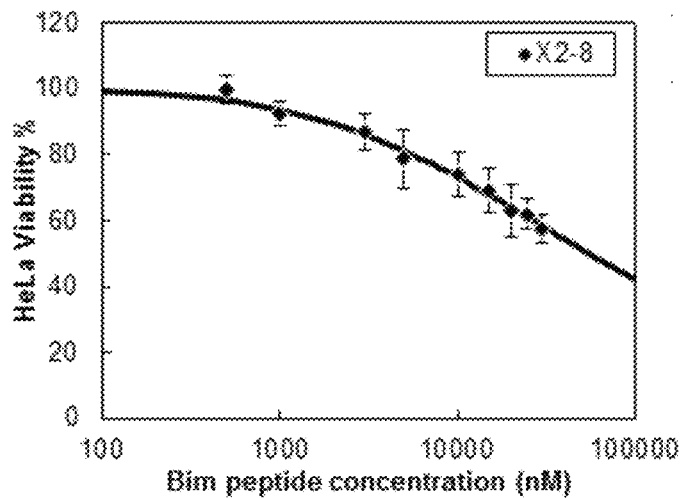
FIG. 8C illustrates MTT assays of stapled X2-8 against HeLa cells.
Figure 8D:
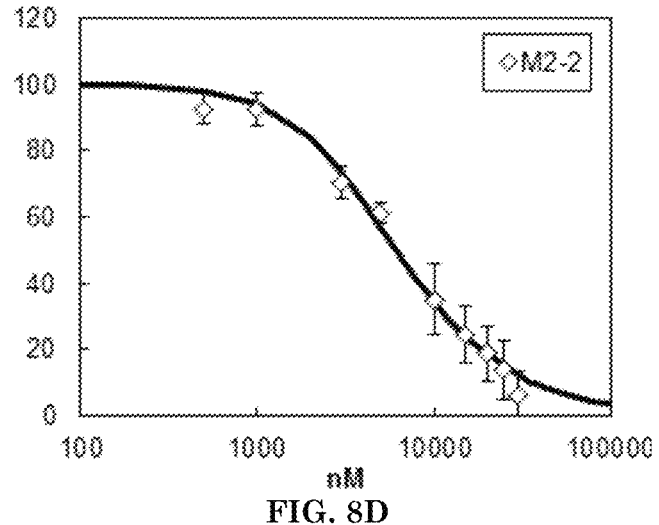
FIG. 8D illustrates MTT assays of stapled M2-2 against HeLa cells.
Figure 8E:
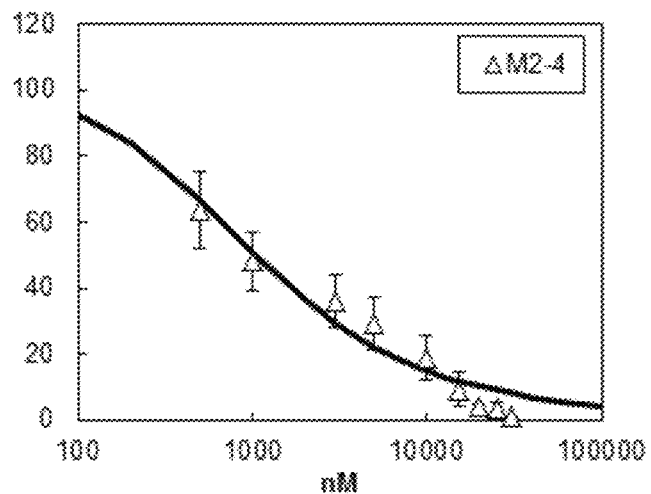
FIG. 8E illustrates MTT assays of stapled M2-4 against HeLa cells.
Figure 9A:
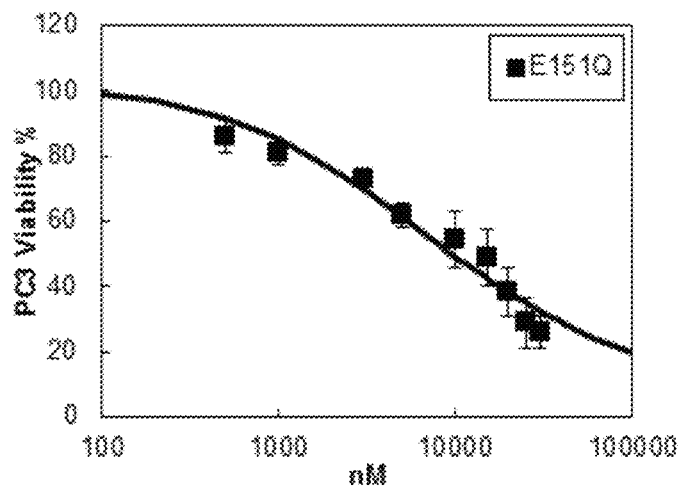
FIG. 9A illustrates MTT assays of stapled E151Q against PC3 cells.
Figure 9B:
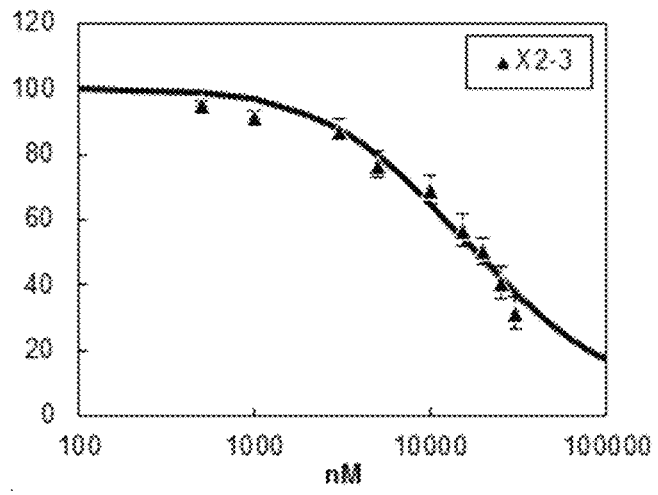
FIG. 9B illustrates MTT assays of stapled X2-3 against PC3 cells.
Figure 9C:
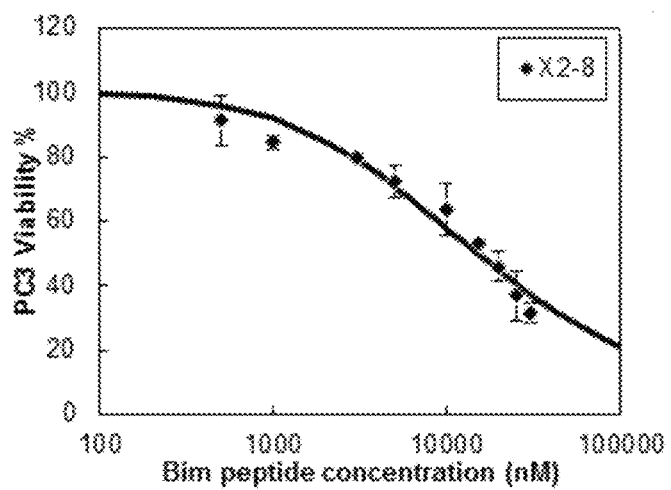
FIG. 9C illustrates MTT assays of stapled X2-8 against PC3 cells.
Figure 9D:
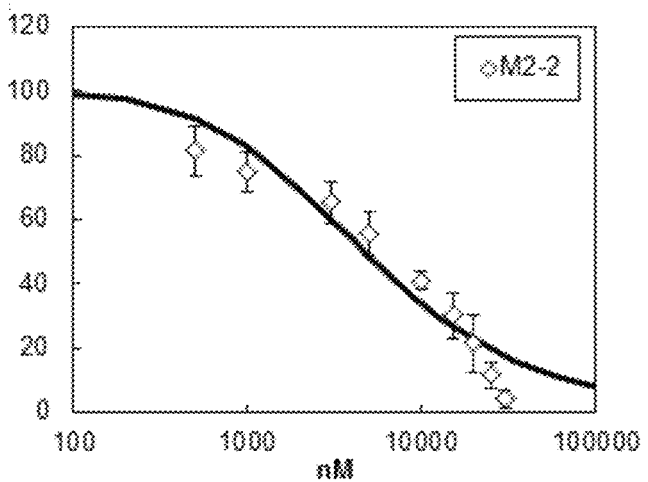
FIG. 9D illustrates MTT assays of stapled M2-2 against PC3 cells.
Figure 9E:
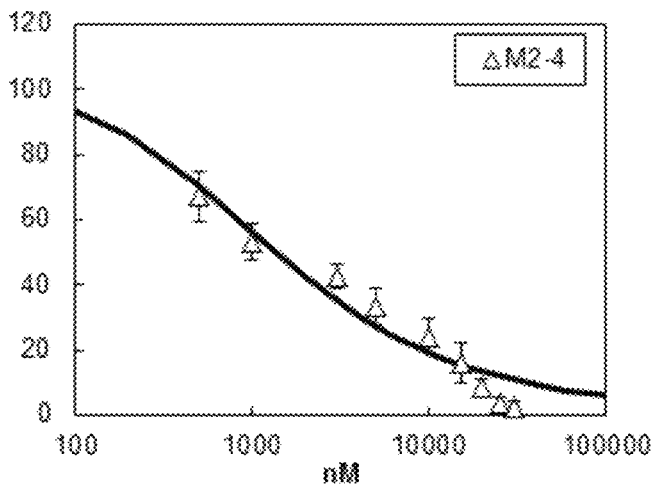
FIG. 9E illustrates MTT assays of stapled M2-4 against PC3 cells.
Figure 10A:
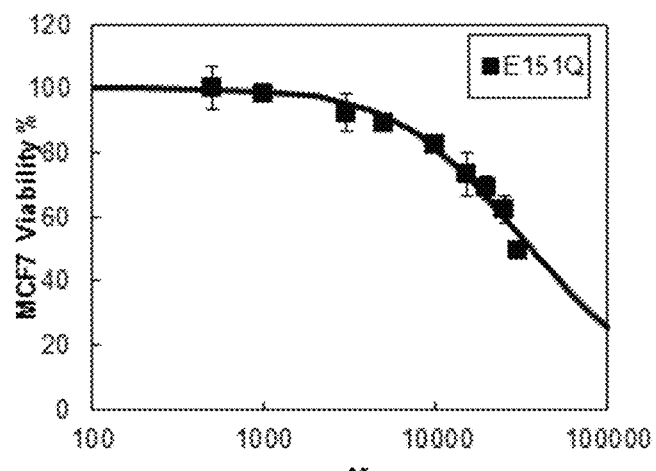
FIG. 10A illustrates MTT assays of stapled E151Q against MCF7 cells.
Figure 10B:
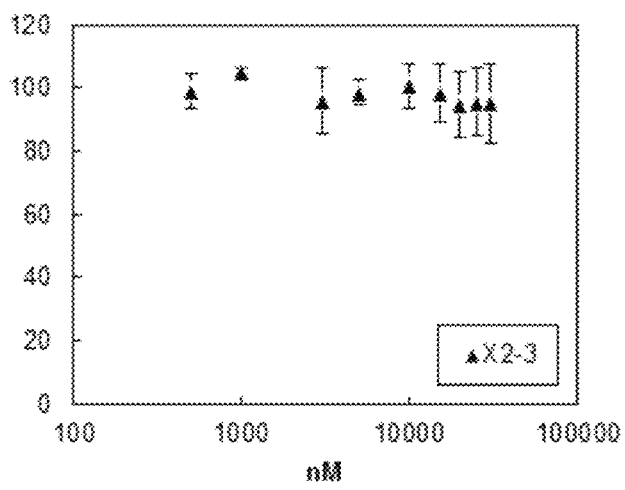
FIG. 10B illustrates MTT assays of stapled X2-3 against MCF7 cells.
Figure 10C:
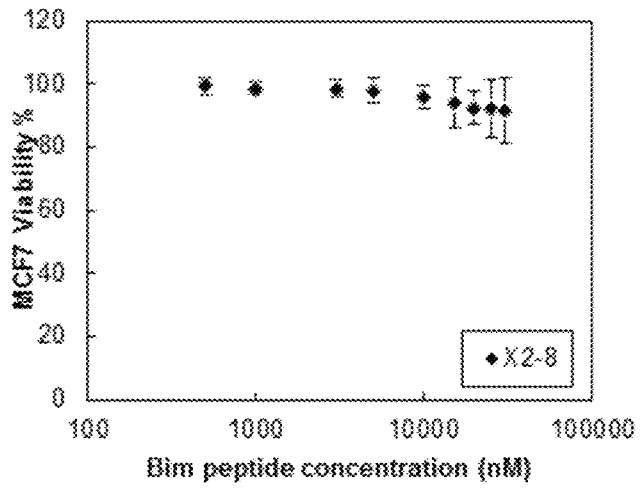
FIG. 10C illustrates MTT assays of stapled X2-8 against MCF7 cells.
Figure 10D:
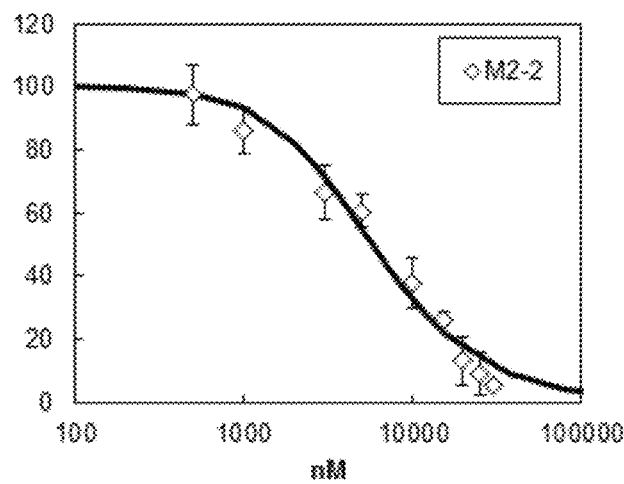
FIG. 10D illustrates MTT assays of stapled M2-2 against MCF7 cells.
Figure 10E:
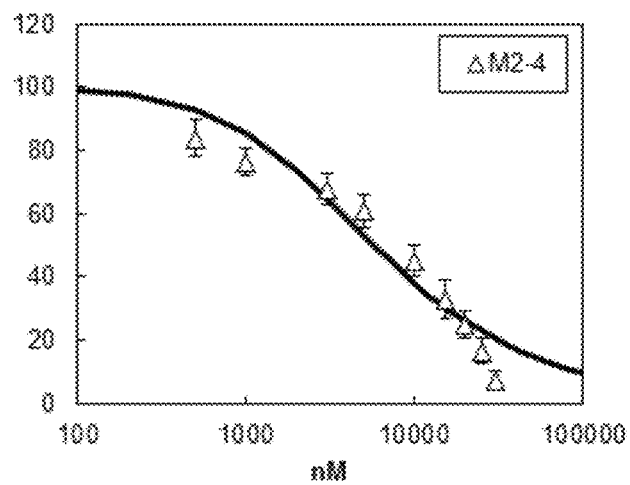
FIG. 10E illustrates MTT assays of stapled M2-4 against MCF7 cells.
Figure 11A:
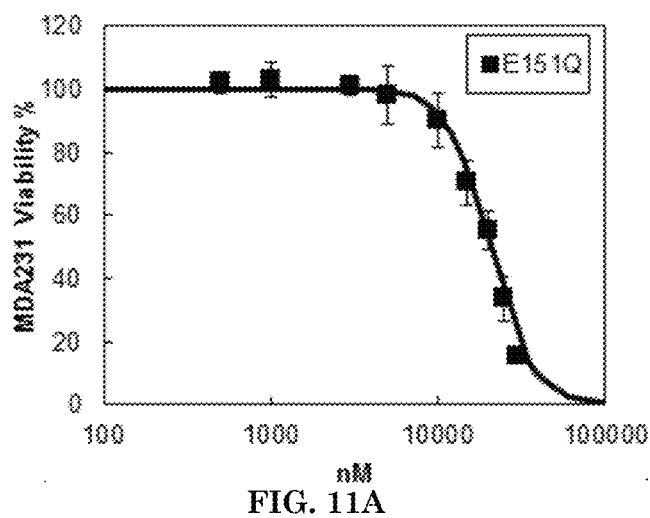
FIG. 11A illustrates MTT assays of stapled E151Q against MDA231 cells.
Figure 11B:
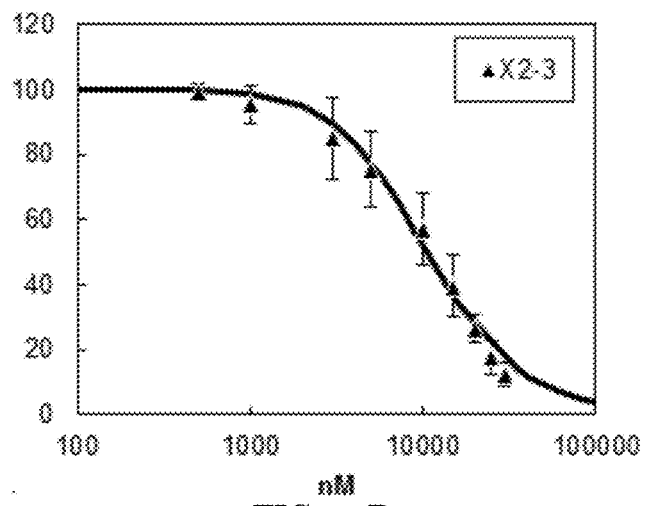
FIG. 11B illustrates MTT assays of stapled X2-3 against MDA231 cells.
Figure 11C:
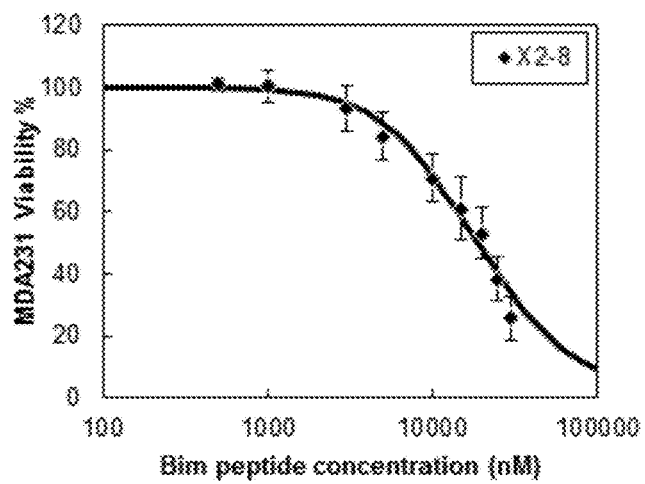
FIG. 11C illustrates MTT assays of stapled X2-8 against MDA231 cells.
Figure 11D:
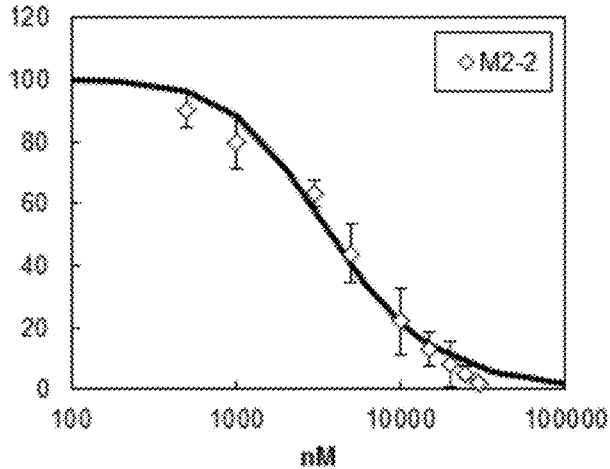
FIG. 11D illustrates MTT assays of stapled M2-2 against MDA231 cells.
Figure 11E:
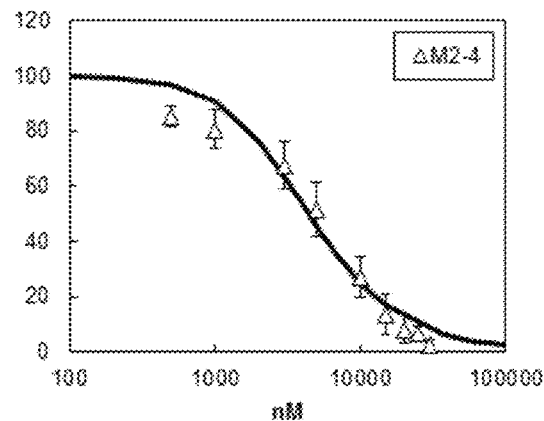
FIG. 11E illustrates MTT assays of stapled M2-4 against MDA231 cells.

The binding of wild-type Bim and each of the 5 Bim variants to each of the 5 anti-apoptotic proteins was assessed by determining apparent $K_d$ values for all possible pairwise interactions (see Table 3 below, FIGS. 7A-7AJ). As discussed above, the E151Q pseudo-wild-type peptide exhibited a 5-fold increase in apparent affinity toward Bcl-$x_L$ but otherwise bound to the other four pro-survival proteins with apparent $K_d$ values similar to the wild-type peptide (see Table 3 below). The variants X2-3 and X2-8, affinity matured toward Bcl-$x_L$, developed specificity toward Bcl-$x_L$ with large increases in apparent $K_d$ to all of the other pro-survival proteins except for A1 (see Table 3 below). The variants M2-2 and M2-4 chosen from the Mcl-1 screen, showed affinity improvement (3- and 6-fold, respectively) toward A1 as expected because Mcl-1 and A1 fall within the same subclass of pro-survival proteins (Chen et al., Mol. Cell., 2005 [25], which is incorporated herein by reference as if fully set forth). Variant M2-2 lost the ability to bind Bcl-$x_L$, Bcl-2 and Bcl-w (see Table 3 below), resulting in a "Noxa-like" peptide specific to the Mcl-1/A1 subclass. In stark contrast to the other affinity matured variants, the M2-4 variant exhibited affinity improvements toward Mcl-1 and A1, while maintaining wild-type affinity toward Bcl-$x_L$, Bcl-2 and Bcl-w (see Table 3 below). In this way, the M2-4 variant maintains the promiscuous binding profile of the wild-type Bim peptide while also exhibiting improved binding to the Mcl-1/A1 subclass.

Apparent $K_d$ values for wild-type Bim, pseudo-wild-type Bim (E151Q), and four affinity-matured Bim variants toward each of the five pro-survival proteins are shown in Table 3 below. Raw data can be found in FIGS. 6A-6E and 7A-7AJ.

TABLE 3

| $K_d$ (nM) | Bcl-$x_L$ | Bcl-2 | Bcl-w | Mcl-1 | A1 |
|---|---|---|---|---|---|
| WT | 251 | 97.9 | 594 | 37.7 | 26.9 |
| E151Q | 47.4 | 175 | 642 | 45.2 | 29.6 |
| X2-3 | 9.28 | 929 | 5890 | 1300 | 30.2 |
| X2-8 | 17.8 | 2350 | 946 | 2580 | 40.5 |
| M2-2 | 2800 | >10 µM | >10 µM | 5.80 | 9.99 |
| M2-4 | 333 | 93.7 | 542 | 9.85 | 4.18 |

Example 5—Cytotoxicity of Stapled Bim Variants

Figure 3C:
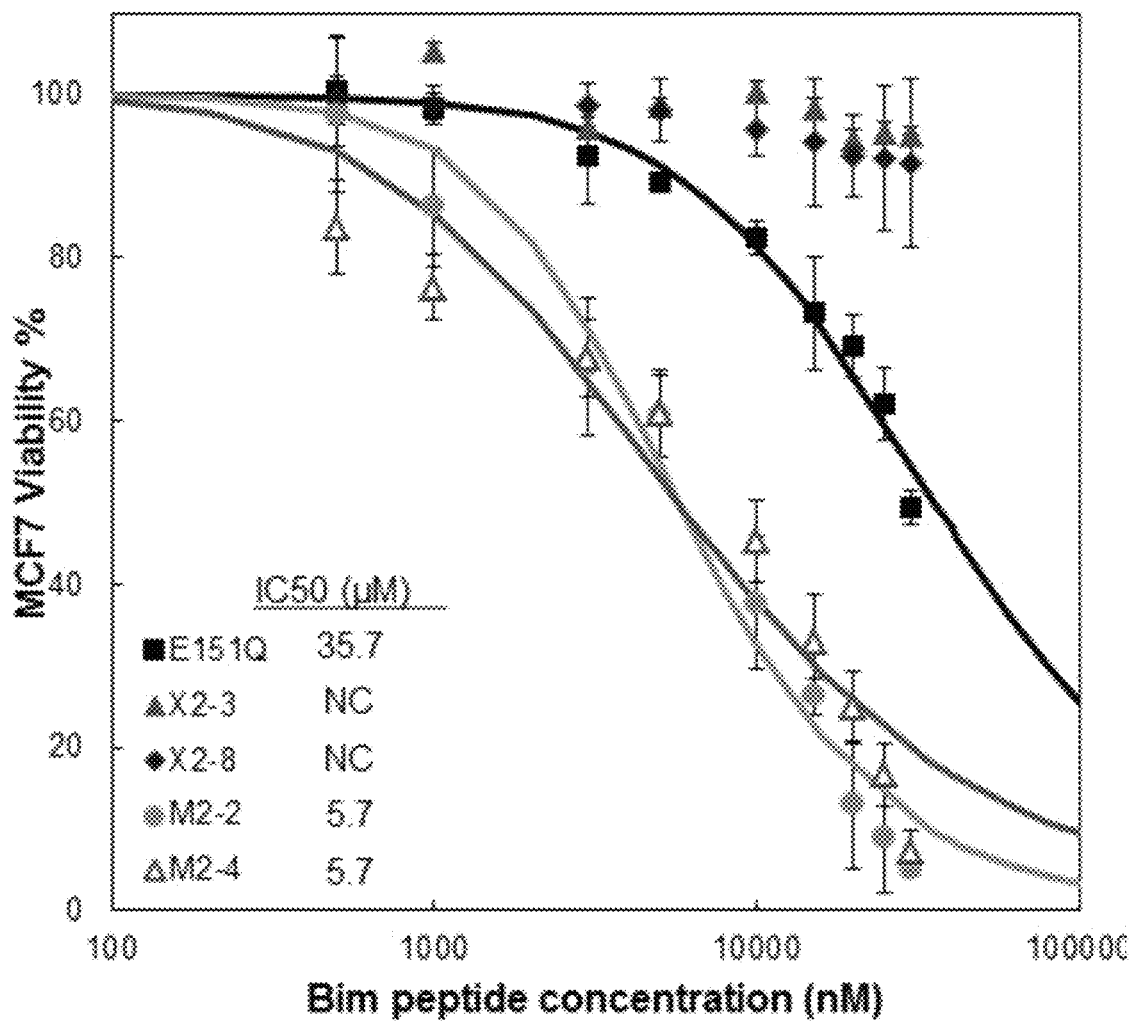
FIG. 3C illustrates cytotoxicity of pseudo-wild-type and affinity matured Bim BH3 peptides toward MCF7 cells. Error bars represent the standard deviation from three biological replicates.
Figure 3D:
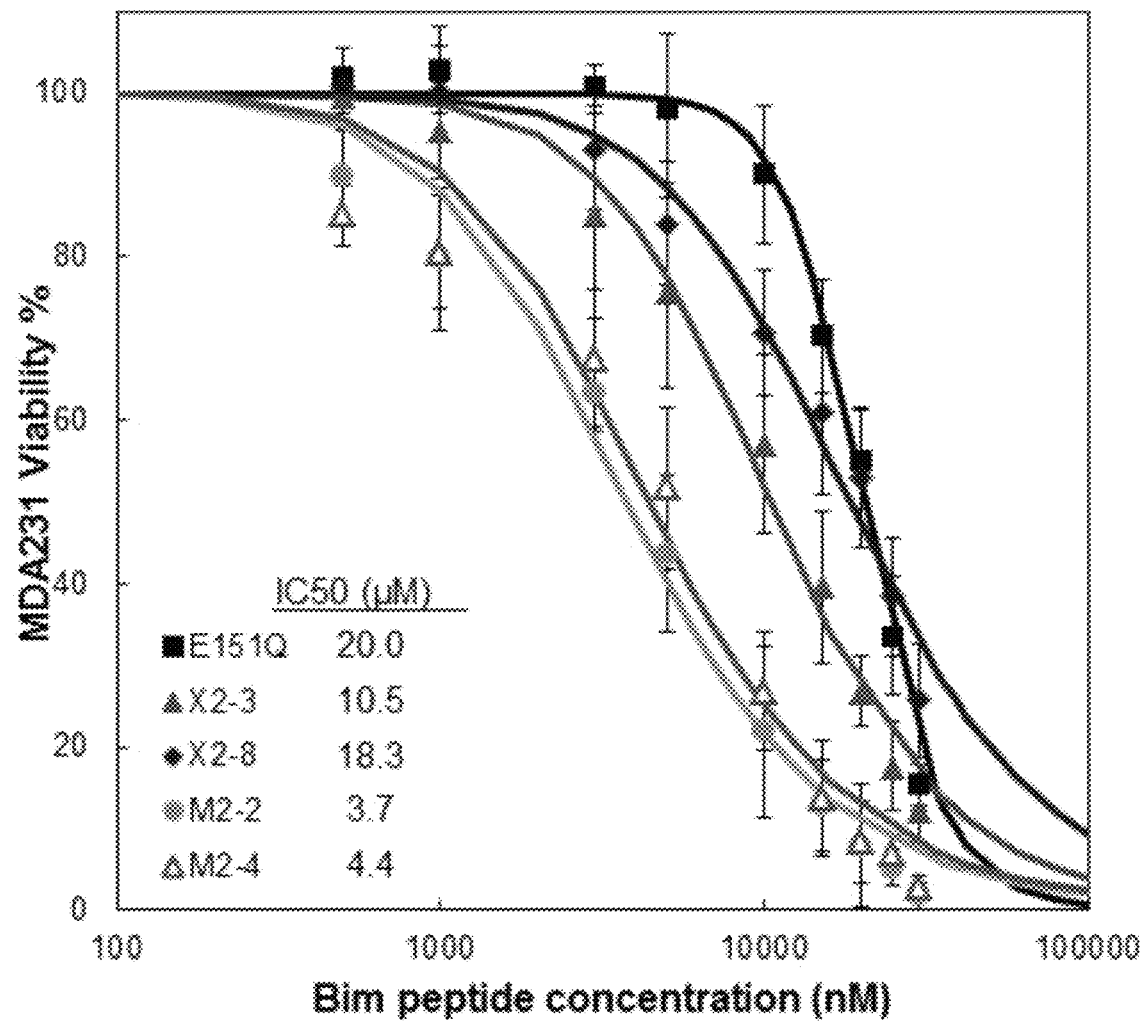
FIG. 3D illustrates cytotoxicity of pseudo-wild-type and affinity matured Bim BH3 peptides toward MDA231 cells. Error bars represent the standard deviation from three biological replicates.
Figure 5A:
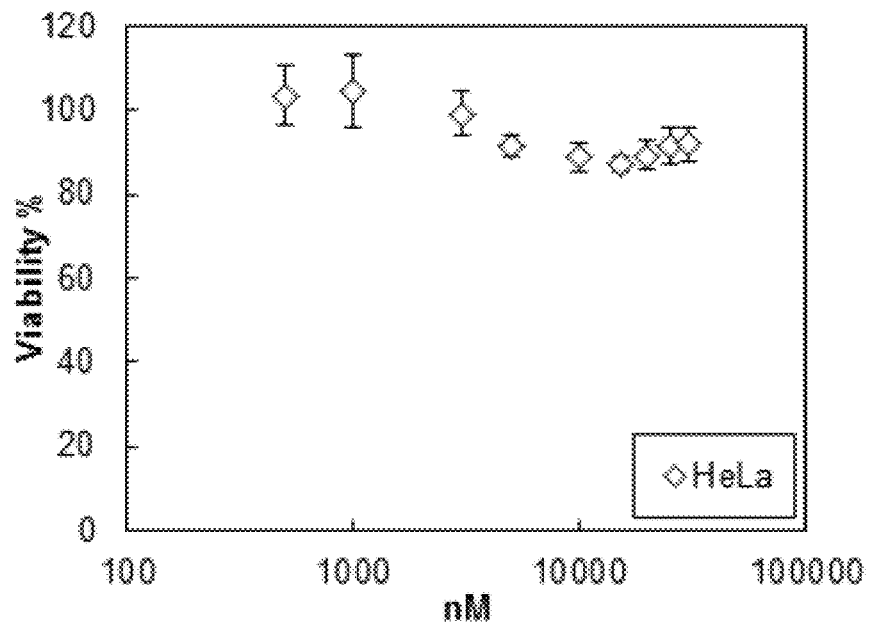
FIGS. 5A-5D illustrate MTT assays of stapled wild-type Bim peptide. No cytotoxicity was observed up to 30 µM peptide concentration.
Figure 5B:
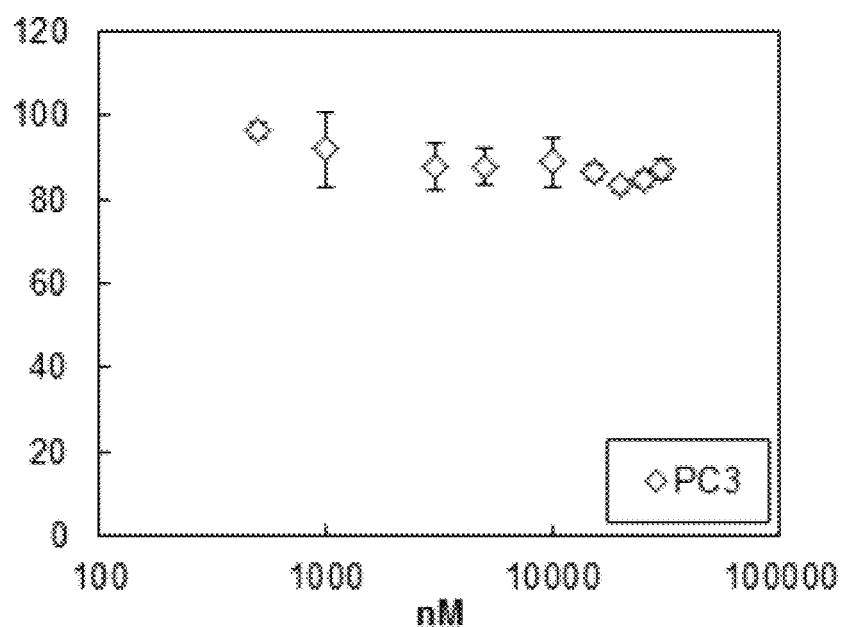
Figure 5C:
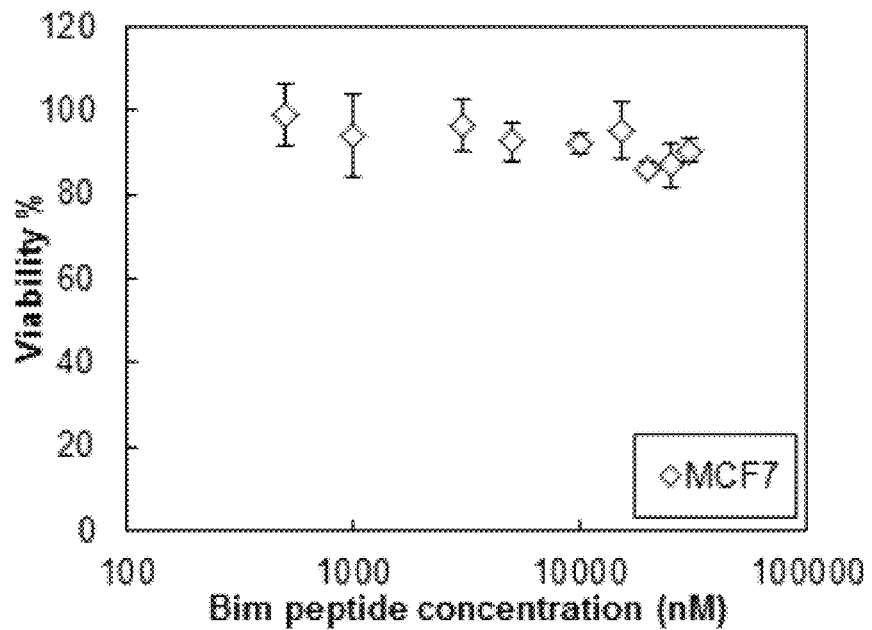
Figure 5D:
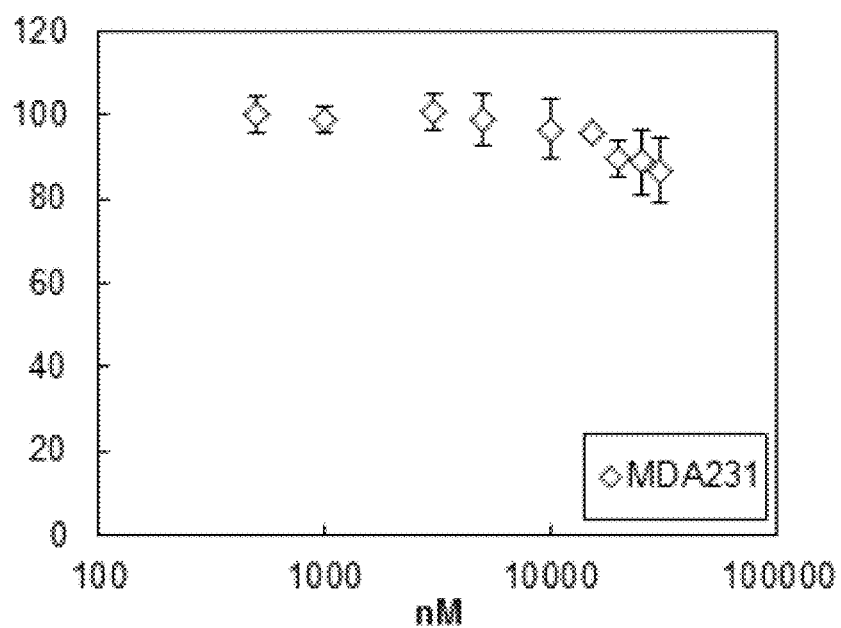

Stapled versions of the Bim 14-mer wild-type peptide, the E151Q pseudo-wild-type peptide, and the X2-3, X2-8, M2-2, and M2-4 variants were synthesized based on the detailed protocol described of Kim et al, Nat. Protoc, 2011 [21], which is incorporated herein by reference as if fully set forth. The cytotoxicity of these peptides was tested on four different cancer cell lines derived from three different organs: cervical adenocarcinoma (HeLa), prostate carcinoma (PC3), and breast cancer (MCF7 and MDA-MB-231). As mentioned briefly above, the stapled wild-type Bim 14-mer peptide had no cytotoxicity even with a dose of 30 µM, the highest concentration tested (FIGS. 5A-5D). The pseudo-wild-type peptide containing the charge-neutralizing E151Q substitution had measurable but modest cytotoxicity against all four cell lines with values of $IC_{50}$ ranging from about 10-150 µM (FIG. 3, an alternative view of these data is in FIGS. 8A-8E, 9A-9E, 10A-10E, and 11A-11E, and see Table 4, Table 5, Table 6 and Table 7, below). The X2-3 and X2-8 variants, which exhibit specific, avid binding to only Bcl-$x_L$ and A1, were slightly more cytotoxic to HeLa cells and MDA-MB-231 cells than the pseudo-wild-type peptide. However these Bcl-$x_L$-matured peptides are less cytotoxic to PC3 cells and have no cytotoxicity toward MCF7 cells at the concentrations tested (FIGS. 3B and 3C). Fortunately, affinity maturation toward Mcl-1 proved to be a more fruitful strategy in improving the cytotoxicity of the stapled Bim peptide. Both the M2-2 and M2-4 peptides had potent ($IC_{50}$<6.2 µM) cytotoxicity against all four cell lines (FIGS. 3A-3D). The M2-4 peptide, which binds with single nanomolar apparent $K_d$ to Mcl-1 and A1 while maintaining promiscuous binding to all five pro-survival proteins, was the most potent agent in our studies exhibiting $IC_{50}$ values as low as 1 µM for HeLa cells and 1.4 µM for PC3 cells. In the case of HeLa cells, this represents a remarkable ~150-fold decrease in $IC_{50}$ relative to the pseudo-wild-type peptide.

$IC_{50}$ values of the variants against HeLa cells are listed in Table 4, below.

TABLE 4

| HeLa | IC50 (µM) | $R^2$ |
|---|---|---|
| E151Q | 149.9 | 0.990 |
| X2-3 | 51.3 | 0.967 |
| X2-8 | 55.0 | 0.985 |
| M2-2 | 6.1 | 0.989 |
| M2-4 | 1.0 | 0.934 |

$IC_{50}$ values of the variants against PC3 cells are listed in Table 5, below.

TABLE 5

| PC3 | IC50 (µM) | $R^2$ |
|---|---|---|
| E151Q | 9.5 | 0.944 |
| X2-3 | 17.9 | 0.989 |
| X2-8 | 14.9 | 0.951 |
| M2-2 | 4.7 | 0.912 |
| M2-4 | 1.4 | 0.928 |

$IC_{50}$ values of the variants against MCF7 cells are listed in Table 6, below.

TABLE 6

| MCF7 | IC50 (µM) | $R^2$ |
|---|---|---|
| E151Q | 35.7 | 0.974 |
| X2-3 | NC | |
| X2-8 | NC | |
| M2-2 | 5.7 | 0.976 |
| M2-4 | 5.7 | 0.916 |

$IC_{50}$ values of the variants against MDA231 cells are listed in Table 7, below.

TABLE 7

| MDA231 | IC50 (µM) | $R^2$ |
|---|---|---|
| E151Q | 20.0 | 0.990 |
| X2-3 | 10.5 | 0.989 |
| X2-8 | 18.3 | 0.978 |
| M2-2 | 3.7 | 0.978 |
| M2-4 | 4.4 | 0.958 |

The most potent stapled peptide, M2-4, was studied in more depth. First, an N-terminally fluorescein-tagged variant of stapled M2-4 (Fl-M2-4) was prepared. HeLa cells were incubated with 5 µM Fl-M2-4 and imaged after 2.5 hours. The presence of diffuse green fluorescence throughout the cell indicated that the peptide had been taken up into the cells (FIGS. 4A-4C). Continued incubation of the peptide for another 2.5 hours did not lead to appreciable increases in fluorescence, indicating that peptide uptake occurs rapidly in these cells. HeLa cells were also treated with unlabeled stapled M2-4 to confirm that the cytotoxicity observed was due to apoptosis. After incubating HeLa cells with 5 µM stapled M2-4 peptide for 5 hours, the cell exhibited DNA fragmentation as judged by the TUNEL assay (FIGS. 4D-4F).

Example 6—Experimental Methods

Example 6.1—Bacterial Strains, Plasmid and Library Construction

The inventors found that a minimal BH3 core peptide of Bim with a length of 14 amino acids that retains promiscuous, avid binding to all five pro-survival proteins (Zhang et al., Integr. Biol, 2011 [20], which is incorporated herein by reference as if fully set forth). Starting from this 14-mer Bim, a library was created by introducing degeneracy at 4 positions, I148, E151, I155, and F159. The 3 hydrophobic and 1 charged residues were allowed to vary to any of the 20 amino acids using the NNK degenerate codon where N is any of the four bases, and K is G or T. The Bim library was constructed as an N-terminal fusion to enhanced circularly permuted OmpX (eCPX), and cloned into an arabinose-inducible pBAD33 vector. The MC1061 strain of E. coli was used for all surface display experiments. Cloning of the E151 mutants (pSZ54-58, see Table 8 below, see Table 10 below) was carried out in E. coli strain XL-1 Blue, and expression of these constructs was in MC1061.

Plasmids created and used in this study are listed in Table 8, below.

TABLE 8

| Plasmid name | Description |
|---|---|
| pSZ33 | Bim (147-160) on eCPX |
| pSZ54 | Bim E151Q |
| pSZ55 | Bim E151L |
| pSZ56 | Bim E151T |
| pSZ57 | Bim E151W |
| pSZ58 | Bim E151I |

Example 6.2—Pro-Survival Bcl-2 Protein Expression and Purification

Expression and purification of all anti-apoptotic proteins were carried out in BL21 E. coli strain. Details of the expression and purification of biotinylated Bcl-$x_L$, Bcl-2, Bcl-w, Mcl-1 and A1 can be found in Zhang et al., Integr. Biol, 2011 [20], which is incorporated herein by reference as if fully set forth. Briefly, a pASK75 plasmid containing the biotinylated pro-survival protein and a pMon-BirA plasmid encoding a constitutively expressed copy of the E. coli biotin ligase were co-transformed into BL21. A 1 L or 2 L culture was grown with biotin (2 mg/L) added at $OD_{600}$~0.2 and induced with 0.2 mg/L anhydrotetracycline at $OD_{600}$~1. Protein expression was induced for 3-4 hours at room temperature and cells were pelleted. After cell lysis by sonication and lysozyme treatment, the protein was purified using Ni-NTA resin (Qiagen), and buffer exchanged into 2× phosphate-buffered saline (PBS) for binding experiments.

Example 6.3—Binding Assays, Library Screening, and Apparent $K_d$ Measurement

All binding assays were performed using MC1061 strain. Briefly, a 5 mL culture of a library sample or individual variant was grown to $OD_{600}$~0.6, and induced with arabinose (0.2%) at RT for 2.5 hours. Cells were pelleted (1 mL culture, 6000 rpm, 5 min) and resuspended in 1 mL PBS. A portion of the cell suspension (50 μL) was mixed with the desired concentration of pro-survival protein to a total volume of 500 μL. The mixture was allowed to rotate at room temperature for 1 hour for equilibrium binding. The cells were pelleted again (6000 rpm, 20 min), resuspended with 100 μL of 50 nM streptavidin-phycoerythrin (SAPE), and incubated on ice in the dark for 30 min. After a final centrifugation, the cell pellets were stored on ice and resuspended in 2 mL of PBS for flow cytometry measurements. A Partec CyFlow ML Flow Cytometer equipped with a 488 nm laser was used to analyze the cells. A FACSVantage SE cell sorter was used for cell sorting in single cell mode.

Example 6.4—Synthesis and Characterization of Stapled Peptides

Synthesis of stapled Bim peptides was performed following the detailed protocol described by Kim et al., Nat. Protoc., 2011 [21], which is incorporated herein by reference as if fully set forth. All common amino acids and Rink Amide MBHA resin were purchased from NovaBiochem. The olefinic Fmoc-protected (S)-N-Fmoc-2-(4'-pentenyl) alanine (Fmoc-$S_5$-OH) was purchased from Okeanos Tech Co. Ltd. The coupling reagent PyClock and HOBt were purchased from Advanced ChemTech. All other chemicals and solvents were purchased from Sigma-Aldrich.

Within the Bim 14-mer core peptide, R154 and E158 were replaced by α, α-disubstituted 5-carbon olefinic unnatural amino acid in order to create the "staple." Solid-phase peptide synthesis was performed manually using Rink amide MBHA resin (0.59 mmol/g, 30 μmol) and Fmoc-protected amino acids. To couple natural Fmoc-protected amino acids, 5 equivalents of the amino acid and 5 equivalents of PyClock (0.2 M in 750 μL of NMP) were mixed first, and then mixed with 10 equivalents of DIPEA (52 μL). The mixture was added to the resin and allowed to react under gentle $N_2$ bubbling for an hour. To couple the olefinic amino acids, only 3 equivalents of the amino acids were used with a 1:1:2 ratio of amino acid/PyClock/DIPEA, but the reaction was carried out for 2 hours to ensure a high extent of coupling. For Fmoc deprotection, 1.5 mL of 25% piperidine/NMP with 0.1 M HOBt was mixed with the resin under $N_2$ agitation for 10 min. This procedure was repeated twice. Amino acids being coupled immediately after the two unnatural amino acids (D157 and R153) went through two rounds of 90 min coupling to ensure good conversion because the α, α-disubstituted amino acid introduced more steric hindrance. The resin was thoroughly washed with DCM and NMP following each deprotection and coupling step. After assembling the full sequence, olefin methathesis was carried out in the solid phase using 1 mL of 6 mM solution of Grubbs first-generation catalyst in dichloroethane (DCE). The mixture was gently agitated via continuous $N_2$ bubbling for 2 hours at RT and repeated one more time with another mL of fresh Grubbs catalyst. After the removal of the last Fmoc group, thorough washing and drying, peptides were cleaved off the resin using a cocktail of TFA/TIS/$H_2O$ (95:2.5:2.5). The cleavage cocktail was removed via evaporation and the residue was precipitated in diethyl ether. The crude product was analyzed and purified using HPLC (Agilent 1200 Series instrument equipped with Agilent Zorbax 300SB-$C_{18}$ columns: a 4.6×150 mm analytical column and a 9.4×250 mm semi-prep column). The purified product was confirmed by Agilent 6220 Accurate-Mass Time-of-Flight LC/MS (see Table 9 below). The purified peptides were lyophilized and stored until required. The presence of tryptophan in the peptides allowed for accurate concentration determinations by $A_{280}$. N-terminally FITC-labeled peptides were synthesized in a similar fashion except that a β-alanine residue was coupled to the resin bound peptide following metathesis (Kim et al, Nat. Protoc, 2011 [21], which is incorporated herein by reference as if fully set forth). The resulting peptide was reacted with excess FITC (0.37 M) in DMF with 0.74 DIPEA.

Masses of stapled Bim peptides are listed in Table 9, below.

TABLE 9

| Stapled Peptides | Calculated (Da) | Observed (Da) |
| --- | --- | --- |
| Bim WT | 1711.815 | 1711.94 |
| E151Q | 1710.835 | 1710.95 |
| X2-3 | 1827.955 | 1827.96 |
| X2-8 | 1745.875 | 1745.96 |
| M2-2 | 1633.795 | 1633.97 |
| M2-4 | 1661.835 | 1661.99 |

Example 6.5—Mammalian Cell Culture and Cytotoxicity Assays

HeLa, PC3, MCF7 and MDA231 cell lines were used to determine $IC_{50}$ of each stapled peptide. All cells were cultured at 37° C. supplemented with 5% $CO_2$. HeLa cells and PC3 cells were maintained in DMEM and RPMI 1640 media, respectively, supplemented with 10% FBS, 50 units/mL penicillin, and 50 μg/mL streptomycin. MCF7 cells were maintained in DME/F12 media with 2% FBS, 10 μg/ml insulin, and 50 μg/ml gentamicin. MDA-MB-231 cells were maintained in DME/F12 media supplemented with 10% FBS, 10 μg/ml insulin, and 50 μg/ml gentamicin. The cytotoxicity of stapled peptides was determined using an MTT (3-(4,5-Dimethylthiazol-2-yl)-2,5-diphenyltetrazolium bromide assay (Sigma). Cells were plated at a density of $1.5 \times 10^4$ cells per well in a 96-well plate. After 24 hours, the medium was replaced with serum-free medium containing stapled peptides. Serum was added after 4 hours, and cells were incubated for an additional 44 hours. After this incubation, 0.5 mg/ml of MTT was added to each well and incubated for 4 hours. The medium was aspirated and 200 μL of dimethyl sulfoxide (DMSO) was added to each well to solubilize the formazan crystals. The absorbance was measured at 570 nm with 690 nm as an internal reference using a GloMax-Multi Detection System (Promega). Experiments were performed three times independently with biological replicates.

Example 6.6—Peptide Uptake and TUNEL Assay

To study the uptake of fluorescein-labeled M2-4 stapled peptide (Fl-M2-4), HeLa cells were cultured in DMEM with 10% FBS and antibiotics as described above. The peptide was added to a final concentration of 5 μM in fresh DMEM without serum supplementation. Cellular uptake of Fl-M2-4 was visualized using a Hamamatsu Orca CCD camera attached to a Nikon Eclipse Ti microscope after 2.5 hours of incubation. Cells were fixed using 4% paraformaldehyde and counterstained with Hoechst 33342. For the TUNEL assay, HeLa cells were plated on a fibronectin-treated coverslip and incubated with 5 μM unlabeled M2-4 peptide for 5 hours. The cells were then fixed using 4% paraformaldehyde and permeabilized with 0.25% Triton X-100 in PBS.

The TUNEL assay (Click-it Alexa-Fluor 594, Invitrogen) was carried out according to the manufacturer's recommendations including counterstaining cell nuclei with Hoechst 33342. Images were acquired using a Hamamatsu Orca CCD camera attached to a Nikon Eclipse Ti microscope. All images were processed with ImageJ software.

Example 6.7—Library Construction

The Bim 14-mer (147-160) NNK saturation mutagenesis library was constructed by performing two PCRs using primers 1 and 4 and primers 2 and 3 (see Table 10 below) with WT Bim plasmid pSZ33 as template. After overlapping the products of these two PCRs, the resulting piece was digested with KpnI and HindIII. The digested product was ligated with pBAD33 vector that also has been digested with KpnI and HindIII. The ligation product was incubated at 70° C. for 15 min to denature all enzymes and micro-dialyzed on a nitrocellulose membrane to remove all salts. The clean ligation product was then transformed into electrocompetent MC1061 cells. The transformation efficiency and the size of the library were estimated by spreading a small amount of the transformation mixture on LB/chloramphenicol plates. The library was estimated to be around 4.5 million in size, thus covering more than 99% of the 1 million theoretical space. The rest of the transformation mixture was recovered in 500 mL of LB/chloramphenicol liquid medium and grew to $OD_{600}$ of 1. The cell culture was then made into frozen stocks.

Example 6.8—Cloning of E151 Mutants

Five different E151 (Q, L, T, W, I) mutants were constructed using forward primers 5-9 and reverse primer 4 (see Table 10 below). Each mutant piece was digested using KpnI and HindIII and ligated into pBAD33. The ligation product was transformed into chemical competent XL-1 blue. After sequence confirmation, the plasmids (pSZ54-58) were then transformed into MC1061 and frozen stocks were made for binding experiments.

Primers used for Bim library construction and cloning of E151 variants are listed in Table 10, below. K is G or T and M is the complement of K in the sequences of Table 10. N is any of A, G, C or T.

TABLE 10

| Primer | Description | Sequence |
|---|---|---|
| 1 | Bim NNK library Forward | GTCTGGCCAGTGGNNKGCCCAANN KTTGCGGCGTNNKGGAGACGAGNN KAACGGAGGGCAG (SEQ ID NO: 13) |
| 2 | Bim NNK library Reverse | CTGCCCTCCGTTMNNCTCGTCTCC MNNACGCCGCAAMNNTTGGGCMNN CCACTGGCCAGAC (SEQ ID NO: 14) |
| 3 | Forward pre-KpnI in pBDeCPX | GCAACTCTCTACTGTTTCTCCATA CC (SEQ ID NO: 15) |
| 4 | Reverse post-HindIII in pBDeCPX | CCAAAACAGCCAAGCTTGGCCACC TTGG (SEQ ID NO: 16) |
| 5 | E151Q Forward | CCGTAGCTGGCCAGTCTGGCCAGT GGATCGCCCAACAGTTGCGGCGTA TTGG (SEQ ID NO: 17) |

TABLE 10-continued

| Primer | Description | Sequence |
|---|---|---|
| 6 | E151L Forward | CCGTAGCTGGCCAGTCTGGCCAGT GGATCGCCCAATTGTTGCGGCGTA TTGG (SEQ ID NO: 18) |
| 7 | E151T Forward | CCGTAGCTGGCCAGTCTGGCCAGT GGATCGCCCAAACTTTGCGGCGTA TTGG (SEQ ID NO: 19) |
| 8 | E151W Forward | CCGTAGCTGGCCAGTCTGGCCAGT GGATCGCCCAATGGTTGCGGCGTA TTGG (SEQ ID NO: 20) |
| 9 | E151I Forward | CCGTAGCTGGCCAGTCTGGCCAGT GGATCGCCCAAATTTTGCGGCGTA TTGG (SEQ ID NO: 21) |

Example 6.9—Binding Affinity Calculation

A two parameter model was used to extract apparent binding affinity ($K_d$) from flow cytometry binding experiments.

$$\text{Median Fluorescence} = \frac{B_{max}C}{K_d + C} \quad (C: \text{concentration of anti-apoptotic protein})$$

Example 6.10—IC50 Calculation

A four-parameter model was used to fit the experimental data and extract the IC50 value from killing assays, where log [ ] was the log value of the stapled peptide concentration.

$$\text{Viability} = \text{bottom} + \frac{\text{top} - \text{bottom}}{1 + \left(\frac{\log[\ ]}{\log[IC50]}\right)^{Hill\ slope}}$$

During fitting, "top" was always fixed at 100% viability, while "bottom," log[IC50] and Hill slope were allowed to vary. In all cases, "bottom" came out to be 0. The $R^2$ values of all fits were above 0.9, while the majority was above 0.95.

Example 7—Use of Composition as a Reagent for Drug Discovery Efforts

The compositions described herein by be used as a reagent for drug discovery efforts. For example, the engineered cytotoxic stapled BH3 peptides or peptide compositions described herein have high affinity which allows them to be used as a competitor for small molecule drug discovery against Mcl-1. This may be accomplished by a high throughput screen of small molecules in which one looks for displacement of the peptide by a small molecule. This would indicate that the small molecule has an ever higher affinity than does the peptide.

REFERENCES

[1] Chipuk, J. E., Moldoveanu, T., Llambi, F., Parsons, M. J. & Green, D. R. The BCL-2 Family Reunion. *Molecular Cell* 37, 299-310 (2010).

[2] Walensky, L. D. BCL-2 in the crosshairs: tipping the balance of life and death. *Cell Death and Differentiation* 13, 1339-1350 (2006).

[3] Chipuk, J. E. & Green, D. R. How do BCL-2 proteins induce mitochondrial outer membrane permeabilization? *Trends in Cell Biology* 18, 157-164 (2008).

[4] Sattler, M. et al. Structure of Bcl-x(L)-Bak peptide complex: Recognition between regulators of apoptosis. *Science* 275, 983-986 (1997).

[5] Tsujimoto, Y., Cossman, J., Jaffe, E. & Croce, C. M. Involvement of the Bcl-2 Gene in Human Follicular Lymphoma. *Science* 228, 1440-1443 (1985).

[6] Selzer, E. et al. Expression of Bcl-2 family members in human melanocytes, in melanoma metastases and in melanoma cell lines. *Melanoma Research* 8, 197-203 (1998).

[7] Placzek, W. J. et al. A survey of the anti-apoptotic Bcl-2 subfamily expression in cancer types provides a platform to predict the efficacy of Bcl-2 antagonists in cancer therapy. *Cell Death & Disease* 1, e40 (2010).

[8] Letai, A. G. Diagnosing and exploiting cancer's addiction to blocks in apoptosis. *Nature Reviews Cancer* 8, 121-132 (2008).

[9] Petros, A. M., Olejniczak, E. T. & Fesik, S. W. Structural biology of the Bcl-2 family of proteins. *Biochimica Et Biophysica Acta-Molecular Cell Research* 1644, 83-94 (2004).

[10] Labi, V., Grespi, F., Baumgartner, F. & Villunger, A. Targeting the Bcl-2-regulated apoptosis pathway by BH3 mimetics: a breakthrough in anticancer therapy? *Cell Death and Differentiation* 15, 977-987 (2008).

[11] Lessene, G., Czabotar, P. E. & Colman, P. M. BCL-2 family antagonists for cancer therapy. *Nature Reviews Drug Discovery* 7, 989-1000 (2008).

[12] Oltersdorf, T. et al. An inhibitor of Bcl-2 family proteins induces regression of solid tumours. *Nature* 435, 677-681 (2005).

[13] Walensky, L. D. et al. Activation of apoptosis in vivo by a hydrocarbon-stapled BH3 helix. *Science* 305, 1466-1470 (2004).

[14] Blackwell, H. E. & Grubbs, R. H. Highly efficient synthesis of covalently cross-linked peptide helices by ring-closing metathesis. *Angewandte Chemie-International Edition* 37, 3281-3284 (1998).

[15] Schafmeister, C. E., Po, J. & Verdine, G. L. An all-hydrocarbon cross-linking system for enhancing the helicity and metabolic stability of peptides. *Journal of the American Chemical Society* 122, 5891-5892 (2000).

[16] Chapman, R. N., Dimartino, G. & Arora, P. S. A highly stable short alpha-helix constrained by a main-chain hydrogen-bond surrogate. *Journal of the American Chemical Society* 126, 12252-12253 (2004).

[17] Verdine, G. L. & Walensky, L. D. The challenge of drugging undruggable targets in cancer: Lessons learned from targeting BCL-2 family members. *Clinical Cancer Research* 13, 7264-7270 (2007).

[18] Sun, J. J. et al. Reconstitution and Engineering of Apoptotic Protein Interactions on the Bacterial Cell Surface. *Journal of Molecular Biology* 394, 297-305 (2009).

[19] Zhang, S. Y., Long, A. & Link, A. J. A Comparison of Two Strategies for the Affinity Maturation of a BH3 Peptide toward Pro-Survival Bcl-2 Proteins. *ACS Synthetic Biology*, in press, DOI: 10.1021/sb200002m (2012).

[20] Zhang, S. Y. & Link, A. J. Bcl-2 Family Interactome Analysis Using Bacterial Surface Display. *Integrative Biology* 3, 823-831 (2011).

[21] Kim, Y. W., Grossmann, T. N. & Verdine, G. L. Synthesis of all-hydrocarbon stapled alpha-helical peptides by ring-closing olefin metathesis. *Nature Protocols* 6, 761-771 (2011).

[22] Bernal, F; Tyler, A. F.; Korsmeyer, S. J.; Walensky, L. D.; Verdine, G. L., *J. Am. Chem. Soc.* 2007, 129, 2456.

[23] Stewart, M. L., Fire, E., Keating, A. E. & Walensky, L. D. The MCL-1 BH3 helix is an exclusive MCL-1 inhibitor and apoptosis sensitizer. *Nature Chemical Biology* 6, 595-601 (2010).

[24] Rice, J. J. & Daugherty, P. S. Directed evolution of a biterminal bacterial display scaffold enhances the display of diverse peptides. *Protein Engineering Design & Selection* 21, 435-442 (2008).

[25] Chen, L. et al. Differential targeting of prosurvival Bcl-2 proteins by their BH3-only ligands allows complementary apoptotic function. *Molecular Cell* 17, 393-403 (2005).

[26] Dutta, S. et al. Determinants of BH3 Binding Specificity for Mcl-1 versus Bcl-x(L). *Journal of Molecular Biology* 398, 747-762 (2010).

[27] Quinn, B. A. et al. Targeting Mcl-1 for the therapy of cancer. *Expert Opinion on Investigational Drugs* 20, 1397-1411 (2011).

[28] Chen, S., Dai, Y., Harada, H., Dent, P. & Grant, S. Mcl-1 down-regulation potentiates ABT-737 lethality by cooperatively inducing bak activation and bax translocation. *Cancer Research* 67, 782-791 (2007).

[29] Lee, E. F. et al. A novel BH3 ligand that selectively targets Mcl-1 reveals that apoptosis can proceed without Mcl-1 degradation. *Journal of Cell Biology* 180, 341-355 (2008).

[30] van Delft, M. F.; Wei, A. H.; Mason, K. D.; Vandenberg, C. J.; Chen, L.; Czabotar, P. E.; Willis, S. N.; Scott, C. L.; Day, C. L.; Cory, S.; Adams, J. M.; Roberts, A. W.; Huang, D. C. S. *Cancer Cell* 2006, 10, 389.

[31] Gavathiotis, E. et al. BAX activation is initiated at a novel interaction site. *Nature* 455, 1076-U6 (2008).

[32] Li, Y. et al. Amplification of LAPTM4B and YWHAZ contributes to chemotherapy resistance and recurrence of breast cancer. *Nature Medicine* 16, 214-U121 (2010).

[33] Basma, H. et al. BCL-2 antisense and cisplatin combination treatment of MCF-7 breast cancer cells with or without functional p53. *Journal of Biomedical Science* 12, 999-1011 (2005).

[34] Takara, K. et al. Molecular changes to HeLa cells on continuous exposure to cisplatin or paclitaxel. *Cancer Chemotherapy and Pharmacology* 58, 785-793 (2006).

[35] Dowling, C. M. et al. Antitumor activity of Titanocene Y in xenografted PC3 tumors in mice. *Letters in Drug Design & Discovery* 5, 141-144 (2008).

[36] Thallinger, C. et al. Mcl-1 is a novel therapeutic target for human sarcoma: synergistic inhibition of human sarcoma xenotransplants by a combination of Mcl-1 antisense Oligonucleotides with low-dose cyclophosphamide. *Clinical Cancer Research* 10, 4185-4191 (2004).

[37] Thallinger, C. et al. Mcl-1 antisense therapy chemosensitizes human melanoma in a SCID mouse xenotransplantation model. *Journal of Investigative Dermatology* 120, 1081-1086 (2003).

[38] Hussain, S. R. A. et al. Mcl-1 is a relevant therapeutic target in acute and chronic lymphoid malignancies: Down-regulation enhances rituximab-mediated apoptosis and complement-dependent cytotoxicity. *Clinical Cancer Research* 13, 2144-2150 (2007).

The references cited throughout this application are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

It is understood, therefore, that this invention is not limited to the particular embodiments disclosed, but is intended to cover all modifications which are within the spirit and scope of the invention as defined by the appended claims; the above description; and/or shown in the attached drawings.

What is claimed is:

1. A method of treating cancer comprising administering to a cancer patient a composition comprising an engineered cytotoxic stapled BH3 peptide, the engineered cytotoxic stapled BH3 peptide comprising a fourteen amino acid sequence having at least 85% identity to one of:

(SEQ ID NO: 33)
Trp-Val-Ala-Gln-Trp-Leu-Arg-Xaa$_3$-Trp-Gly-Asp-Xaa$_5$-Phe-Asn;

(SEQ ID NO: 41)
Trp-Tyr-Ala-Gln-Ile-Leu-Arg-Xaa$_3$-Met-Gly-Asp-Xaa$_5$-Phe-Asn;

(SEQ ID NO: 42)
Trp-Leu-Ala-Gln-Leu-Leu-Arg-Xaa$_3$-Tyr-Gly-Asp-Xaa$_5$-Phe-Asn;

(SEQ ID NO: 35)
Trp-Val-Ala-Gln-Thr-Leu-Arg-Xaa$_3$-Trp-Gly-Asp-Xaa$_5$-Phe-Asn;

(SEQ ID NO: 37)
Trp-Val-Ala-Gln-Leu-Leu-Arg-Xaa$_3$-Ile-Gly-Asp-Xaa$_5$-Val-Asn;

(SEQ ID NO: 38)
Trp-Met-Ala-Gln-Ile-Leu-Arg-Xaa$_3$-Ile-Gly-Asp-Xaa$_5$-Val-Asn; or (SEQ ID NO: 39)
Trp-Leu-Ala-Gln-Leu-Leu-Arg-Xaa$_3$-Ile-Gly-Asp-Xaa$_5$-Ile-Asn, wherein a crosslink is between the Xaa$_3$ residue at position 8 of the fourteen amino acid sequence and the Xaa$_5$ residue at position 12 of the fourteen amino acid sequence.

2. The method of claim 1, wherein Xaa$_3$ and Xaa$_5$ are α,α-disubstituted 5-carbon olefinic unnatural amino acids and the crosslink is between Xaa$_3$ and Xaa$_5$.

3. The method of claim 2, wherein the engineered cytotoxic stapled BH3 peptide is 14, 15, or 16 amino acids in length.

4. The method of claim 1 wherein the engineered cytotoxic stapled BH3 peptide has the sequence Trp-Val-Ala-Gln-Trp-Leu-Arg-Arg-Trp-Gly-Asp-Glu-Phe-Asn (SEQ ID NO: 2); Trp-Tyr-Ala-Gln-Ile-Leu-Arg-Arg-Met-Gly-Asp-Glu-Phe-Asn (SEQ ID NO: 3); Trp-Leu-Ala-Gln-Leu-Leu-Arg-Arg-Tyr-Gly-Asp-Glu-Phe-Asn (SEQ ID NO: 4); Trp-Val-Ala-Gln-Thr-Leu-Arg-Arg-Trp-Gly-Asp-Glu-Phe-Asn (SEQ ID NO: 6); Trp-Val-Ala-Gln-Leu-Leu-Arg-Arg-Ile-Gly-Asp-Glu-Val-Asn (SEQ ID NO: 8); Trp-Met-Ala-Gln-Ile-Leu-Arg-Arg-Ile-Gly-Asp-Glu-Val-Asn (SEQ ID NO: 9); or Trp-Leu-Ala-Gln-Leu-Leu-Arg-Arg-Ile-Gly-Asp-Glu-Ile-Asn (SEQ ID NO: 10).

5. The method of claim 1, wherein the engineered cytotoxic stapled BH3 peptide has the structure of:

Trp-Val-Ala-Gln-Trp-Leu-Arg-Xaa₃-Trp-Gly-Asp-Xaa₅-Phe-Asn;
(SEQ ID NO: 33)
[crosslink between Xaa₃ and Xaa₅]
(SEQ ID NO: 41)

Trp-Tyr-Ala-Gln-Ile-Leu-Arg-Xaa₃-Met-Gly-Asp-Xaa₅-Phe-Asn;
(SEQ ID NO: 42)

Trp-Leu-Ala-Gln-Leu-Leu-Arg-Xaa₃-Tyr-Gly-Asp-Xaa₅-Phe-Asn;
(SEQ ID NO: 35)

Trp-Val-Ala-Gln-Thr-Leu-Arg-Xaa₃-Trp-Gly-Asp-Xaa₅-Phe-Asn;
(SEQ ID NO: 37)

Trp-Val-Ala-Gln-Leu-Leu-Arg-Xaa₃-Ile-Gly-Asp-Xaa₅-Val-Asn;
(SEQ ID NO: 38)

Trp-Met-Ala-Gln-Ile-Leu-Arg-Xaa₃-Ile-Gly-Asp-Xaa₅-Val-Asn; or
(SEQ ID NO: 39)

Trp-Leu-Ala-Gln-Leu-Leu-Arg-Xaa₃-Ile-Gly-Asp-Xaa₅-Ile-Asn,

6. The method of claim 5, wherein the composition is administered to deliver a dose of 10 to 100 mg/kg/day of the engineered cytotoxic stapled BH3 peptide.

7. The method of claim 5, wherein Xaa₃ and Xaa₅ are α,α-disubstituted 5-carbon olefinic unnatural amino acids.

8. The method of claim 7, wherein the composition is administered to deliver a dose of 10 to 100 mg/kg/day of the engineered cytotoxic stapled BH3 peptide.

9. The method of claim 1, wherein the composition further comprises at least one of ABT-737 or ABT-199.

10. The method claim 1, wherein the engineered cytotoxic stapled BH3 peptide has the structure of:

Trp-Val-Ala-Gln-Trp-Leu-Arg-Xaa₃-Trp-Gly-Asp-Xaa₅-Phe-Asn,
(SEQ ID NO: 22)

wherein
Xaa₃ and Xaa₅ are α,α-disubstituted 5-carbon olefinic unnatural amino acids; and
the crosslink is between the Xaa₃ residue at position 8 of the fourteen amino acid sequence and the Xaa₅ residue at position 12 of the fourteen amino acid sequence.

11. The method of claim 1, wherein the engineered cytotoxic stapled BH3 peptide has the structure of:

Trp-Leu-Ala-Gln-Leu-Leu-Arg-Xaa₃-Tyr-Gly-Asp-Xaa₅-Phe-Asn;
(SEQ ID NO: 24)

wherein
Xaa₃ and Xaa₅ are α,α-disubstituted 5-carbon olefinic unnatural amino acids; and
the crosslink is between the Xaa₃ residue at position 8 of the fourteen amino acid sequence and the Xaa₅ residue at position 12 of the fourteen amino acid sequence.

12. The method of claim 1, wherein the engineered cytotoxic stapled BH3 peptide has the structure of:

Trp-Val-Ala-Gln-Leu-Leu-Arg-Xaa₃-Ile-Gly-Asp-Xaa₅-Val-Asn;
(SEQ ID NO: 28)

wherein
Xaa₃ and Xaa₅ are α,α-disubstituted 5-carbon olefinic unnatural amino acids; and
the crosslink is between the Xaa₃ residue at position 8 of the fourteen amino acid sequence and the Xaa₅ residue at position 12 of the fourteen amino acid sequence.

13. The method of claim 1, wherein the engineered cytotoxic stapled BH3 peptide has the structure of:

Trp-Leu-Ala-Gln-Leu-Leu-Arg-Xaa₃-Ile-Gly-Asp-Xaa₅-Ile-Asn,
(SEQ ID NO: 30)

wherein
Xaa₃ and Xaa₅ are α,α-disubstituted 5-carbon olefinic unnatural amino acids; and
the crosslink is between the Xaa₃ residue at position 8 of the fourteen amino acid sequence and the Xaa₅ residue at position 12 of the fourteen amino acid sequence.

14. The method of claim 13, wherein the composition further comprises a pharmaceutically acceptable carrier.

15. The method of claim 14, wherein the pharmaceutically acceptable carrier includes phosphate buffered saline (PBS).

16. The method of claim 1, wherein the composition further comprises a pharmaceutically acceptable carrier.

17. The method of claim 16, wherein the pharmaceutically acceptable carrier includes at least one substance selected from the group consisting of ion exchangers; alumina; aluminum stearate; lecithin; serum proteins; human serum albumin; buffer substances; phosphates; glycine; sorbic acid; potassium sorbate; partial glyceride mixtures of saturated vegetable fatty acids; water; salts; electrolytes; protamine sulfate; disodium hydrogen phosphate; potassium hydrogen phosphate; sodium chloride; zinc salts; colloidal silica; magnesium trisilicate; polyvinyl pyrrolidone; cellulose-based substances; sodium carboxymethylcellulose; waxes; polyethylene glycol; starch; lactose; dicalcium phosphate; microcrystalline cellulose; sucrose; dextrose; talc; magnesium carbonate; kaolin; non-ionic surfactants; edible oils; physiological saline; bacteriostatic water; and phosphate buffered saline (PBS).

18. The method of claim 1, wherein the patient is a human.

19. The method of claim 1, wherein the cancer patient is a breast cancer patient, a cervix cancer patient or a prostate cancer patient.

20. The method of claim 1, wherein the route of administration is selected from one or more of oral, injection, topical, enteral, rectal, gastrointestinal, sublingual, sublabial, buccal, epidural, intracerebral, intracerebroventricular, intracisternal, epicutaneous, intradermal, subcutaneous, nasal, intravenous, intraarterial, intramuscular, intracardiac, intraosseous, intrathecal, intraperitoneal, intravesical, intravitreal, intracavernous, intravaginal, intrauterine, extra-amniotic, transdermal, intratumoral, and transmucosal.

21. The method of claim 1, wherein the composition is administered to deliver a dose of 10 to 100 mg/kg/day of the engineered cytotoxic stapled BH3 peptide.

22. The method of claim 1, wherein the cancer patient is a cervix cancer patient.

23. The method of claim 22, wherein the composition further comprises a pharmaceutically acceptable carrier.

24. The method of claim 23, wherein the pharmaceutically acceptable carrier includes phosphate buffered saline (PBS).

25. The method of claim 1, wherein the composition is in the form of a transdermal patch, an oral tablet, or a controlled release pellet.

26. A method of treating cancer comprising administering to a cancer patient a composition comprising an engineered cytotoxic stapled BH3 peptide, the engineered cytotoxic stapled BH3 peptide comprising a fourteen amino acid sequence having the sequence of one of:

$$\text{Trp-Ile-Ala-Gln-Leu-Leu-Arg-}\overline{\text{Xaa}_3\text{-Ile-Gly-Asp-Xaa}_5}\text{-Val-Asn;}$$

or $$\text{Trp-Leu-Ala-Gln-Glu-Leu-Arg-}\overline{\text{Xaa}_3\text{-Ile-Gly-Asp-Xaa}_5}\text{-Val-Asn,}$$

wherein a crosslink is between the $Xaa_3$ residue at position 8 of the fourteen amino acid sequence and the $Xaa_5$ residue at position 12 of the fourteen amino acid sequence.

27. The method of claim 26, wherein the composition is administered to deliver a dose of 10 to 100 mg/kg/day of the engineered cytotoxic stapled BH3 peptide.

28. The method of claim 26, wherein $Xaa_3$ and $Xaa_5$ are α, α-disubstituted 5-carbon olefinic unnatural amino acids and the crosslink is between $Xaa_3$ and $Xaa_5$.

29. The method of claim 28, wherein the composition is administered to deliver a dose of 10 to 100 mg/kg/day of the engineered cytotoxic stapled BH3 peptide.

30. The method of claim 26 wherein the engineered cytotoxic stapled BH3 peptide has the sequence Trp-Ile-Ala-Gln-Ile-Leu-Arg-Arg-Trp-Gly-Asp-Glu-Phe-Asn (SEQ ID NO: 5); Trp-Ile-Ala-Gln-Leu-Leu-Arg-Arg-Ile-Gly-Asp-Glu-Val-Asn (SEQ ID NO: 7); or Trp-Leu-Ala-Gln-Glu-Leu-Arg-Arg-Ile-Gly-Asp-Glu-Val-Asn (SEQ ID NO: 11).

* * * * *